(12) United States Patent
Kuhajda et al.

(10) Patent No.: US 7,649,012 B2
(45) Date of Patent: Jan. 19, 2010

(54) COMPOUNDS, PHARMACEUTICAL COMPOSITIONS CONTAINING SAME, AND METHODS OF USE FOR SAME

(75) Inventors: Francis P. Kuhajda, Baltimore, MD (US); Susan M. Medghalchi, Baltimore, MD (US); Jill M. McFadden, Baltimore, MD (US); Jagan Thupari, Baltimore, MD (US)

(73) Assignees: FASgen, Inc., Baltimore, MD (US); Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/520,505

(22) PCT Filed: Jul. 9, 2003

(86) PCT No.: PCT/US03/21700

§ 371 (c)(1),
(2), (4) Date: Feb. 6, 2006

(87) PCT Pub. No.: WO2004/005277

PCT Pub. Date: Jan. 15, 2004

(65) Prior Publication Data

US 2006/0247302 A1 Nov. 2, 2006

Related U.S. Application Data

(60) Provisional application No. 60/394,585, filed on Jul. 9, 2002.

(51) Int. Cl.
*A61K 31/381* (2006.01)
*C07D 333/32* (2006.01)

(52) U.S. Cl. .......................... 514/445; 549/29; 549/62; 549/66; 514/438

(58) Field of Classification Search .................. 549/29, 549/62, 66; 514/438, 445
See application file for complete search history.

(56) References Cited

U.S. PATENT DOCUMENTS

| | | | |
|---|---|---|---|
| 4,565,699 | A | 1/1986 | Dolak |
| 5,679,801 | A * | 10/1997 | Caufield et al. ............. 549/64 |
| 6,376,682 | B1 | 4/2002 | Yamahara |
| 6,380,214 | B1 | 4/2002 | Gant et al. |
| 6,391,912 | B1 | 5/2002 | Hagemann et al. |
| 6,753,342 | B2 * | 6/2004 | Menta et al. ............. 514/414 |
| 7,459,481 | B2 * | 12/2008 | Thurpari et al. ........... 514/473 |

FOREIGN PATENT DOCUMENTS

| | | |
|---|---|---|
| JP | 58 059920 | 4/1983 |
| WO | WO 96/35664 | 11/1996 |
| WO | WO 01/49278 | 7/2001 |
| WO | WO 02/087565 | 11/2002 |
| WO | WO 2004/004712 | 1/2004 |

OTHER PUBLICATIONS

Berry et al (2001): STN International HCAPLUS database, (Columbus, Ohio), Accession No. 2001:507522.*
Caufield et al (1997): STN International HCAPLUS database, (Columbus, Ohio), Accession No. 1997:689567.*
Dils, R. et al., Fatty Acid Synthase from Rabbit Mammary Gland, Methods Enzymol., 35:74-83 (1975).
Falo, L.D. et al., Cerulenin Is a Potent Inhibitor of Antigen Processing by Antigen-Presenting Cells, The Journal of Immunology, 139:3918-3923 (1987).
Linn, T.C., Purification and Crystallization of Rat Liver Fatty Acid Synthetase, Archives of Biochemistry and Biophysics, 209(2):613-619 (1981).
Omura, Satoshi, The Antibiotic Cerulenin, a Novel Tool for Biochemistry as an Inhibitor of Fatty Acid Synthesis, Bacteriological Reviews, 40(3):681-697 (1976).
Simon, S.M. et al., Myristoylation of Proteins in the Yeast Secretory Pathway, The Journal of Biological Chemistry, 267(6):3922-3931 (1992).
Tomoda, H. et al., Evidence for an Essential Role of Long Chain Acyl-CoA Synthetase in Animal Cell Proliferation, The Journal of Biological Chemistry, 266(7):4214-4219 (1991).
Triscari, J. et al., Changes in Lipid Metabolism in Diet-Induced Obesity, Metabolism, 34(6):580-587 (1985).
Wakil, S.J., Fatty Acid Synthase, A Proficient Multifunctional Enzyme, Biochemistry, 28(11):4523-4530 (1989).
Sakya, S. M. et al., "Synthesis and Structure-activity Relationships of Thiotetronic Acid Analogues of Thiolactomycin," Bioogranic & Medicinal Chemistry Letters, 11 (20) pp. 2751-2754, 2001.
Supplementary European Search Report, dated Dec. 2003, pp. 1-4.

* cited by examiner

*Primary Examiner*—Golam M Shameem
(74) *Attorney, Agent, or Firm*—Fox Rothschild LLP

(57) ABSTRACT

A pharmaceutical composition comprising a pharmaceutical diluent and a compound of formula IV wherein $R^{21}$=H, $C_1$-$C_{20}$ alkyl, cycloalkyl, alkenyl, aryl, arylalkyl, or alkylaryl, —$CH_2OR^{25}$, —$C(O)R^{25}$, —$CO(O)R^{25}$, —$C(O)NR^{25}R^{26}$, —$CH_2C(O)R^{25}$, or —$CH^2C(O)NHR_{25}$, where $R_{25}$ and $R_{26}$ are each independently H, $C_1$-$C_{10}$ alkyl, cycloalkyl, alkenyl, aryl, arylalkyl, or alkylaryl, optionally containing one or more halogen atoms. $R^{22}$=—OH, —$OR^{27}$, —$OCH_2C(O)R^{27}$, —$OCH_2C(O)NHR^{27}$, —$OC(O)R^{27}$, —$OC(O)OR^{27}$, —$OC(O)NHNH$—$R^5$, or —$OC(O)NR^{27}R^{28}$, where $R^{27}$ and $R^{28}$ are each independently H, $C_1$-$C_{20}$ alkyl, cycloalkyl, alkenyl, aryl, arylalkyl, or alkylaryl, and where $R^{27}$ and $R^{28}$ can each optionally contain halogen atoms; $R^{23}$ and $R^{24}$, the same or different from each other, are $C_1$-$C_{20}$ alkyl, cycloalkyl, alkenyl, aryl, arylalkyl, or alkylaryl. Methods of using such formulations for the treatment of cancer, to effect weight loss, to treat microbially-based infections, to inhibit neuropeptide-Y and/or fatty acid synthase, and to stimulate CPT-1.

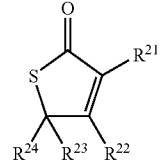

(IV)

11 Claims, 12 Drawing Sheets

Scheme 3.

a. EDC, DMAP, CH$_2$Cl$_2$, 0 °C- rt

Scheme 8.

Scheme 10.

COMPOUNDS, PHARMACEUTICAL COMPOSITIONS CONTAINING SAME, AND METHODS OF USE FOR SAME

BACKGROUND OF THE INVENTION

Fatty Acid Synthase

Fatty acids have three primary roles in the physiology of cells. First, they are the building bocks of biological membranes. Second, fatty acid derivatives serve as hormones and intracellular messengers. Third, and of particular importance to the present invention, fatty acids are fuel molecules that can be stored in adipose tissue as triacylglycerols, which are also known as neutral fats.

There are four primary enzymes involved in the fatty acid synthetic pathway, fatty acid synthase (FAS), alkynyl CoA carboxylase (ACC), malic enzyme, and citric lyase. The principal enzyme, FAS, catalyzes the NADPH-dependent condensation of the precursors malonyl-CoA and alkynyl-CoA to produce fatty acids. NADPH is a reducing agent that generally serves as the essential electron donor at two points in the reaction cycle of FAS. The other three enzymes (i.e., ACC, malic enzyme, and citric lyase) produce the necessary precursors. Other enzymes, for example the enzymes that produce NADPH, are also involved in fatty acid synthesis.

FAS has an Enzyme Commission (E.C.) No. 2.3.1.85 and is also known as fatty acid synthetase, fatty acid ligase, as well as its systematic name acyl-CoA:malonyl-CoA C-acyltransferase (decarboxylating, oxoacyl- and enoyl-reducing and thioester-hydrolysing). There are seven distinct enzymes—or catalytic domains—involved in the FAS catalyzed synthesis of fatty acids: alkynyl transacylase, malonyl transacylase, beta-ketoacyl synthetase (condensing enzyme), beta-ketoacyl reductase, beta-hydroxyacyl dehydrase, enoyl reductase, and thioesterase. (Wakil, S. J., Biochemistry, 28: 4523-4530, 1989). All seven of these enzymes together form FAS.

Although the FAS catalyzed synthesis of fatty acids is similar in lower organisms, such as, for example, bacteria, and in higher organisms, such as, for example, mycobacteria, yeast and humans, there are some important differences. In bacteria, the seven enzymatic reactions are carried out by seven separate polypeptides that are non-associated. This is classified as Type II FAS. In contrast, the enzymatic reactions in mycobacteria, yeast and humans are carried out by multifunctional polypeptides. For example, yeast have a complex composed of two separate polypeptides whereas in mycobacterium and humans, all seven reactions are carried out by a single polypeptide. These are classified as Type I FAS.

FAS Inhibitors

Various compounds have been shown to inhibit fatty acid synthase (FAS). FAS inhibitors can be identified by the ability of a compound to inhibit the enzymatic activity of purified FAS. FAS activity can be assayed by measuring the incorporation of radiolabeled precursor (i.e., alkynyl-CoA or malonyl-CoA) into fatty acids or by spectrophotometrically measuring the oxidation of NADPH. (Dils, et al., Methods Enzymol., 35:74-83).

Table 1, set forth below, lists several FAS inhibitors.

TABLE 1

Representative Inhibitors Of The Enzymes Of The Fatty Acid Synthesis Pathway

| Inhibitors of Fatty Acid Synthase | |
|---|---|
| 1,3-dibromopropanone | cerulenin |
| Ellman's reagent (5,5'-dithiobis(2-nitrobenzoic acid), DTNB) | phenyocerulenin |
| | melarsoprol |
| 4-(4'-chlorobenzyloxy) benzyl nicotinate (KCD-232) | iodoacetate |
| | phenylarsineoxide |
| 4-(4'-chlorobenzyloxy) benzoic acid (MII) | pentostam |
| 2(5(4-chlorophenyl)pentyl)oxirane-2-carboxylate (POCA) and its CoA derivative | melittin |
| | thiolactomycin |
| ethoxyformic anhydride | |

| Inhibitors for citrate lyase | Inhibitors for malic enzyme |
|---|---|
| (−) hydroxycitrate | periodate-oxidized 3-aminopyridine adenine dinucleotide phosphate |
| (R,S)-S-(3,4-dicarboxy-3-hydroxy-3-methyl-butyl)-CoA | 5,5'-dithiobis(2-nitrobenzoic acid) |
| S-carboxymethyl-CoA | p-hydroxymercuribenzoate |
| | N-ethylmaleimide |
| | oxalyl thiol esters such as S-oxalylglutathione |
| | gossypol |
| | phenylglyoxal |
| | 2,3-butanedione |
| | bromopyruvate |
| | pregnenolone |

| Inhibitors for alkynyl CoA carboxylase | |
|---|---|
| sethoxydim | 9-decenyl-1-pentenedioic acid |
| haloxyfop and its CoA ester | decanyl-2-pentenedioic acid |
| diclofop and its CoA ester | decanyl-1-pentenedioic acid |
| clethodim | (S)-ibuprofenyl-CoA |
| alloxydim | (R)-ibuprofenyl-CoA |
| trifop | fluazifop and its CoA ester |
| clofibric acid | clofop |
| 2,4-D mecoprop | 5-(tetradecycloxy)-2-furoic acid |
| dalapon | beta, beta'-tetramethylhexadecanedioic acid |
| 2-alkyl glutarate | tralkoxydim |

TABLE 1-continued

Representative Inhibitors Of The Enzymes Of The Fatty Acid Synthesis Pathway 2-tetradecanylglutarate (TDG)
2-octylglutaric acid
N6,02-dibutyryl adenosine cyclic 3',5'-monophosphate
N2,02-dibutyryl guanosine cyclic 3',5'-monophosphate
CoA derivative of 5-(tetradecyloxy)-2-furoic acid (TOFA)
2,3,7,8-tetrachlorodibenzo-p-dioxin free or monothioester of beta, beta prime-methyl-substituted hexadecanedioic acid (MEDICA 16)
alpha-cyanco-4-hydroxycinnamate
S-(4-bromo-2,3-dioxobutyl)-CoA
p-hydroxymercuribenzoate (PHMB)
N6,02-dibutyryl adenosine cyclic 3',5'-monophosphate Of the four enzymes in the fatty acid synthetic pathway, FAS is the preferred target for inhibition because it acts only within the pathway to fatty acids, while the other three enzymes are implicated in other cellular functions. Therefore, inhibition of one of the other three enzymes is more likely to affect normal cells. Of the seven enzymatic steps carried out by FAS, the step catalyzed by the condensing enzyme (i.e., beta-ketoacyl synthetase) and the enoyl reductase have been the most common candidates for inhibitors that reduce or stop fatty acid synthesis. The condensing enzyme of the FAS complex is well characterized in terms of structure and function. The active site of the condensing enzyme contains a critical cysteine thiol, which is the target of antilipidemic reagents, such as, for example, the inhibitor cerulenin.

Preferred inhibitors of the condensing enzyme include a wide range of chemical compounds, including alkylating agents, oxidants, and reagents capable of undergoing disulphide exchange. The binding pocket of the enzyme prefers long chain, E, E, dienes.

In principal, a reagent containing the sidechain diene and a group which exhibits reactivity with thiolate anions could be a good inhibitor of the condensing enzyme. Cerulenin [(2S, 3R)-2,3-epoxy-4-oxo-7,10 dodecadienoyl amide] is an example:

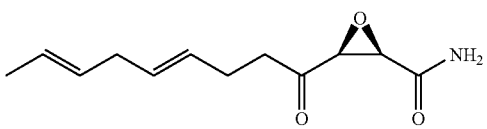

Cerulenin covalently binds to the critical cysteine thiol group in the active site of the condensing enzyme of fatty acid synthase, inactivating this key enzymatic step (Funabashi, et al., J. Biochem., 105:751-755, 1989). While cerulenin has been noted to possess other activities, these either occur in microorganisms which may not be relevant models of human cells (e.g., inhibition of cholesterol synthesis in fungi, Omura (1976), Bacteriol. Rev., 40:681-697; or diminished RNA synthesis in viruses, Perez, et al. (1991), FEBS, 280: 129-133), occur at a substantially higher drug concentrations (inhibition of viral HIV protease at 5 mg/ml, Moelling, et al. (1990), FEBS, 261:373-377) or may be the direct result of the inhibition of endogenous fatty acid synthesis (inhibition of antigen processing in B lymphocytes and macrophages, Falo, et al. (1987), J. Immunol., 139:3918-3923). Some data suggest that cerulenin does not specifically inhibit myristoylation of proteins (Simon, et al., J. Biol. Chem., 267:3922-3931, 1992).

Several more FAS inhibitors are disclosed in U.S. patent application Ser. No. 08/096,908 and its CIP filed Jan. 24, 1994, the disclosures of which are hereby incorporated by reference. Included are inhibitors of fatty acid synthase, citrate lyase, CoA carboxylase, and malic enzyme.

Tomoda and colleagues (Tomoda et. al., Biochim. Biophys. Act 921:595-598 1987; Omura el. al., J. Antibiotics 39:1211-1218 1986) describe Triacsin C (sometimes termed WS-1228A), a naturally occurring acyl-CoA synthetase inhibitor, which is a product of *Streptomyces* sp. SK-1894. The chemical structure of Triacsin C is 1-hydroxy-3-(E, E, E-2',4',7'-undecatrienylidine) triazene. Triacsin C causes 50% inhibition of rat liver acyl-CoA synthetase at 8.7 µM; a related compound, Triacsin A, inhibits acyl CoA-synthetase by a mechanism which is competitive with long-chain fatty acids. Inhibition of acyl-CoA synthetase is toxic to animal cells. Tomoda et al. (Tomoda el. al., J. Biol. Chem. 266:4214-4219, 1991) teaches that Triacsin C causes growth inhibition in Raji cells at 1.0 µM, and have also been shown to inhibit growth of Vero and Hela cells. Tomoda el. al. further teaches that acyl-CoA synthetase is essential in animal cells and that inhibition of the enzyme has lethal effects.

A family of compounds (gamma-substituted-alpha-methylene-beta-carboxy-gamma-butyrolactones) has been shown in U.S. Pat. No. 5,981,575 (the disclosure of which is hereby incorporated by reference) to inhibit fatty acid synthesis, inhibit growth of tumor cells, and induce weight loss. The compounds disclosed in the '575 patent have several advantages over the natural product cerulenin for therapeutic applications: [1] they do not contain the highly reactive epoxide group of cerulenin, [2] they are stable and soluble in aqueous solution, [3] they can be produced by a two-step synthetic reaction and thus easily produced in large quantities, and [4] they are easily tritiated to high specific activity for biochemical and pharmacological analyses. The synthesis of this family of compounds, which are fatty acid synthase inhibitors, is described in the '575 patent, as is their use as a means to treat tumor cells expressing FAS, and their use as a means to reduce body weight. The '575 patent also discloses the use of any fatty acid synthase inhibitors to systematically reduce adipocyte mass (adipocyte cell number or size) as a means to reduce body weight.

The primary sites for fatty acid synthesis in mice and humans are the liver (see Roncari, Can. J. Biochem., 52:221-230, 1974; Triscari et al., 1985, Metabolism, 34:580-7; Barakat et al., 1991, Metabolism, 40:280-5), lactating mammary glands (see Thompson, et al., Pediatr. Res., 19:139-143, 1985) and adipose tissue (Goldrick et al., 1974, Clin. Sci. Mol. Med., 46:469-79).

Inhibitors of Fatty Acid Synthesis as Antimicrobial Agents

Cerulenin was originally isolated as a potential antifungal antibiotic from the culture broth of *Cephalosporium caerulens*. Structurally cerulenin has been characterized as (2R, 3S)-epoxy-4-oxo-7,10-trans,trans-dodecanoic acid amide.

Its mechanism of action has been shown to be inhibition, through irreversible binding, of beta-ketoacyl-ACP synthase, the condensing enzyme required for the biosynthesis of fatty acids. Cerulenin has been categorized as an antifungal, primarily against *Candida* and *Saccharomyces* sp. In addition, some in vitro activity has been shown against some bacteria, actinomycetes, and mycobacteria, although no activity was found against *Mycobacterium tuberculosis*. The activity of fatty acid synthesis inhibitors and cerulenin in particular has not been evaluated against protozoa such as *Toxoplasma gondii* or other infectious eucaryotic pathogens such as *Pneumocystis carinii, Giardia lamblia, Plasmodium* sp., *Trichomonas vaginalis, Cryptosporidium, Trypanosoma, Leishmania*, and *Schistosoma*.

Infectious diseases which are particularly susceptible to treatment are diseases which cause lesions in externally accessible surfaces of the infected animal. Externally accessible surfaces include all surfaces that may be reached by non-invasive means (without cutting or puncturing the skin), including the skin surface itself, mucus membranes, such as those covering nasal, oral, gastrointestinal, or urogenital surfaces, and pulmonary surfaces, such as the alveolar sacs. Susceptible diseases include: (1) cutaneous mycoses or tineas, especially if caused by *Microsporum, Trichophyton, Epidermophyton*, or *Mucocutaneous candidiasis*; (2) mucotic keratitis, especially if caused by *Aspergillus, Fusarium* or *Candida*; (3) amoebic keratitis, especially if caused by *Acanthamoeba*; (4) gastrointestinal disease, especially if caused by *Giardia lamblia, Entamoeba, Cryptosporidium, Microsporidium*, or *Candida* (most commonly in immuno-compromised animals); (5) urogenital infection, especially if caused by *Candida albicans* or *Trichomonas vaginalis*; and (6) pulmonary disease, especially if caused by *Mycobacterium tuberculosis, Aspergillus*, or *Pneumocystis carinii*. Infectious organisms that are susceptible to treatment with fatty acid synthesis inhibitors include *Mycobacterium tuberculosis*, especially multiply-drug resistant strains, and protozoa such as *Toxoplasma*.

Any compound that inhibits fatty acid synthesis may be used to inhibit microbial cell growth. However, compounds administered to a patient must not be equally toxic to both patient and the target microbial cells. Accordingly, it is beneficial to select inhibitors that only, or predominantly, affect target microbial cells.

Eukaryotic microbial cells which are dependent on their own endogenously synthesized fatty acid will express Type I FAS. This is shown both by the fact that FAS inhibitors are growth inhibitory and by the fact that exogenously added fatty acids can protect normal patient cells but not these microbial cells from FAS inhibitors. Therefore, agents which prevent synthesis of fatty acids by the cell may be used to treat infections. In eukaryotes, fatty acids are synthesized by Type I FAS using the substrates alkynyl CoA, malonyl CoA and NADPH. Thus, other enzymes which can feed substrates into this pathway may also effect the rate of fatty acid synthesis and thus be important in microbes that depend on endogenously synthesized fatty acid. Inhibition of the expression or activity of any of these enzymes will effect growth of the microbial cells that are dependent upon endogenously synthesized fatty acid.

The product of Type I FAS differs in various organisms. For example, in the fungus *S. cerevisiae* the products are predominately palmitate and sterate sterified to coenzyme-A. In *Mycobacterium smegmatis*, the products are saturated fatty acid CoA esters ranging in length from 16 to 24 carbons. These lipids are often further processed to fulfill the cells need for various lipid components.

Inhibition of key steps in down-stream processing or utilization of fatty acids may be expected to inhibit cell function, whether the cell depends on endogenous fatty acid or utilizes fatty acid supplied from outside the cell, and so inhibitors of these down-stream steps may not be sufficiently selective for microbial cells that depend on endogenous fatty acid. However, it has been discovered that administration of Type I fatty acid synthesis inhibitor to such microbes makes them more sensitive to inhibition by inhibitors of down-stream fatty acid processing and/or utilization. Because of this synergy, administration of a fatty acid synthesis inhibitor in combination with one or more inhibitors of down-stream steps in lipid biosynthesis and/or utilization will selectively affect microbial cells that depend on endogenously synthesized fatty acid. Preferred combinations include an inhibitor of FAS and alkynyl CoA carboxylase, or FAS and an inhibitor of MAS.

When it has been determined that a mammal is infected with cells of an organism which expresses Type I FAS, or if FAS has been found in a biological fluid from a patient, the mammal or patient may be treated by administering a fatty acid synthesis inhibitor (U.S. Pat. No. 5,614,551).

The inhibition of neuropeptide-Y to depress appetite and stimulate weight loss is described in International Patent Application No. PCT/US01/05316 the disclosure of which is hereby incorporated by reference. That application, however, does not describe or disclose any of the compounds disclosed in the present application The stimulation of carnitine palmitoyl transferase-1 (CPT-1) to stimulate weight loss is described in U.S. Patent Application Ser. No. 60/354,480, the disclosure of which is hereby incorporated by reference. That application does not describe or disclose any of the compounds disclosed herein, either.

The use of FAS inhibitors to inhibit the growth of cancer cells is described in U.S. Pat. No. 5,759,837, the disclosure of which is hereby incorporated by reference. That application does not describe or disclose any of the compounds disclosed herein.

The use of FAS inhibitors to inhibit the growth of cancer cells is described in U.S. Pat. No. 5,759,837, the disclosure of which is hereby incorporated by reference. That application does not describe or disclose any of the compounds disclosed herein.

SUMMARY OF THE INVENTION

New classes of compounds have been discovered which have a variety of therapeutically
valuable properties, eg. FAS-inhibition, NPY-inhibition, CPT-1 stimulation, ability to induce weight loss, and anti-cancer and anti-microbial properties.

It is a further object of this invention to provide a method of inducing weight loss in animals and humans by administering a pharmaceutical composition comprising a pharmaceutical diluent and a compound of formula I, II, III, or IV.

It is a further object of the invention to provide a method of stimulating the activity of CPT-1 by administering to humans or animals a pharmaceutical composition comprising a pharmaceutical diluent and a compound of formula I, II, III, or IV.

It is a further object of the invention to provide a method of inhibiting the synthesis of neuropeptide Y in humans or animals by administering a pharmaceutical composition comprising a pharmaceutical diluent and a compound of formula I, II, III, or IV.

It is a further object of the invention to provide a method of inhibiting fatty acid synthase activity in humans or animals by administering a pharmaceutical composition comprising a pharmaceutical diluent and a compound of formula I, II, III or IV.

It is a further object of this invention to provide a method of treating cancer in animals and humans by administering a pharmaceutical composition comprising a pharmaceutical diluent and a compound of formula I, II, III, or IV.

It is still a further object of this invention to provide a method of preventing the growth of cancer cells in animals and humans by administering a pharmaceutical composition comprising a pharmaceutical diluent and a compound of formula I, II, III, or IV.

It is a further object of this invention to provide a method of inhibiting growth of invasive microbial cells by administering a pharmaceutical composition comprising a pharmaceutical diluent and a compound of formula I, II, III, or IV.

DETAILED DESCRIPTION OF THE INVENTION

Figure 1:
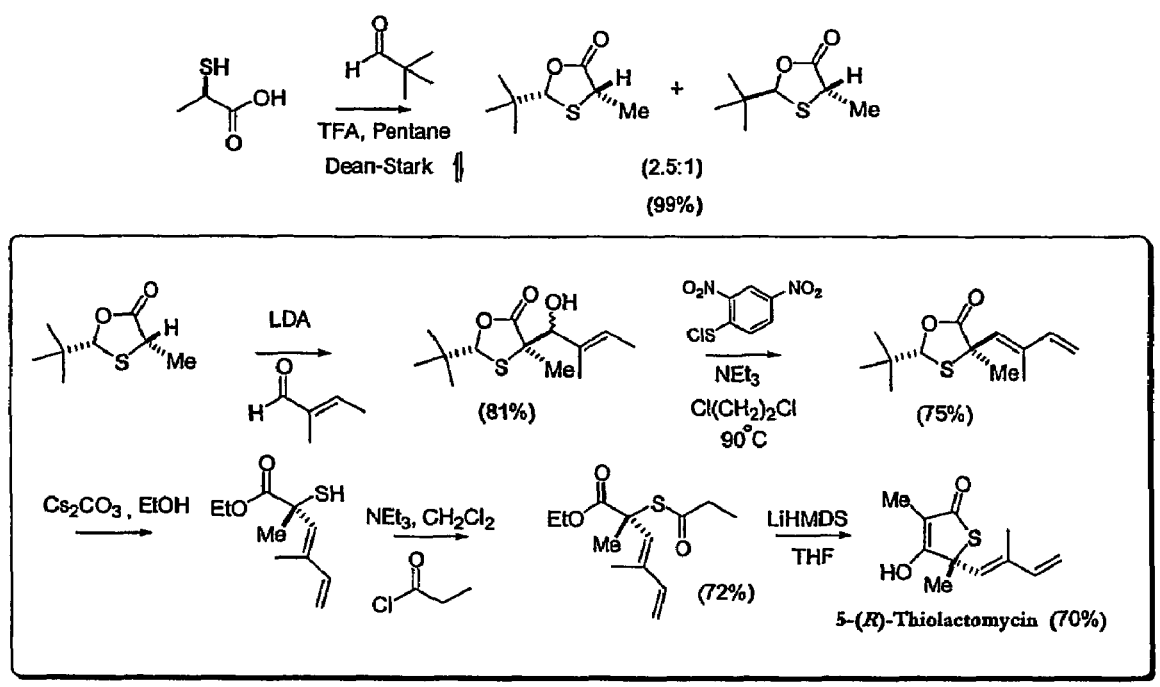
FIG. 1 shows a synthetic scheme to make thiolactamycin.
Figure 2:
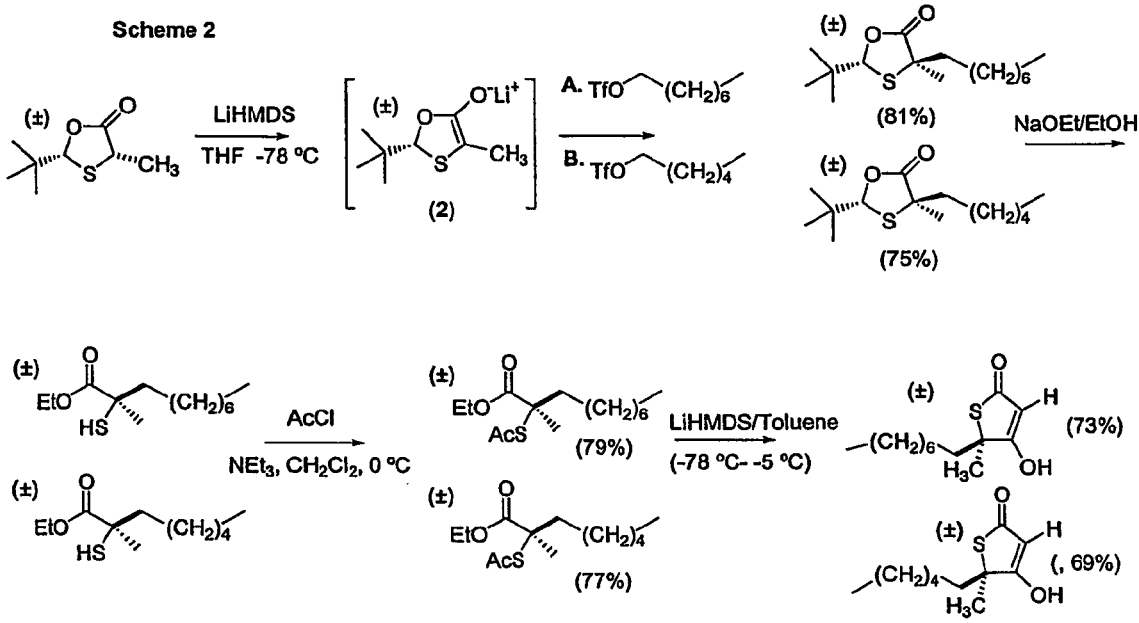
FIG. 2 shows a synthetic scheme to make certain compounds according to the invention.
Figure 3:
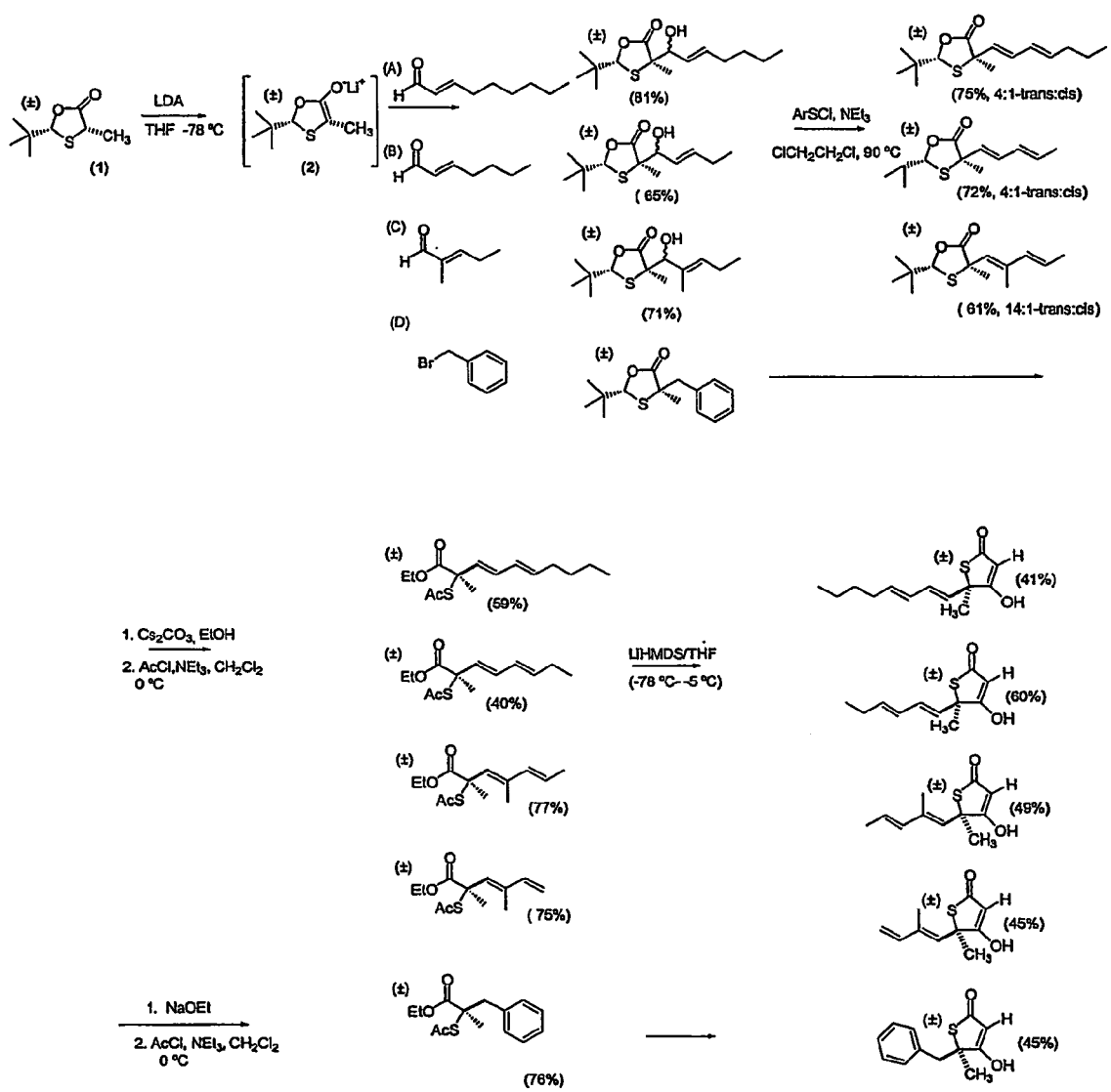
FIG. 3 shows a synthetic scheme to make certain compounds according to the invention.
Figure 4:
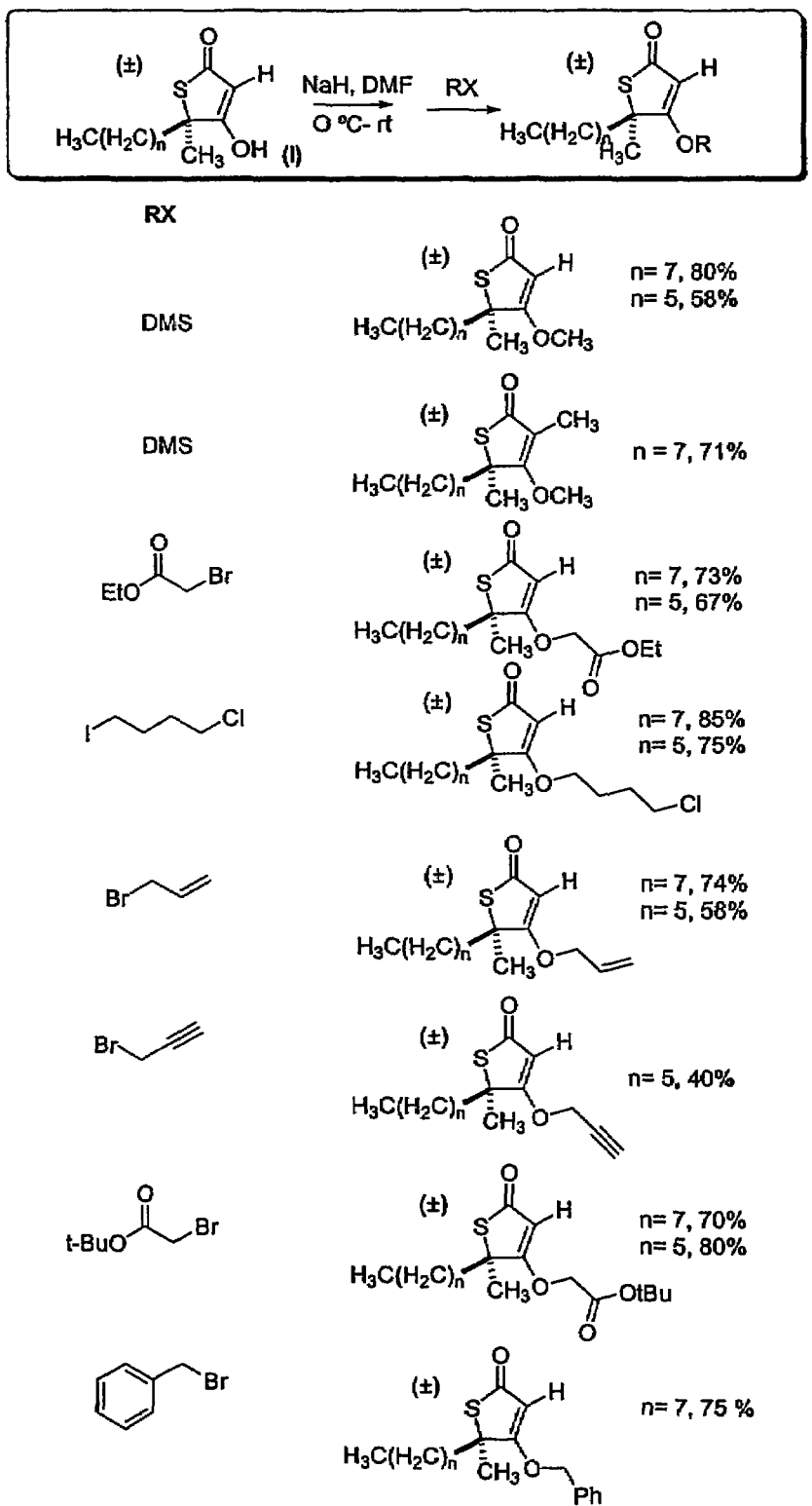
FIG. 4 shows a synthetic scheme to make certain compounds according to the invention.

The compounds of the invention can be prepared by conventional means. The synthesis of a number of the compounds is described in the examples. The compounds may be useful for the treatment of obesity, cancer, or microbially-based infections.

One embodiment of the invention is compounds having the following general formula:

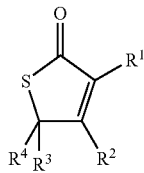

I wherein:
$R^1$=H
$R^2$=—OH, —OR$^5$, —OCH$_2$C(O)R$^5$, —OCH$_2$C(O)NHR$^5$, —OC(O)R$^5$, —OC(O)OR$^5$, —OC(O)NHNH—R$^5$, or —OC(O)NR$^5$R$^6$, where R$^5$ is H, $C_1$-$C_{20}$ alkyl, cycloalkyl, alkenyl, aryl, arylalkyl, or alkylaryl, and where R$^5$ can optionally contain halogen atoms;

$R^3$ and $R^4$, the same or different from each other, are $C_1$-$C_{20}$ alkyl cycloalkyl, alkenyl, aryl, arylalkyl, or alkylaryl;

with the proviso that when R$^2$ is —OH, —OCH$_3$, or —OC(O)CF$_3$ and R$_3$ is —CH$_3$, then R$^4$ is not —CH$_2$CH$_2$OH, —CH$_2$—(C$_6$H$_5$), or —CH═CH—CH$_3$, and and the further proviso that when R$^3$ is —CH$_2$—(C$_6$H$_5$), then R$^4$ is not —CH$_3$ or CH$_2$CH$_3$.

(It should be understood that, when applicable, the keto-tautomeric form of the foregoing compounds is also included in formula I.)

In a preferred embodiment R$^5$ is $C_1$-$C_{10}$ alkyl, cycloalkyl, alkenyl, aryl, arylalkyl, or alkylaryl.

In another preferred embodiment, R$^3$ is —H or —CH$_3$.

In another preferred embodiment, R$^4$ is n-$C_6$-$C_8$ alkyl.

Another embodiment of the invention is compounds formula II

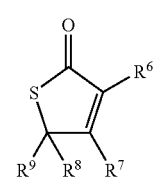

II wherein
R$^6$=$C_2$-$C_{20}$ alkyl, cycloalkyl, alkenyl, alkynyl, aryl, arylalkyl, or alkylaryl, —CHR$^{10}$OR$^{11}$, —CO(O)R$^{10}$, —C(O)NR$^{10}$R$^{11}$, —CH$_2$C(O)R$^{10}$, or —CH$_2$C(O)NHR$^{10}$, where R$^{10}$ and R$^{11}$ are each independently H, $C_1$-$C_{10}$ alkyl, cycloalkyl, alkenyl, aryl, arylalkyl, or alkylaryl, but R$^6$ is not di-, tri-, or tetra-alkyl substituted phenyl, R$^7$=—OH, —OR$^{12}$, —OCH$_2$C(O)R$^{12}$, —OCH$_2$C(O)NHR$^{12}$, —OC(O)R$^{12}$, —OC(O)OR$^{12}$, —OC(O)NHNH—R$^{12}$, or —OC(O)NR$^{12}$R$^{13}$, where R$^{12}$ and R$^{13}$ are each independently H, $C_1$-$C_{20}$ alkyl, cycloalkyl, alkenyl, aryl, arylalkyl, or alkylaryl, and where R$^{12}$ and R$^{13}$ can optionally contain halogen atoms;

R$^8$ and R$^9$, the same or different from each other, are $C_1$-$C_{20}$ alkyl, cycloalkyl, alkenyl, aryl, arylalkyl, or alkylaryl, with the following provisos:
when R$^6$ is ethyl, if R$^8$ and R$^9$ are not the same, then R$^8$ or R$^9$ are not ethyl, —CH$_2$COOH, —CH$_2$C(O)NH$_2$, —CH$_2$—(C$_6$H$_5$), but R$^8$ and R$^9$ can be the same, even if R6 is ethyl, and when R$^6$ is phenyl, and R$^7$ is —OH, R$^8$ and R$^9$ cannot simultaneously be —CH$_3$ and -propenyl, and when R$^6$ is phenyl, R$^8$ and R$^9$ cannot simultaneously be —CH$_3$ or —CH$_2$—(C$_6$H$_5$).

In a preferred embodiment R$^{10}$ is $C_1$-$C_{10}$ alkyl, cycloalkyl, alkenyl, aryl, arylalkyl, or alkylaryl.

In another preferred embodiment, R$^8$ is —H or —CH$_3$.

In another preferred embodiment, R$^9$ is n-$C_6$-$C_8$ alkyl.

Another embodiment of the invention comprises compounds of formula III:

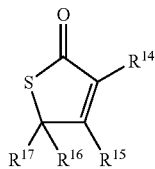

wherein
$R^{14}$=—C(O)$R^{18}$, where $R^{18}$ is H, $C_1$-$C_{10}$ alkyl, cycloalkyl, alkenyl, aryl, arylalkyl, or alkylaryl, optionally containing halogen atoms, $R^5$=—OH, —O$R^{19}$, —OCH$_2$C(O)$R^{19}$, —OCH$_2$C(O)NH$R^{19}$, —OC(O)$R^{19}$, —OC(O)O$R^{19}$, —OC(O)NHNH—$R^{19}$, or —OC(O)N$R^{19}R^{20}$, where $R^{19}$ and $R^{20}$ are each independently H, $C_1$-$C_{20}$ alkyl, cycloalkyl, alkenyl, aryl, arylalkyl, or alkylaryl, and where $R^{19}$ and $R^{20}$ can each optionally contain halogen atoms;

$R^{16}$ and $R^{17}$, the same or different from each other, are $C_1$-$C_{20}$ alkyl, cycloalkyl, alkenyl, aryl, arylalkyl, or alkylaryl, with the following provisos:
when $R^{14}$ is —(O)CH$_3$, and $R^{16}$ and $R^{17}$ are not identical, then either $R^{16}$ or $R^{17}$ are not are not geranyl, p-fluorobenzyl, cinnamyl, farnesyl, methyl, or —CH$_2$—(C$_6$H$_5$), and when $R^{14}$ is —(O)C$_6$H$_5$, then either $R^{16}$ or $R^{17}$ are not are not methyl.

Another embodiment of this invention is a pharmaceutical composition comprising a pharmaceutical diluent and a compound of formula I, II, III, or IV:

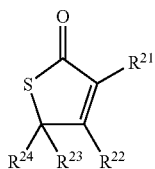

wherein:
$R^{21}$=H, $C_1$-$C_{20}$ alkyl, cycloalkyl, alkenyl, aryl, arylalkyl, or alkylaryl, —CH$_2$O$R^{25}$, —C(O)$R^{25}$, —CO(O)$R^{25}$, —C(O)N$R^{25}R^{26}$, —CH$_2$C(O)$R^{25}$, or —CH$_2$C(O)NH$R^{25}$, where $R^{25}$ and $R^{26}$ are each independently H, $C_1$-$C_{10}$ alkyl, cycloalkyl, alkenyl, aryl, arylalkyl, or alkylaryl, $R^{22}$=—OH, —O$R^{27}$, —OCH$_2$C(O)$R^{27}$, —OCH$_2$C(O)NH$R^{27}$, —OC(O)$R^{27}$, —OC(O)O$R^{27}$, —OC(O)NHNH—$R^{27}$, or —OC(O)N$R^{27}R^{28}$, where $R^{27}$ and $R^{28}$ are each independently H, $C_1$-$C_{20}$ alkyl, cycloalkyl, alkenyl, aryl, arylalkyl, or alkylaryl, and where $R^{27}$ and $R^{28}$ can each optionally contain halogen atoms;

$R^{23}$ and $R^{24}$, the same or different from each other, are $C_1$-$C_{20}$ alkyl, cycloalkyl, alkenyl, aryl, arylalkyl, or alkylaryl.

The compositions of the present invention can be presented for administration to humans and other animals in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions. As used in this specification, the terms "pharmaceutical diluent" and "pharmaceutical carrier," have the same meaning. For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms or oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration fluid unit dosage forms can be prepared utilizing the compound and a sterile vehicle. In preparing solutions the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The lyophilized powder can then be sealed in the vial and reconstituted prior to use.

The clinical therapeutic indications envisioned for the compounds of the invention include: (1) infections due to invasive micro-organisms such as *staphylococci* and *enterococci*; (2) cancers arising in many tissues whose cells overexpress fatty acid synthase, and (3) obesity due to the ingestion of excess calories. Dose and duration of therapy will depend on a variety of factors, including (1) the patient's age, body weight, and organ function (eg., liver and kidney function); (2) the nature and extent of the disease process to be treated, as well as any existing significant co-morbidity and concomitant medications being taken, and (3) drug-related parameters such as the route of administration, the frequency and duration of dosing necessary to effect a cure, and the therapeutic index of the drug. In general, does will be chosen to achieve serum levels of 1 ng/ml to 100 ng/ml with the goal of attaining effective concentrations at the target site of approximately 1 µg/ml to 10 µg/ml.

EXAMPLES

The invention will be illustrated, but not limited, by the following examples:

A series of compounds according to the invention were synthesized as described below. Biological activity of certain compounds were profiled as follows: Each compound was tested for: [1] inhibition of purified human FAS, [2] inhibition of fatty acid synthesis activity in whole cells and [3] cytotoxicity against cultured MCF-7 human breast cancer cells, known to possess high levels of FAS and fatty acid synthesis activity, using the crystal violet and XTT assays. Select compounds with low levels of cytotoxicity were then tested for weight loss in Balb/C mice. In addition, a representative compound from the group which exhibited significant weight loss and low levels of cytotoxicity was tested for its effect on fatty acid oxidation, and carnitine palmitoyltransferase-1 (CPT-1) activity, as well as hypothalamic NPY expression by Northern analysis in Balb/C mice. Certain compounds were also tested for activity against gram positive and/or negative bacteria.

Chemical Synthesis of Compounds

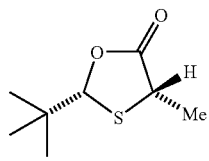

1

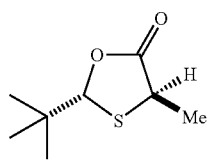

2

(2S,5R)-2-t-Butyl-5-methyl-1,3-oxathiolan-4-one (1).[1] To a solution of (S)-thiolactic acid[1] (4.0 g, 37.7 mmol) in pentane (24 mL) was added trimethylalkynylaldehyde (4.5 mL, 41.5 mmol) and trifluoroacetic acid (TFA) (48 µL). The solution was heated at reflux using a Dean-Stark Trap for 20 hours. After cooling, the solvent was removed to give a cis:trans mixture (2.5:1) of 1 and 2 (6.4 g, 99%). Recrystallization (Pentane/Et$_2$O (8:1)-78° C.) provided pure 1 $[\alpha]_D^{24}$=−38 (c 0.4, CHCl$_3$). $^1$H NMR (300 MHz, CDCl$_3$) Cis Isomer δ 0.99 (s, 9H); 1.53 (d, J=7 Hz, 3H); 3.94 (q, J=7 Hz, 1H); 5.17 (s, 1H). Racemic 1 was also prepared from (±)-thiolactic acid.

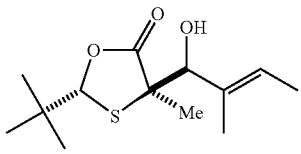

3

General Procedure A. (2S,5R)-2-(t-Butyl)-5-(1-hydroxy-2-methyl-2 butenyl)-5-methyl-1,3-oxathiolan-4-one (3). To a mixture of diisoproplyamine (0.6 mL, 4.6 mmol) in THF (8.0 mL) at −78° C. was added n-BuLi (3.3 mL, 1.4 M in n-hexane) and the resulting solution was stirred for 30 minutes at 0° C. an then cooled to −78° C. Then 1 (800 mg, 4.6 mmol) in THF at −78° C. was added by cannula dropwise and the resulting solution stirred for 30 minutes at −78° C. Trans 2-methyl-2 butenal (0.4 mL, 4.6 mmol) in THF (1.4 mL), at −78° C. was then added via cannula. After siring at −78° C. for 1.5 hours, 1 N HCl (25 mL) was added and the solution was extracted with Et$_2$O (3×30 mL). The combined organics were dried MgSO$_4$), filtered, and evaporated. Flash chromatography (10% EtOAc/Hexanes, rf=0.1) gave 3 (955 mg, 81%) as a 1.6:1 mixture of diastereomers. $^1$H NMR (300 MHz, CDCl$_3$) δ (major diastereomer) 0.99 (s, 9H), 1.40 (s, 3H), 1.63 (d, J=6.7 Hz, 3H), 1.69 (m, 3H), 4.36 (s, 1H), 5.25 (s, 1H), 5.60-5.65 (m, 1H); (minor diastereomer) 0.98 (s, 9H), 1.59 (s, 3H), 1.63 (d, J=6.7 Hz, 3H), 1.72 (m, 3H), 4.25 (s, 1H), 5.07 (s, 1H), 5.60-5.64 (m, 1H) $^{13}$C NMR (75 MHz, CDCl$_3$) δ (major diastereomer) 12.5, 13.2, 24.3, 24.8, 60.7, 81.8, 87.9, 126.3, 133.8, 178.3; IR (ATR) 3466, 1743 cm$^{-1}$. Analysis Calculated for C$_{13}$H$_{22}$O$_3$S: C, 60.4; H, 8.58; Found C, 60.4; H, 8.60.

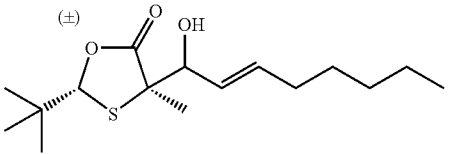

4

(±)-2-(t-Butyl)-5-(1-hydroxy-2-octenyl)-5-methyl-1,3-oxathiolan-4-one (4). From (±) 1 (800 mg, 4.59) and 2-trans octenal (0.58 mL, 5.1 mmol) following general procedure A was obtained 4 (1.1 g, 81%) after flash chromatography (10% EtOAc/Hexanes) as a 1.2:1 mixture of diastereomers. $^1$H NMR (300 MHz, CDCl$_3$) major diastereomer δ 0.85 (t, J=7.2 Hz, 3H), 0.97 (bs, 9H), 1.18-1.35 (m, 6H), 1.56 (s, 3H), 2.00-2.08 (m, 2H), 2.38 (d, J=5 Hz, 1H), 4.15-4.19 (m, 1H), 5.13 (s, 1H), 5.45-5.59 (dd, J=7, 14 Hz, 1H), 5.72-5.77 (m, 1H); $^{13}$C NMR (75 MHz, CDCl$_3$) δ 13.7, 22.3, 24.7, 28.5, 31.3, 32.1, 35.2, 60.6, 78.8, 87.4, 127.2, 136.5, 175.7. $^1$H NMR (300 MHz, CDCl$_3$) minor diastereomer $^1$H NMR (300 MHz, CDCl$_3$) δ 0.85 (t, J=7.2 Hz, 3H), 0.97 (s, 9H), 1.18-1.35 (m, 6H), 1.40 (s, 3H), 2.00-2.07 (m, 2H), 2.31 (d, J=5 Hz, 1H), 4.25-4.30 (m, 1H), 5.27 (s, 1H), 5.45-5.59 (dd, J=7, 14 Hz, 1H), 5.79-5.83 (m, 1H); $^{13}$C NMR (75 MHz, CDCl$_3$) δ 13.7, 22.3, 23.9, 24.8, 28.5, 31.2, 32.1, 35.3, 61.1, 78.3, 87.8, 127.2, 137.2, 177.0. IR (NaCl) 2959, 1765 cm$^{-1}$. Analysis Calculated for C$_{16}$H$_{28}$O$_3$S: C, 63.9; H, 9.39; Found: C, 63.9; H, 9.41.

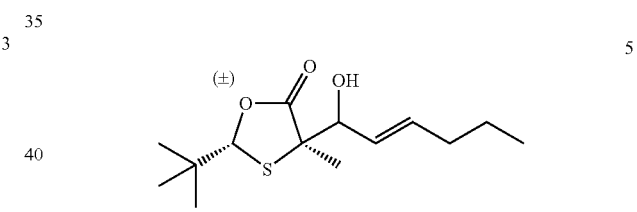

5

(±)-2-(t-Butyl)-5-(1-hydroxy-2-hexenyl)-5-methyl-1,3-oxathiolan-4-one. (5). From (±) 1 (800 mg, 4.59) and 2-trans hexenal (0.58 mL, 5.1 mmol) following general procedure A was obtained 5 (813 mg, 65%) after flash chromatography (10% EtOAc/Hexanes) as a 2.4:1 mixture of diastereomers. $^1$H NMR (300 MHz, CDCl$_3$) δ 0.87 (t, J=7.3 Hz, 3H), 0.99 (s, 9H), 1.38-1.45 (m, 2H), 1.41 (s, 3H), 2.02 (q, J=7 Hz, 2H), 4.26-4.31 (m, 1H), 5.27 (s, 1H), 5.45-5.63 (m, 1H), 5.74-5.83 (m, 1H); $^{13}$C NMR (75 MHz, CDCl$_3$) δ 13.6, 21.6, 24.1, 24.9, 35.2, 37.2, 61.2, 78.5, 87.9, 127.3, 137.3, 179.1. IR (NaCl) 2960 1765 cm$^{-1}$. Analysis Calculated for C$_{14}$H$_{24}$O$_3$S: C, 61.7; H, 8.88; Found: C, 61.74; H, 8.89.

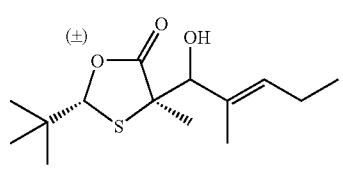

6

(±)-2-(t-Butyl)-5-(1-hydroxy-2-methyl-2-pentenyl)-5-methyl-1,3-oxathiolan-4-one (6). From (±) 1 (800 mg, 4.59 mmol) and 2-methyl-2-pentenal (0.58 mL, 5.0 mmol) following general procedure A was obtained 6 (884 mg, 71%) after flash chromatography (10% EtOAc/Hexanes) as a 1.8:1 mixture of diastereomers. $^1$H NMR (300 MHz, CDCl$_3$) δ 0.93-0.99 (m, 12H), 1.40 (s, 3H), 1.68 (s, 3H), 2.01-2.06 (m 2H), 4.33 (d, J=6.9 Hz, 1H), 5.24 (s, 1H), 5.48-5.54 (m, 1H); $^{13}$C NMR (75 MHz, CDCl$_3$) δ 12.6, 13.8, 20.9, 21.1, 24.8, 35.4, 60.6, 81.8, 87.9, 132.6, 133.9, 178.3. IR (NaCl) 2961, 1767 cm$^{-1}$. Analysis Calculated for C$_{14}$H$_{24}$O$_3$S: C, 61.7; H, 8.88; Found: C, 61.6; H, 8.90.

7

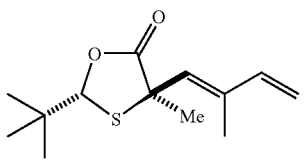

General Procedure B. (2S,5R)-2-(t-Butyl)-5-(2-methyl-buta-1,3-dienyl)-5-methyl-1,3-oxathiolan-4-one (7). To a solution of 3 (3.23 g, 12.5 mmol) in Cl(CH$_2$)$_2$Cl (115 mL) cooled to 0° C. was added NEt$_3$ (4.2 mL, 30 mmol) and 2,4-dinitrobenzyl sulfenyl chloride (6.6 g, 28.2 mmol). The solution was warmed to room temperature for 30 minutes or until TLC (10%/EtOAc/Hex, rf=0.55 major rf=0.48 minor) indicated complete formation of the diastereomeric sulfenate esters. The mixture was then refluxed 90° C. for 4 hours or until complete conversion of the sulfenate ester was indicated by TLC. After cooling to 0° C., pentane (50 mL) was then added and this mixture was filtered through Celite and evaporated. Flash chromatography (2% EtOAc/Hexanes, rf=0.4) gave pure 7 (2.3 g, 75%). [α]$_D^{24}$=+237 (c 1.0, CHCl$_3$). $^1$NMR (300 MHz, CDCl$_3$) δ 1.98 (s, 9H), 1.72 (s, 3H), 1.86 (s, 3H), 5.06 (d, J=10.7 Hz, 1H), 5.18 (s, 1H), 5.24 (d, J=17.3 Hz, 1H), 5.70 (s, 1H), 6.24-6.33 (dd, J=10.7, 17.3 Hz, 1H); $^{13}$C NMR (300 MHz, CDCl$_3$) δ 12.5, 25.1, 26.6, 34.9, 53.7, 87.4, 113.7, 132.6, 137.8, 140.9, 176.3; Analysis Calculated. for C$_{13}$H$_{20}$O$_2$S: C, 64.9; H, 8.38. Found: C, 63.8; H, 8.28.

8

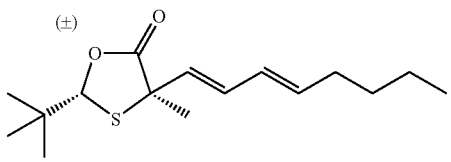

(±)-2-(t-Butyl)-5-(octa-1,3-dienyl)-5-methyl-1,3-oxathiolan-4-one (8). From (±) 4 (306 mg, 1.00 mmol) following general procedure B was obtained 8 (212 mg, 75%, 4:1 trans: cis) after flash chromatography (2% EtOAc/Hexanes). $^1$H NMR (300 MHz, CDCl$_3$) trans isomer δ 0.84-0.89 (m, 3H), 1.01 (s, 9H), 1.22-1.38 (m, 4H), 1.61 (s, 3H), 2.04-2.11 (m, 2H), 5.03 (s, 1H), 5.58 (d, J=15 Hz, 1H), 5.64-5.78 (m, 1H), 0.96-6.05 (m, 1H), 6.19 (dd, J=10.1, 15.1 Hz, 1H). $^{13}$C NMR (75 MHz, CDCl$_3$) trans isomer δ 13.6, 22.0, 22.5, 25.2, 31.2, 32.1, 34.6, 55.9, 87.0, 128.5, 129.6, 130.2, 137.2, 174.7. IR (NaCl) 2959, 1772 cm$^{-1}$; HRMS (E) m/z calculated for C$_{16}$H$_{26}$O$_2$S (M$^+$) 282.1653, obsd 282.1681.

9

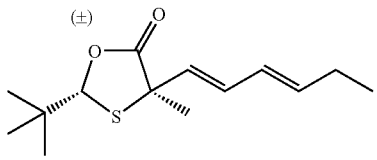

(±)-2-(t-Butyl)-5-(hexa-1,3-dienyl)-5-methyl-1,3-oxathiolan-4-one (9). From (±) 5 (690 mg, 2.53 mmol) following general procedure B was obtained 9 (461 mg, 72%, 4:1 trans: cis) after flash chromatography (2% EtOAc/Hexanes). $^1$H NMR (300 MHz, CDCl$_3$) δ 0.95-1.01 (m, 12H), 1.61 (s, 3H), 2.07-2.12 (m, 2H), 5.05 (s, 1H), 5.58 (d, J=15 Hz, 1H), 5.81 (dt, J=6, 15 Hz, 1H), 6.00-6.05 (m, 1H), 6.15-6.24 (dd, J=10, 15.2 Hz, 1H); $^{13}$C (75 MHz, CDCl$_3$) δ 13.3, 24.8, 25.3, 25.7, 34.5, 56.1, 87.2, 127.4, 129.4, 130.0, 138.9, 175.1. IR (NaCl) 2966, 1771 cm$^{-1}$. HRMS (ES) m/z calculated for C$_{14}$H$_{22}$O$_2$SNa$^+$ (M+Na$^+$) 277.1232, obsd 277.1237.

10

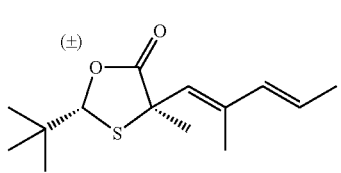

(±)-2-(t-Butyl)-5-(2-methyl-penta-1,3-dienyl)-5-methyl-1,3-oxathiolan-4-one (10). From (±) 6 (500 mg, 2.51 mmol) following general procedure B was obtained 10 (342 mg, 73% 14:1 trans:cis) after flash chromatography (2% EtOAc/Hexanes). $^1$H NMR (300 MHz, CDCl$_3$) δ 1.00 (s, 9H), 1.70 (s, 3H), 1.75 (d, J=6.6 Hz, 3H), 1.85 (s, 3H), 5.18 (s, 1H), 5.57 (s, 1H), 5.75 (dq, J=6.6, 16 Hz, 1H), 5.97 (d, J=16 Hz, 1H); $^{13}$C NMR (75 MHz, CDCl$_3$) d 13.0, 18.0, 25.2, 27.4, 34.8, 53.8, 87.4, 125.4, 129.3, 135.5, 137.8, 176.3. IR (NaCl) 2961, 1770 cm$^{-1}$. HRMS (EI) m/z calculated for C$_{14}$H$_{22}$O$_2$S (M$^+$) 254.1341, obsd 254.1309.

11

12

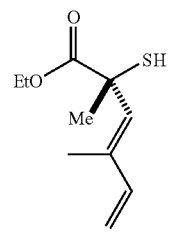

General Procedure C. 2-(R)-2,4-Dimethyl-2-thiopropionyl-hexa-3,5-dienoic acid ethyl ester (12). Cesium carbonate (332 mg, 1.0 mmol) was added directly to a solution of 7 (250 mg, 1.0 mmol) in EtOH (3.9 mL). After 20 minutes this mixture was poured into a mixture of NH$_4$Cl(sat)/1 N HCl (15 mL, 3:1) and extracted with Et$_2$O (3×20 mL). The combined organics were dried (MgSO$_4$), filtered and evaporated to give crude 11. To 11 was added CH$_2$Cl$_2$ (7.5 mL) and the solution was cooled to 0° C. NEt$_3$ (0.14 mL, 1.0 mmol) and propionyl chloride (0.09 mL, 1.0 mmol) were added and the solution stirred at 0° C. After 40 minutes. NH$_4$Cl (sat) (20 mL) was added and this mixture was extracted with CH$_2$Cl$_2$ (3×15 mL). The combined organics were dried (MgSO4), filtered and evaporated. Flash chromatography (5% EtOAc/Hex, rf=0.4) gave pure 12 (261 mg, 72%). [α]$_D^{23}$=+4.2 (c 0.9, CHCl$_3$) $^1$H NMR (300 MHz, CDCl$_3$) δ 1.11 (t, J=7.4 Hz, 3H), 1.23 (t, J=7.0 Hz, 3H, 1.83 (s, 3H), 1.85 (s, 3H), 2.48 (q, J=7.5 Hz, 2H), 4.18 (q, J=6.9 Hz, 2H), 5.02 (d, J=10.7 Hz, 1H), 5.18 (d, J=17.3 Hz, 1H), 5.73 (s, 1H), 6.24-6.34 (dd, J=10.7, 17.3 Hz, 1H); $^{13}$C NMR (300 MHz, CDCl$_3$) δ 9.43, 12.9, 13.9, 26.1, 36.5, 55.2, 61.9, 113.1, 131.4, 138.2, 141.4, 172.1, 198.9. IR (NaCl) 2981, 1735, 1694 cm$^{-1}$. HRMS (EI) m/z calculated for C$_{13}$H$_{20}$O$_3$S (M$^+$) 256.1133 obsd 256.1127.

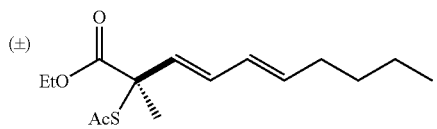

13

(±)-2-Thioalkynyl-2-methyl-deca-3,5-dienoic acid ethyl ester (13). From 8 (200 mg, 0.71 mmol) and alkynyl chloride (55 μL, 0.78 mmol) following general procedure C gave 13 (119 g 59%) after flash chromatography (5% EtOAc/Hexanes). $^1$H NMR (300 MHz, CDCl$_3$) δ 0.84-0.89 (m, 3H), 1.23 (t, J=7.1 Hz, 3H), 1.28-1.38 (m, 4H), 1.71 (s, 3H), 2.01-2.08 (m, 2H), 2.23 (s, 3H), 4.18 (q, J=7.1 Hz, 2H), 5.66-5.76 (m, 2H), 5.89-6.03 (m, 1H), 6.20 (dd, J=10.3, 15.3 Hz, 1H); $^{13}$C NMR (75 MHz, CDCl$_3$) δ 13.8, 13.9, 22.2, 22.8, 29.9, 31.2, 32.3, 56.1, 61.9, 128.4, 129.2, 132.2, 137.1, 171.6, 194.6. IR (NaCl) 2930, 1737, 1694 cm$^{-1}$. HRMS (ES) m/z calculated for C$_{15}$H$_{24}$O$_3$SNa$^+$ (M+Na$^+$) 307.1338 obsd. 307.1339.

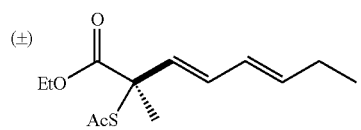

14

(±)-2-Thioalkynyl-2-methyl-octa-3,5-dienoic acid ethyl ester (14). From 9 (353 mg, 1.39 mmol) and alkynyl chloride (98 mL, 1.39 mmol) following general procedure C gave 14 (142 g. 40%) after flash chromatography (5% EtOAc/Hexanes). $^1$H NMR (300 MHz, CDCl$_3$) δ 0.83 (t, J=7.3 Hz, 3H), 1.24 (t, J=7.1 Hz, 3H), 1.72 (s, 3H), 2.03-2.17 (m, 2H), 2.25 (s, 3H), 4.17 (q, J=7.1 Hz, 2H), 5.72-5.81 (m, 2H), 5.95-6.04 (dd, J=10, 15 Hz, 1H), 6.18-6.27 (dd, J=10, 15 Hz, 1H); $^{13}$C NMR (75 MHz, CDCl$_3$) δ 13.2, 13.9, 22.8, 25.6, 30.2, 56.1, 61.9, 128.2, 128.4, 132.1, 138.5, 171.6, 194.8. IR (NaCl) 2929, 1736, 1693 cm$^{-1}$; HRMS (ES) m/z calculated for C$_{13}$H$_{20}$O$_3$SNa$^+$ (M+Na$^+$) 279.1025 obsd 279.1032.

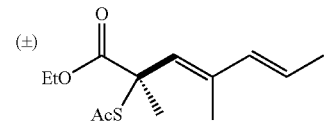

15

(±)-2-Thioalkynyl-2,4-dimethyl-hepta-3,5-dienoic acid ethyl ester (15). From 10 (369 mg, 1.46 mmol) and alkynyl chloride (103 μL, 1.46 mmol) following general procedure C gave 15 (271 mg, 77%) after flash chromatography (5% EtOAc/Hexanes). $^1$H NMR (300 MHz, CDCl$_3$) δ 1.26 (t, J=7.1 Hz, 3H), 1.74 (d, J=6.6 Hz, 3H), 1.81 (s, 3H), 1.85 (s, 3H), 2.25 (s, 3H), 4.17 (q, J=7.1 Hz, 2H), 5.56 (s, 1H), 5.65-5.73 (dq, J=6.6, 16 Hz, 1H), 5.99 (d, J=16 Hz, 1H); $^{13}$C NMR (75 MHz, CDCl$_3$) δ 13.8, 14.1, 18.2, 26.2, 30.5, 55.6, 62.0, 125.2, 128.3, 135.7, 138.5, 172.2, 194.8. IR (NaCl) 2926, 1737, 1694 cm$^{-1}$; HRMS (EI) m/z calculated for C$_{13}$H$_{20}$O$_3$S (M$^+$) 256.1133 obsd 256.1118.

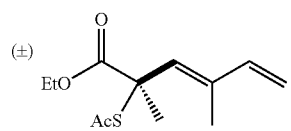

16

(±)-2-Thioalkynyl-2,4-dimethyl-hexa-3,5-dienoic acid ethyl ester (16). From (±) 7 (380 mg, 1.56 mmol) and alkynyl chloride (110 μL, 1.56 mmol) following general procedure C gave 16 (230 mg, 61%) after flash chromatography (5% EtOAc/Hexanes). $^1$H NMR (300 MHz, CDCl$_3$) δ 1.25 (t, J=7.1 Hz, 3H), 1.84 (s, 3H), 1.87 (s, 3H), 2.24 (s, 3H), 4.21 (q, J=7.1 Hz, 2H), 5.03 (d, J=10.6 Hz, 1H), 5.21 (d, J=17.3 Hz, 1H), 5.74 (s, 1H), 6.26-6.35 (dd, J=10.6, 17.3 Hz, 1H); $^{13}$C NMR (75 MHz, CDCl$_3$) δ 12.9, 13.9, 25.9, 30.1, 55.8, 62.0, 113.3, 131.3, 138.3, 141.3, 182.3, 194.6. IR (NaCl) 2982, 1735, 1692 cm$^{-1}$.

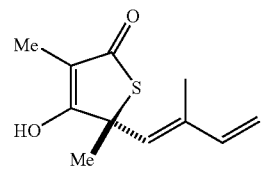

17

General Procedure D. 5-(R)-4-Hydroxy-3,5-dimethyl-5-(2-methyl-buta-1,3-dienyl)-5-H-thiophen-2-one (17) Thiolactamycin). To 12 (315 mg, 1.23 mmol) in THF (18.5 mL) at −78° C. was added LiHMDS (3.1 mL, 3.1 mmol, 1.0 M in THF) and the solution was allowed to slowly warm to −5° C. The solution was then poured into 1 N HCl (25 mL) and extracted with EtOAc (3×15 mL). The combined organics were dried MgSO$_4$), filtered and evaporated. This crude mixture was taken up in NaHCO$_3$ (sat, 15 mL) and extracted with Et$_2$O (3×10 mL). The aqueous layer was then acidified to pH 3 (pH paper) with 1 N HCl and extracted with Et$_2$O (3×10 mL) and EtOAc (2×10 mL). The combined organics were dried (MgSO₄), filtered and evaporated to provide pure 17. (182 mg, 70%, 96% ee). Recrystallization from Hexanes/Acetone (3:1) gave optically enriched 17. $[\alpha]_D^{24}$=+174 (c 0.6, MeOH), mp 119.5-121° C. (lit $[\alpha]_D^{20}$+176 (c 1.0, MeOH), mp 120° C.)[2]. ¹H NMR (300 MHz, CDCl₃) δ 1.72 (s, 3H), 1.76 (s, 3H), 1.91 (s, 3H), 5.05 (d, J=10.7 Hz, 1H), 5.23 (d, J=17.3 Hz, 1H), 5.58 (s, 1H), 6.23-6.33 (dd, J=10.7, 17.3 Hz, 1H); ¹³C NMR (300 MHz, CDCl₃) δ 7.60, 12.0, 29.8, 55.3, 110.6, 113.9, 129.1, 140.3, 140.7, 179.2, 196.7. IR (NaCl) 3422, 1607 cm⁻¹. Analysis Calculated for C₁₁H₁₄O₂S: C, 62.8; H, 6.71; Found: C, 62.1, 6.71.

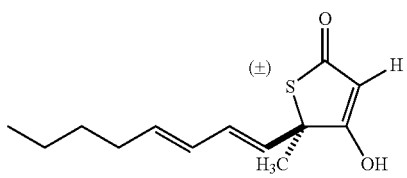

18

(±)-4-Hydroxy-5-methyl-5-octa-1,3-dienyl-5-H-thiophen-2-one (18). From 13 (62 mg, 0.22 mmol following general procedure D was obtained 18 (21 mg, 41%). ¹H NMR (300 MHz, CDCl₃) keto tautomer) δ 0.88 (t, J=6.9 Hz, 3H), 1.19-1.41 (m, 4H), 1.75 (s, 3H), 2.03-2.19 (m, 2H), 3.22 (d, J=21 Hz, 1H), 3.51 (d, J=21 Hz, 1H), 5.67 (d, J=15 Hz, 1H), 5.80 (dt, J=7, 17 Hz, 1H), 6.02 (dd, J=10, 15 Hz, 1H), 6.37 (dd, J=10, 15 Hz, 1H). ¹H NMR (300 MHz, MeOD) enol tautomer δ 0.97-1.03 (m, 3H), 1.36-1.53 (m, 4H), 1.87 (s, 3H), 2.15-2.22 (m, 2H), 5.78 (d, J=15 Hz, 1H), 5.82-5.90 (m, 1H), 6.10-6.19 (m, 1H), 6.38 (dd, J=10.3, 15.4 Hz, 1H); ¹³C (75 MHz, MeOD) enol tautomer δ 14.4, 23.3, 25.2, 32.6, 33.4, 60.9, 102.1 (m), 130.7, 131.7, 132.7, 137.5, 188.9, 196.9. IR (NaCl) 2927, 1588 cm⁻¹; HRMS (ES) calculated for C₁₃H₁₈O₂SNa⁺ (M+Na⁺) 261.0911; obsd 261.0912.

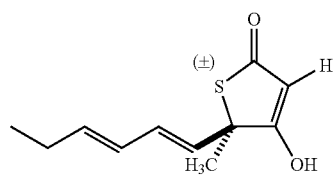

19

(±)-4-Hydroxy-5-methyl-5-hexa-1,3-dienyl-5-H-thiophen-2-one (19). From 14 (364 mg, 0.46 mmol) following general procedure D was obtained 19 (180 mg, 60%). ¹H (300 MHz, CDCl₃, exists as a mixture 2.3:1 of the keto:enol tautomer) keto tautomer: δ 1.00 (t, J=7.4 Hz, 3H); 1.76 (s, 3H); 2.09-2.16 (m, 2H); 3.21 (d, J=21 Hz, 1H); 3.52 (d, J=21 Hz, 1H); 5.70 (d, J=15 Hz, 1H); 5.86 (dt, J=15 Hz, 6 Hz, 1H); 6.02 (dd, J=10, 15 Hz, 1H), 6.38 (dd, J=15, 10 Hz, 1H); ¹H NMR (300 MHz, MeOD) enol tautomer δ 1.09 (t, J=7.4 Hz, 3H), 1.87 (s, 3H), 2.14-2.29 (m, 2H), 5.78 (d, J=15 Hz, 1H), 5.87 (dt, J=15, 6.57 Hz, 1H), 6.09-6.18 (m, 1H), 6.38 (dd, J=10.2, 15 Hz, 1H); ¹³C NMR (75 MHz, MeOD) enol tautomer δ 14.1, 25.2, 26.9, 61.0, 101 (m), 129.7, 131.7, 132.7, 138.9, 188.9, 197.1. IR (NaCl) 2965, 1592 cm⁻¹; HRMS (ES) m/z calculated for C₁₁H₁₄O₂SNa⁺ (M+Na⁺) 233.0607, obsd 233.0626.

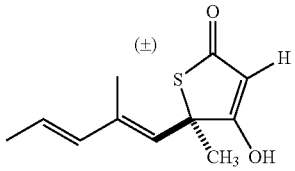

20

(±)-4-Hydroxy-5-methyl-5 (2-methyl-penta-1,3-dienyl)-5-H-thiophen-2-one (20). From 15 (226 mg, 0.9 mmol) following general procedure D was obtained 20 (95 mg, 49%). ¹H NMR (300 MHz, CDCl₃) keto-tautomer) δ 1.75 (s, 3H), 1.77 (d, J=3.2 Hz, 3H), 1.84 (s, 3H), 3.42 (d, J=1.5 Hz, 2), 5.43 (d, J=21 Hz, 1), 5.66 (bs, 1H), 5.78 (dd, J=6, 22 Hz, 1H), 6.04 (d, J=15 Hz, 1H); ¹H NMR (300 MHz, MeOD) (enol tautomer) δ 1.80-1.85 (m, 6H), 1.90 (s, 3H), 5.59 (s, 1H), 5.80-5.95 (m, 1H), 6.17 (d, J=15 Hz, 1H); ¹³C NMR (75 MD, MeOD) (enol tautomer) δ 13.4, 18.4, 30.7, 59.2, 101.2 (m) 126.2, 128.4, 136.9, 140.6, 190.2, 197.6. IR (NaCl) 2929, 1593 cm⁻¹; HRMS (ES) m/z calculated for C₁₁H₁₄O₂SNa⁺ (M+Na⁺) 233.0607 obsd. 233.0597.

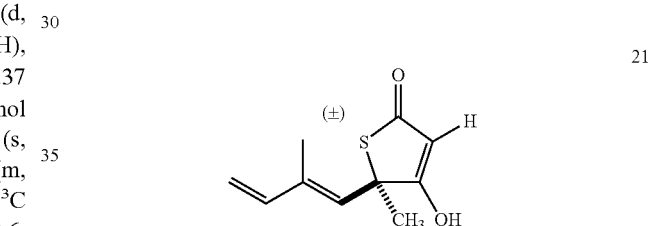

21

(±)-4-Hydroxy-5-methyl-5 (2-methyl-buta-1,3-dienyl)-5-H-thiophen-2-one (21). From 16 (181 mg, 0.75 mmol) following general procedure D was obtained 21 (66 mg, 45%). ¹H NMR (300 MHz, CDCl₃) keto tautomer) δ 1.78 (s, 3H), 1.86 (s, 3H), 3.43 (d, J=5.6 Hz, 2H), 5.12 (d, J=10.6 Hz, 1H), 5.27 (d, J=17.3 Hz, 1H), 5.83 (s, 1H), 6.27-6.37 (dd, J=10.6, 17.3 Hz, 1H). ¹H NMR (300 MHz, MeOD) (enol tautomer) δ 1.79 (s, 3H), 1.84 (s, 3H), 5.04 (d, J=10.7 Hz, 1H), 5.25 (d, J=17.3 Hz, 1H), 5.66 (s, 1H), 6.36 (dd, J=10.7, 17.3 Hz, 1H); ¹³C NMR (75 MHz, MeOD) δ 12.6, 30.4, 59.0, 102 (m), 116.9, 131.4, 140.6, 142.3, 189.9, 197.3. HRMS (EI) m/z calculated for C₁₀H₁₂O₂S⁺ (M⁺) 196.0552 obsd. 196.0552.

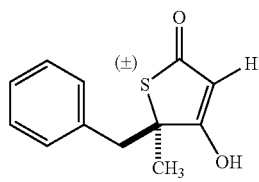

22

(±t)-5-Benzyl-4-hydroxy-5-methyl-5-H-thiophen-2-one (22). From 31 (1.4 mg, 5.0 mmol) following general procedure D was obtained 22 (500 mg, 45%). ¹H NMR (300 MHz, CDCl₃) δ 1.71 (s, 3H), 2.89 (ab q, J=22 Hz, 2H), 3.17 (ab q, J=14 Hz, 2H), 7.26 (m, 5H); $^{13}$C NMR (75 MHz, CDCl$_3$) d 26.2, 46.6, 48.5, 67.9, 127.7, 128.6, 130.6, 134.9, 195.3, 207.3.

23

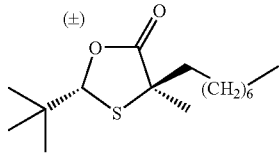

General Procedure E. (±)-2-tert-butyl-5-methyl-5-octyl-[1,3]-oxathiolan-4-one (23). To a mixture of LiHMDS (6.2 mL, 6.20 mmol, 1 M in THF) in THF (9.7 mL) at −78° C. was added (±)-1 (1.00 g, 5.75 mmol) in THF (9.60 mL) by cannula dropwise, and the resulting solution stirred for 30 minutes. at −78° C. Then, octyl triflate (1.63 g, 6.20 mmol) in TH (4 mL) at −78° C. was added via cannula. After stirring at −78° C. for 2 hours, 1 N HCl (10 mL) was added and the solution was extracted with Et$_2$O (3×15 mL). The combined organics were dried (MgSO$_4$), filtered and evaporated. Flash chromatography (2% EtOAc/Hexanes) gave pure 23 as a 2:1-6:1 mixture of separable diastereomers (1.33 g, 81%). $^1$H NMR (300 MHz, CDCl$_3$) δ 0.86 (t, J=6.5 Hz, 3H), 0.99 (s, 9H), 1.24-1.26 (m, 12H), 1.54 (s, 3H), 1.72-1.84 (m, 2H), 5.13 (s, 1H); $^{13}$C NMR (75 MHz, CDCl$_3$) δ 13.9, 22.6, 24.9, 25.1, 25.9, 29.2, 29.3, 29.5, 31.8, 35.2, 41.2, 55.3, 86.5, 177.7. IR (NaCl) 3443, 2929, 1829, 1769 cm$^{-1}$; Analysis Calculated. for C$_{16}$H$_{30}$O$_2$S: C, 67.0; H, 10.6; Found: C, 66.3; H, 10.5. HRMS (ED m/z calculated for C$_{16}$H$_{30}$O$_2$S$^+$ (M$^+$) 286.1967 obsd. 286.1969.

24

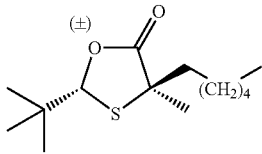

(±)-2-tert-butyl-5-methyl-5-hexyl-[1,3]-oxathiolan-4-one (24). From (±)-1 (500 mg, 2.87 mL) and hexyl triflate (738 mg, 2.87 mmol) following general procedure E was obtained 24 (557 mg, 75%) as a 2:1-6:1 mixture of separable diastereomers. $^1$H NMR (300 MHz, CDCl$_3$) δ 0.87 (t, J=6.5 Hz, 3H), 0.99 (s, 9H), 1.24-1.29 (m, 8H), 1.54 (s, 3H), 1.72-1.80 (m, 2H), 5.13 (s, 1H); $^{13}$C NMR (75 MHz, CDCl$_3$) δ 13.9, 22.5, 24.9, 24.9, 25.1, 25.9, 29.1, 31.6, 41.2, 55.3, 86.7, 177.8. IR (NaCl) Analysis Calculated. for C$_{14}$H$_{26}$O$_2$S: C, 65.1; H, 10.1; Found: C, 64.5; H, 10.1. HRMS (EI) m/z calculated for C$_{14}$H$_{26}$O$_2$S$^+$ (M$^+$) 258.1654 obsd. 286.1653.

25

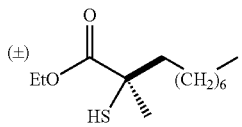

26

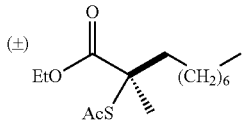

General Procedure F. (±)-2-Alkylsulfanyl-2-methyl-decanoic acid ethyl ester (26). To 23 (650 mg, 2.27 mmol) in EtOH (14.1 mL) was added NaOEt (2.1 M) (2.16 mL, 4.54 mmol) (freshly prepared from Na metal (200 mg, 8.3 mmol) in EtOH (4.0 mL)) and the solution was allowed to stir at room temperature. After 2 hours, the solution was poured into NH$_4$Cl$_{(sat)}$/1 N HCl (25 mL, 3:1) and this mixture was extracted with Et$_2$O (3×20 mL). The combined organics were then washed with H$_2$O (3×25 mL), dried (MgSO$_4$), filtered and evaporated to give crude 25. To 25 dissolved in CH$_2$Cl$_2$ (26 mL) at 0° C. was added NEt$_3$ (0.5 mL, 3.49 mmol) and alkynyl chloride (0.3 mL, 3.49 mmol). After 40 minutes at 0° C., NH$_4$Cl$_{(sat)}$ (30 mL) was added and the solution was extracted with CH$_2$Cl$_2$. The combined organics were dried (MgSO$_4$), filtered and evaporated. Flash chromatography (5% EtOAc/Hexanes) gave pure 26 (542 mg, 79%). $^1$H NMR (300 MHz, CDCl$_3$) δ 0.87 (t, J=6.9 Hz, 3H); 1.22-1.27 (m, 15H), 1.61 (s, 3H), 1.75-1.84 (m, 2H), 2.26 (s, 3H), 4.18 (q, J=7.1 Hz, 2H); $^{13}$C NMR (75 MHz, CDCl$_3$) δ 13.9, 14.1, 22.6, 23.4, 24.4, 29.1, 29.2, 29.6, 30.3, 31.8, 38.3, 55.8, 61.5, 173.1, 195.8. IR (NaCl) 3430, 1868, 1693, 1644 cm$^{-1}$; Analysis Calculated. for C$_{15}$H$_{28}$O$_3$S: C, 62.5; H, 9.78; Found: C, 62.6; H, 9.83.

27

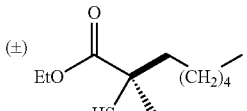

28

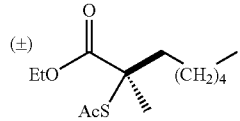

(±)-2-Alkynylsufanyl-2-methyl-octanoic acid ethyl ester (28) From 24 (940 mg, 3.63 mmol) and alkynyl chloride (0.3 mL, 3.63 mmol) following general procedure F was obtained 28 (727 mg, 77%) after flash chromatography (5% EtOAc/Hexanes). $^1$H NMR (300 MHz, CDCl$_3$) d 0.86 (t, J=6.9 Hz, 3H), 1.22-1.27 (m, 11H), 1.61 (s, 3H), 1.75-1.79 (m, 2H), 2.25 (s, 3H), 4.17 (q, J=7 Hz, 2H); $^{13}$C NMR (75 MHz, CDCl$_3$) δ 13.9, 14.1, 22.4, 23.4, 24.4, 29.3, 30.3, 31.5, 38.4, 55.7, 61.5 173.0, 194.7. IR (NaCl) 3449, 1736, 1694 cm$^{-1}$; Analysis Calculated. for C$_{13}$H$_{24}$O$_3$S: C, 59.9; H, 9.29; Found: C, 60.6; H, 9.44.

29

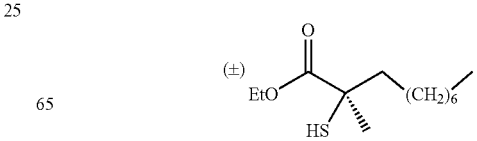

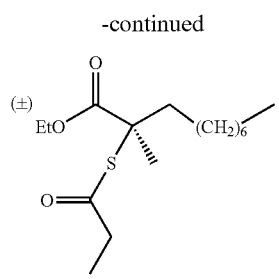

30

(±)-2-Methyl 2-propionylsulfanyl-decanoic acid ethyl ester (30). From 23 (613 mg, 2.14 mmol) and propionyl chloride (0.19 mL, 2.14 mmol) following general procedure F was obtained 30 (484 mg, 75%) after flash chromatography (5% EtOAc/Hexanes). $^1$H NMR (300 MHz, CDCl$_3$) δ 0.84 (t, J=6.9 Hz, 3H), 1.10 (t, J=7.5 Hz, 3H), 1.19-1.24 (m, 15H), 1.58 (s, 3H), 1.72-1.77 (m, 2H), 2.48 (q, J=7.5 Hz, 2H), 4.17 (q, J=7 Hz, 2H); $^{13}$C NMR (75 MHz, CDCl$_3$) δ 9.45, 14.1, 14.1, 22.6, 23.5, 24.5, 29.1, 29.3, 29.7, 31.8, 36.9, 38.5, 55.5, 61.4, 173.2, 199.2. Analysis Calculated for C$_{16}$H$_{30}$O$_3$S: C, 63.5; H, 10.0; Found: C, 63.7; H, 10.0.

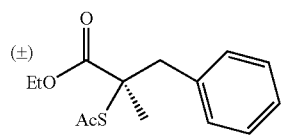

31

(±)-2-Alkynylsulfanyl-2-methyl-3-phenyl-decanoic acid ethyl ester (31). From 5-Benzyl-2-tert-butyl-5-methyl-[1,3] oxathiolan-4-one$^1$. (1.2 g, 4.7 mmol) following general procedure F was obtained 31 (954 mg, 76%) after flash chromatography (5% EtOAc/Hexanes). $^1$H NMR (300 MHz, CDCl$_3$) δ 1.19 (t, J=7 Hz, 3H), 1.55 (s, 3H), 2.26 (s, 3H), 3.13 (q, J=13 Hz, 2H), 4.13 (q, J=7 Hz, 2H), 7.1 (m, 2H), 7.2 (m, 3H); $^{13}$C NMR (75 MHz, CDCl$_3$) δ 14.0, 23.1, 30.3, 43.6, 56.3, 61.7, 127.2, 128.1, 130.7, 135.4, 172.8, 194.8.

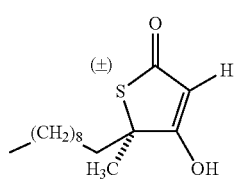

32

General Procedure G. (±)-4-Hydroxy-5-methyl-5-octyl-5-H-thiophen-2-one (32). To 26 (500 mg, 1.7 mmol) in toluene (27 mL) at −78° C. was added LiHMDS (4.3 mL, 4.3 mmol, 1.0 M in THF) and the solution was allowed to slowly warm to −5° C. The solution was then poured into 1 N HCl (40 mL) and extracted with EtOAc (3×25 mL). The combined organics were dried (MgSO$_4$), filtered and evaporated. Flash chromatography (20% EtOAc/2% CH$_3$CO$_2$H/Hexanes) gave 32 (308 mg, 73%). $^1$H NMR (300 MHz, CDCl$_3$) (keto-tautomer) δ 0.86 (t, J=6 Hz, 3H), 1.19-1.24 (m, 10H), 1.48-1.53 (m, 2H), 1.65 (s, 3H), 1.77-1.85 (m, 1H), 1.94-2.01 (m, 1H), 3.36 (s, 2H); $^1$H NMR (300 MHz, MeOD) (enol tautomer) δ 0.87-0.89 (m, 3H), 1.29 (m, 10H), 3.29 (s, 3H), 1.81-1.87 (m, 2H); $^{13}$C NMR (75 MHz, MeOD) (enol tautomer) δ 14.7, 23.8, 26.4, 27.1, 30.5, 30.6, 30.8, 33.2, 39.8, 61.3, 103.1 (m), 189.8, 197.8. IR (NaCl) 3422, 1593 cm$^{-1}$; Analysis Calculated for C$_{13}$H$_{22}$O$_2$S: C, 64.4; H, 9.15; Found: C, 64.3; H, 9.10.

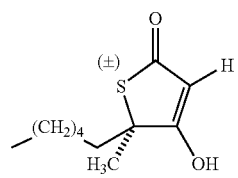

33

(±)-4-Hydroxy-5-methyl-5-hexyl-5-H-thiophen-2-one (33). From 28 (715 mg, 2.75 mmol) following general procedure G was obtained 33 (402 mg, 69%) after flash chromatography (20% EtOAc/2% CH$_3$CO$_2$H/Hexanes). $^1$H NMR (300 MHz, CDCl$_3$) 3 keto tautomer) 0.86 (t, J=7 Hz, 3H), 1.27 (bs, 8H), 1.68 (s, 3H), 1.94-2.26 (m, 2H), 3.35 (s, 2H). $^1$H NMR (300 MHz, MeOD) (enol tautomer) δ 0.89 (t, J=6.5 Hz, 3H), 1.21-1.36 (m, 7H), 1.46-1.54 (m, 1H), 1.64 (s, 3H), 1.80-1.90 (m, 2H); $^{13}$C NMR (75 MHz, MeOD) δ 14.6, 23.8, 26.3, 27.1, 30.5, 32.9, 39.8, 61.3, 103.5 (m), 189.8, 197.8. Analysis Calculated for C$_{11}$H$_{18}$O$_2$S: C, 61.6; H, 8.47; Found: C, 61.7; H, 8.67.

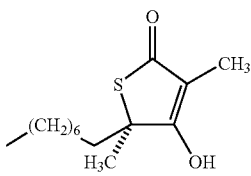

34

(±)-4-Hydroxy-3,5-dimethyl-5-octyl-5-H-thiophen-2-one (34). From 30 (469 mg, 1.55 mmol) and NaHMDS (3.87 mL, 3.87 mmol, 1.0 M in TH) following general procedure G was obtained 34 (397 mg, 70%). $^1$H NMR (300 MHz, CDCl$_3$) (enol tautomer) δ 0.86 (t, J=6.8 Hz, 3H), 1.23 (s, 11H), 1.30-1.45 (m, 1H), 1.59 (s, 3H), 1.74 (s, 3H), 1.84-1.88 (m, 2H); $^{13}$C NMR (75 MHz, CDCl$_3$) δ 7.48, 14.0, 22.6, 25.2, 25.9, 29.2, 29.4, 29.6, 31.8, 38.5, 58.2, 110.5, 180.9, 198.0. IR (NaCl) 2927, 1601 cm$^{-1}$

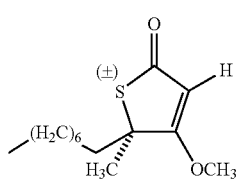

35

General Procedure H. (±)-4-Methoxy-5-methyl-5-octyl-5-H-thiophen-2-one (35). To 32 (70 mg, 0.27 mmol) in DMF (1.1 mL) cooled to −40° C. was added NaH (14 mg, 0.35 mmol, 60% in mineral oil) and the solution was allowed to warm and stir at 0° C. for 30 minutes. Dimethyl sulfate (50 µl, 0.55 mmol) was then added directly and the mixture was allowed to warm and stir for 2.5 hours at room temperature. NH$_4$Cl$_{(sat)}$/1 N HCl (3:1, 10 mL) was added and the solution was extracted with Et$_2$O (3×10 mL). The combined organics were washed with H$_2$O (3×15 mL), dried (MgSO$_4$), filtered and evaporated. Flash chromatography (15% EtOAc/Hexanes) gave pure 35 (59 mg, 80%). ¹H NMR (300 MHz, CDCl₃) δ 0.85 (t, J=7 Hz, 3H); 1.07-1.18 (m, 1H), 1.23 (s, 10H), 1.43-1.49 (m, 1H), 1.61 (s, 3H), 1.74-1.81 (m, 2H), 3.81 (s, 3H), 5.29 (s, 1H); ¹³C NMR (75 MHz, CDCl₃) δ 14.0, 22.6, 25.1, 26.4, 29.1, 29.3, 29.5, 31.8, 38.8, 59.3, 59.4, 101.3, 187.3, 193.8. Analysis. Calculated for C₁₄H₂₄O₂S: C, 65.6; H, 9.50; Found: C, 65.8; H, 9.50.

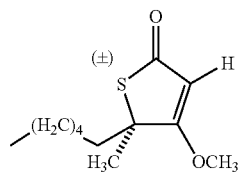

(±)-4-Methoxy-5-methyl-5-hexyl-5-H-thiophen-2-one (36). From 33 (40.3 mg, 0.19 mmol) and dimethyl sulfate (35 μL, 0.37 mmol) following general procedure H was obtained 36 (25 mg, 58%) after flash chromatography (15% EtOAc/Hexanes). ¹H NMR (300 MHz, CDCl₃) δ 0.86 (t, J=6.7 Hz, 3H), 1.08-1.13 (m, 1H), 1.24 (s, 6H), 1.35-1.39 (m, 1H), 1.61 (s, 3H), 1.75-1.82 (m, 2H), 3.81 (s, 3H), 5.30 (s, 1H); ¹³C NMR (75 MHz, CDCl₃) δ 14.0, 22.5, 25.1, 26.4, 29.2, 31.5, 38.9, 59.4, 59.4, 101.3, 187.3, 193.8.

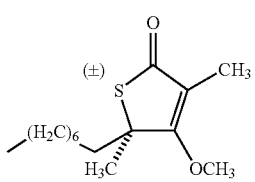

(±)-4-Methoxy-3,5-dimethyl-5-octyl-5-H-thiophen-2-one (37). From 34 (40 mg, 0.16 mmol), KH (27 mg, 0.20 mmol, 30% in mineral oil) and dimethyl sulfate (30 μL, 0.31 mmol) following general procedure H was obtained 37 (30 mg, 71%). ¹H NMR (300 MHz, CDCl₃) δ 0.86 (t, J=7 Hz, 3H), 1.06-1.09 (m, 1H), 1.24 (s, 10H), 1.41-1.48 (m, 1H), 1.55 (s, 3H), 1.71-1.79 (m, 2H), 1.98 (s, 3H), 4.09 (s, 3H); ¹³C NMR (75 MHz, CDCl₃) δ 9.59, 14.1, 22.6, 25.2, 26.5, 29.2, 29.4, 29.6, 31.8, 38.9, 58.7, 59.8, 111.3, 180.2, 195.7. IR (NaCl) 2927, 1676, 1631, 1582 cm⁻¹. Analysis Calculated for C₁₅H₂₆O₂S: C, 66.6; H, 9.69; Found: C, 66.5; H, 9.67.

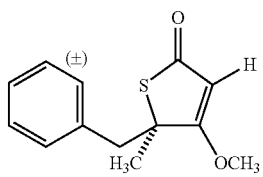

(±)-5-Benzyl-4-methoxy-5-methyl-5-H-thiophen-2-one (38). From 22 (50 mg, 0.23 mmol), and dimethyl sulfate (44 μL, 0.45 mmol) following general procedure H was obtained 38 (38 mg, 74%). ¹H NMR (300 MHz, CDCl₃) δ 1.65 (s, 3H), 3.1 (q, J=7 Hz, 2H), 3.84 (s, 3H), 5.19 (s, 1H), 7.21 (m, 5H); ¹³C NMR (75 MHz, CDCl₃) δ 26.0, 45.0, 59.3, 59.9, 101.9, 127.2, 128.0, 130.4, 135.9, 186.5, 192.9.

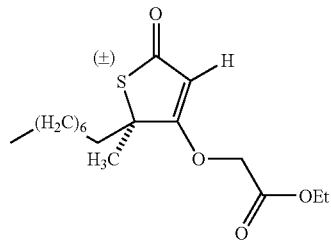

(±)-5-Methyl-5-octyl-2-oxo-thiophen-4-yloxy)-acetic acid ethyl ester (39). From 32 (39 mg, 0.16 mmol) and ethyl bromoacetate (36 μL, 0.32 mmol) following general procedure H was obtained 39 (39 mg, 73%) after flash chromatography (15% EtOAc/Hexanes). ¹H NMR (300 MHz, CDCl₃) δ 0.86 (t, J=6 Hz, 3H), 1.24 (s, 11H), 1.29 (t, J=7 Hz, 3H), 1.47-1.48 (m, 1H), 1.68 (s, 3H), 1.85-1.88 (m, 2H), 4.25 (q, J=7 Hz, 2H), 4.54 (s, 2H), 5.20 (s, 1H); ¹³C NMR (75 MHz, CDCl₃) δ 14.1, 14.1, 22.6, 25.1, 26.4, 29.2, 29.3, 29.5, 31.8, 38.8, 59.7, 61.9, 67.9, 102.3 166.2, 185.3, 193.4. IR (NaCl) 2928, 1762, 1682, 1612 cm⁻¹. Analysis Calculated for C₁₇H₂₈O₄S: C, 62.2; H, 8.59: Found: C, 62.2; H, 8.67.

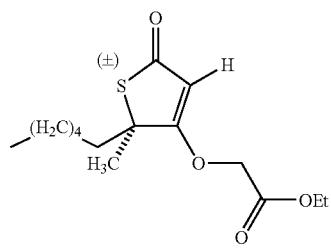

(±)-5-Methyl-5-hexyl-2-oxo-thiophen-4-yloxy)-acetic acid ethyl ester (40). From 33 (20 mg, 0.09 mmol) and ethyl bromoacetate (20 μL, 0.2 mmol) following general procedure H was obtained 40 (18 mg, 67%) after flash chromatography (15% EtOAc/Hexanes). ¹H NMR (300 MHz, CDCl₃) d 0.86 (t, J=6.8 Hz, 3H), 1.24-1.27 (m, 7H), 1.32 (t, J=7 Hz, 3H), 1.47-1.48 (m, 1H), 1.68 (s, 3H), 1.84-1.88 (m, 2H); 4.25 (q, J=7 Hz, 2H), 4.54 (s, 2H), 5.21 (s, 1H); ¹³C NMR (75 MHz, CDCl₃) δ 14.1, 14.1, 22.5, 25.1, 26.4, 29.2, 31.6, 38.9, 59.7, 61.9, 68.0, 102.3, 166.2, 185.3, 193.3. IR (NaCl) 2932, 1762, 1682, 1612 cm⁻¹. Analysis Calculated for C₁₅H₂₄O₄S: C, 59.9; H, 8.05: Found: C, 59.9; H, 8.08.

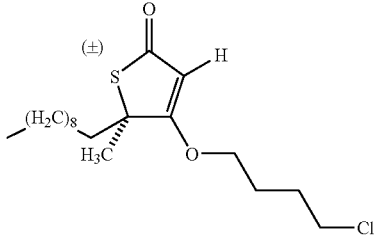

(±)-4-(4-Chloro-butoxy)-5-methyl-5-octyl-5H-thiophen-2-one (41). From 32 (47 mg, 0.18 mmol) and 3-iodo-1-chlorobutane (40 μL, 0.36 mmol) following general procedure H was obtained 41 (46 mg, 85%) after flash chromatography (20% EtOAc/Hexanes). ¹H NMR (300 MHz, CDCl₃) δ 0.86 (t, J=7 Hz, 3H), 1.07-1.27 (m, 1H), 1.24 (s, 10H) 1.48-1.51 (m, 1H), 1.62 (s, 3H), 1.75-1.82 (m, 2H), 1.89-1.98 (m, 4H), 3.59 (t, J=5.9 Hz, 2H), 3.95-3.98 (m, 2H), 5.28 (s, 1H); ¹³C NMR (75 MHz, CDCl₃) δ 14.1, 22.6, 25.1, 26.0, 26.5, 29.0, 29.2, 29.3, 29.5, 29.7, 31.8, 44.1, 59.6, 71.7, 101.6, 186.1, 193.8. Analysis Calculated for C₁₇H₂₉C₂S: C, 61.3; H, 8.78, Found: C, 61.9; H, 9.01.

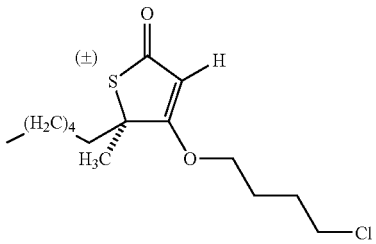

42

(±)-4-(4-Chloro-butoxy)-5-methyl-5-hexyl-5H-thiophen-2-one (42). From 33 (36 mg, 0.17 mmol) and 3-iodo-1-chlorobutane (40 μL, 0.34 mmol) following general procedure H was obtained 42 (32 mg, 75%) after flash chromatography (20% EtOAc/Hexanes). ¹H NMR (400 MHz, CDCl₃) δ 0.86 (t, J=5.1 Hz, 3H), 1.09-1.14 (m, 1H), 1.25 (s, 6H), 1.44-1.53 (m, 1H), 1.63 (s, 3H), 1.77-1.85 (m, 2H), 1.90-2.00 (m, 4H), 3.59 (t, J=4.5 Hz, 2H), 3.95-3.99 (m, 2H), 5.28 (s, 1H). ¹³C NMR (75 MHz, CDCl₃) δ 13.7, 22.3, 25.1, 26.1, 26.4, 29.1, 29.1, 31.5, 39.0, 43.9, 59.5, 71.6, 101.5, 185.9, 192.9. IR (NaCl) 2927, 1683, 1607 cm⁻¹. Analysis Calculated for C₁₅H₂₅C₂S: C, 59.1; H, 8.27; Found: C, 59.3; H, 8.39.

43

(±)-4-allyloxy-5-methyl-5-octyl-5H-thiophen-2-one (43). From 32 (31 mg, 0.12 mmol) and allyl bromide (21 μL, 0.25 mmol) following general procedure H was obtained a 3:1 mixture of 43 and 44 (26 mg, 74%) which could be separated and purified using flash chromatography (15% EtOAc/Hexanes). O-alkylated product 43. ¹H NMR (300 MHz, CDCl₃) δ 0.86 (t, J=6.3 Hz, 3H), 1.12-1.17 (m, 1H), 1.24 (s, 10H), 1.45-1.49 (m, 1H), 1.64 (s, 3H), 1.77-1.84 (m, 2H), 4.47 (d, J=5.6 Hz, 2H), 5.29 (s, 1H), 5.31 (d, J=11 Hz, 1H), 5.39 (d, J=17 Hz, 1H), 5.90-5.99 (ddd, J=5.6, 11, 17 Hz, 1H); ¹³C NMR (75 MHz, CDCl₃) δ 14.1, 22.6, 25.1, 26.5, 29.2, 29.3, 29.5, 31.8, 38.9, 59.7, 72.8, 102.0, 119.5, 130.8, 185.8, 193.8. IR (NaCl) 3441, 1681, 1609 cm⁻¹. Analysis Calculated for C₁₆H₂₆O₂S: C, 68.0; H, 9.20; Found: C, 68.1; H, 9.34.

(44) C-alkylated product ¹H NMR (300 MHz, CDCl₃) δ 0.86 (t, J=6.5 Hz, 3H), 1.25 (m, 12H), 1.54 (s, 3H), 1.79-1.84 (m, 2H), 2.43-2.47 (m, 2H), 5.05-5.11 (m, 2H), 5.57-5.69 (1H).

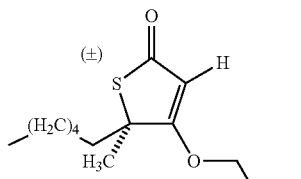

45

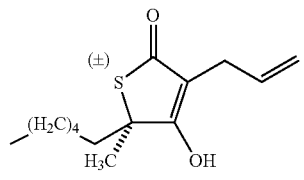

46

(±)-4-allyloxy-5-methyl-5-hexyl-5H-thiophen-2-one (45). From 33 (270 mg, 1.3 mmol) and allyl bromide (0.2 mL, 2.52 mmol) following general procedure H, was obtained a 2.3:1 mixture of 45 and 46 (205 mg, 58%) which could be separated and purified using flash chromatography (15% EtOAc/Hexanes). ¹H NMR (300 MHz, CDCl₃) (45) (O-alkylation) δ 0.84 (t, J=7 Hz, 3H), 1.09-1.17 (m, 1H), 1.23 (s, 6H), 1.40-1.51 (m, 1H), 1.62 (s, 3H), 1.73-1.83 (m, 2H), 4.46 (d, J=5.6 Hz, 2H), 5.33 (d, J=10 Hz, 1H), 5.38 (d, J=17 Hz, 1H), 5.28 (s, 1H), 5.87-5.98 (ddd, J=5.6, 10, 17 Hz, 1H); ¹³C NMR (75 MHz, CDCl₃) δ 14.0, 22.5, 25.1, 26.5, 29.2, 31.6, 38.9, 59.7, 72.8, 101.9, 119.6, 130.7, 185.8, 193.9. Analysis Calculated for C₁₄H₂₂O₂S: C, 66.10; H, 8.72; Found: C, 66.04; H, 8.72.

(46) (C-alkylation) ¹H NMR (300 MHz, CDCl₃) δ 0.86 (t, J=7 Hz, 3H), 1.24 (bs, 8H), 1.54 (s, 3H), 1.81-1.84 (m, 2H), 2.42-2.48 (m, 2H), 5.05-5.10 (m, 2H), 5.56-5.67 (m, 1H).

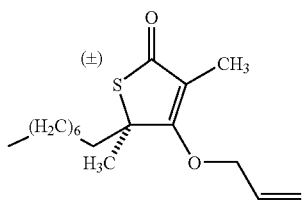

47

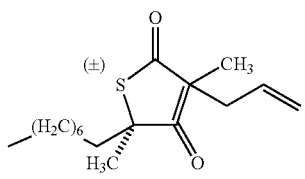

48

(±)-4-alkyloxy-3,5-dimethyl-5-octyl-5H-thiophen-2-one (47). (±)-Allyl-3,5-Dimethyl-5-octyl-thiophene-2,4-dione (48). From 34 (70 mg, 0.27 mmol) and allyl bromide (47 μL, 0.55 mmol) following general procedure H, was obtained a 2.3:1 mixture of 47 and 48 (C-alkylation data not shown) (67 mg, 82%) which could be separated and purified using flash chromatography (20% EtOAc/Hexanes).

(47). ¹H NMR (300 MHz, CDCl₃) δ 0.86 (t, J=7 Hz, 3H), 1.06-1.48 (m, 12H), 1.58 (s, 3H), 1.71-1.82 (, 2H), 1.94 (s, 3H), 4.80-4.82 (m, 2H), 5.28-5.46 (m, 2H), 5.89-5.03 (m, 1H); ¹³C NMR (75 MHz, CDCl₃) δ 9.65, 14.0, 22.6, 25.2, 26.6, 29.2, 29.3, 29.6, 31.8, 39.2, 57.5, 72.5, 118.2, 119.5, 132.6, 179.4, 193.8. IR (NaCl) 2855, 1676, 1628, 1580 cm⁻¹.

(48). ¹H NMR (300 MHz, CDCl₃) δ 0.86 (t, J=7 Hz, 3H), 1.16-1.47 (m, 15H), 1.57 (s, 3H), 1.74-1.96 (m, 2H), 2.42-2.46 (m, 2H), 5.04-5.10 (m, 2H), 5.53-5.67 (m, 1H).

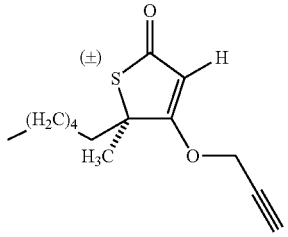

49

(±)-5-methyl-5-4-prop-2-ynyloxy-5H-thiophen-2-one (49). From 33 (45 mg, 0.21 mmol) and propargyl bromide (37 μL, 0.21 mmol) following general procedure H was obtained 49 (21 mg, 40%). ¹H NMR (300 MHz, CDCl₃) d 0.86 (t, J=7 Hz, 3H), 1.11-1.20 (m, 1H), 1.24 (s, 6H), 1.41-1.49 (m, 1H), 1.63 (s, 3H), 1.76-1.86 (m, 2H), 2.59 (t, J=2.5 Hz, 1H), 4.62 (d, J=3.7 Hz, 1H), 4.63 (d, J=3.7 Hz, 1H), 5.43 (s, 1H).

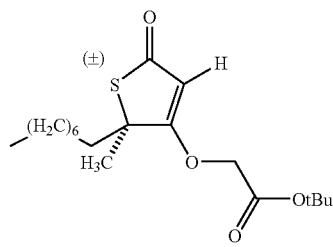

50

(±)-5-Methyl-5-octyl-2-oxo-thiophen-4-yloxy)-acetic acid tert-butyl ester (50). From 32 (60 mg, 0.25 mmol) and tert-butyl bromoacetate (73 μL, 0.49 mmol) following general procedure H, was obtained 50 (62 mg, 70%) after flash chromatography (15% EtOAc/Hexanes). ¹H NMR (300 MHz, CDCl₃) δ 0.86 (t, J=7 Hz, 3H), 1.24 (s, 12H), 1.49 (s, 9H), 1.68 (s, 3H), 1.83-1.86 (m, 2H), 4.43 (s, 2H), 5.19 (s, 1H); ¹³C NMR (75 MHz, CDCl₃) 8314.0, 22.6, 25.2, 26.3, 28.1, 29.2, 29.3, 29.5, 31.8, 38.9, 59.7, 68.5, 83.4, 102.1, 165.2, 185.5, 193.4. Analysis Calculated for C₁₉H₃₂O₄S: C, 64.0; H, 9.05; Found: C, 64.1; H, 9.08.

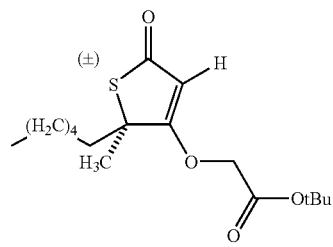

51

(±)-5-Methyl-5-hexyl-2-oxo-thiophen-4-yloxy)-acetic acid tert-butyl ester (51). From 33 (169 mg, 0.79 mmol) and tert-butyl bromoacetate (0.23 mL, 1.58 mmol) following general procedure H, was obtained 51 (206 mg, 80%) after flash chromatography (15% EtOAc/Hexanes). ¹H NMR (300 MHz, CDCl₃) δ 0.82 (t, J=6.8 Hz, 3H), 1.21 (s, 8H), 1.47 (s, 9H), 1.64 (s, 3H), 1.78-1.83 (m, 2H), 4.41 (s, 2H), 5.15 (s, 1H); ¹³C NMR (75 MHz, CDCl₃) δ 14.0, 22.5, 25.1, 26.3, 28.0, 29.1, 31.5, 38.9, 59.6, 68.4, 83.4, 102.1, 165.2, 185.5, 193.4.

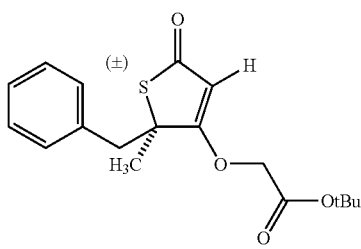

52

(±)-5-Phenyl-5-methyl-2-oxo-thiophen-4-yloxy)-acetic acid tert-butyl ester (52). From 22 (150 mg, 0.68 mmol) and tert-butyl bromoacetate (0.20 mL, 1.36 mmol) following general procedure H, was obtained 52 (159 mg, 74%) after flash chromatography (20% EtOAc/Hexanes). ¹H NMR (300 MHz, CDCl₃) δ 1.49 (s, 9H), 1.69 (s, 3H), 3.17 (s, 2H), 4.44 (q, J=8 Hz, 2H), 5.13 (s, 1H), 7.24 (m, 5H); ¹³C NMR (75 MHz, CDCl₃) δ 25.8, 28.1, 45.0, 60.1, 68.4, 83.6, 102.6, 127.2, 128.1, 130.5, 135.9, 165.3, 184.9, 192.8.

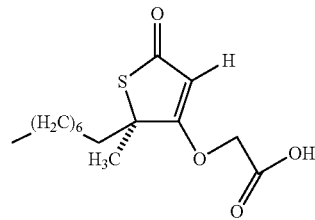

53

General Procedure I. (±)-5-Methyl-octyl-2-oxo-thiophen-4-yloxy)-acetic acid (53). To 50 (65 mg, 0.18 mmol) dissolved in CH₂Cl₂ (1.4 mL) was added trifluoroacetic acid (TFA) (0.7 mL) and the solution was stirred at room temperature for 4 hours. The solvents were evaporated and the crude material was chromatographed (20% EtOAc/2% CH₃CO₂H/Hexanes) to give pure 53 (48 mg, 89%). ¹H NMR (300 MHz, CDCl₃) δ 0.86 (t, J=6.9 Hz, 3H), 1.24 (s, 11H), 1.47-1.48 (m, 1H), 1.68 (s, 3H), 1.84-1.88 (m, 2H), 4.62 (s, 2H), 5.31 (s, 1H); ¹³C NMR (75 MHz, CDCl₃) δ 14.1, 22.6, 25.1, 26.1, 29.2, 29.3, 29.5, 31.8, 38.9, 60.1, 67.7, 102.4, 169.8, 185.8, 195.4. IR (NaCl) 3442, 1645 cm⁻¹; Analysis Calculated for C₁₅H₂₄O₄S: C, 59.9; H, 8.05; Found: C, 60.0; H, 8.09.

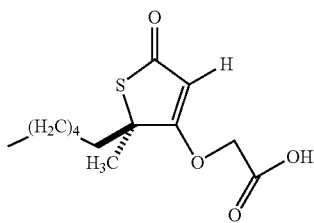

54

(±)-5-Methyl-5-hexyl-2-oxo-thiophen-4-yloxy)-acetic acid (54). To 51 (177 mg, 0.54 mmol) and trifluoroacetic acid (TFA) (2.61 mL) following general procedure I was obtained 54 (144 mg, 98%) after flash chromatography (20% EtOAc/2% $CH_3CO_2H$/Hexanes). $^1H$ NMR (300 MHz, $CDCl_3$) δ 0.85 (t, J=6.8 Hz, 3H), 1.24 (s, 7H), 1.44-1.47 (m, 1H), 1.68 (s, 3H), 1.84-1.91 (m, 2H), 4.62 (s, 2H), 5.33 (s, 1H); $^{13}C$ NMR (75 MHz, $CDCl_3$) δ 14.1, 22.6, 25.1, 26.1, 29.2, 31.6, 38.9, 60.3, 67.7, 102.4, 169.8, 185.9, 196.1.

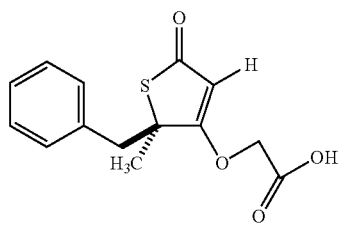

55

(±)-5-Phenyl-5-methyl-2-oxo-thiophen-4-yloxy)-acetic acid (55). To 52 (117 mg, 0.35 mmol) and trifluoroacetic acid (TFA) (1.4 mL) following general procedure I was obtained 55 (68 mg, 70%) after flash chromatography (30% EtOAc/2% $CH_3CO_2H$/(Hexanes). $^1H$ NMR (300 MHz, MeOD) δ 1.63 (s, 3H), 3.11 (dd, J=6.8 Hz, 13.6 Hz, 2H), 4.59 (s, 2H), 5.21 (s, 1H), 7.1 (m, 5H); $^{13}C$ NMR (75 MHz, MeOD) δ 26.7, 45.7, 61.9, 67.1, 103.9, 128.3, 129.1, 131.8, 137.5, 169.3, 187.3, 195.8.

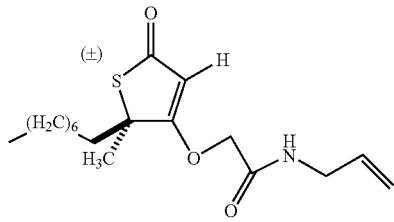

56

(±)—N-Allyl-(5-methyl-5-octyl-2-oxo-thiophen-4-yloxy)-acetamide (41). To a cooled solution (0° C.) of 53 (64 mg, 0.21 mmol) in $CH_2Cl_2$ (1.1 mL) was added 1-[3-(Dimethylamino)propyl]-3-ethylcarbodiimide hydrochloride (EDC) (49 mg, 0.25 mmol), DMAP (3 mg, 0.02 mmol), and allyl amine (18 μL, 0.25 mmol) and the mixture was allowed to warm to room temperature and stir for 12 hours. The solution was poured into a solution of 1 N $HCl/_{(sat)}$ (1:3) and extracted with $Et_2O$ (3×10 mL). The combined organics were dried ($MgSO_4$), filtered and evaporated to give crude 56.

Flash chromatography (50% EtOAc/Hexanes) gave pure 56 (50 mg, 66%). $^1H$ NMR (300 MHz, $CDCl_3$) δ 0.86 (t, J=7 Hz, 3H), 1.12-1.22 (m, 1H), 1.24 (s, 10H), 1.41-1.51 (m, 1H), 1.68 (s, 3H), 1.82-1.87 (m, 2H), 3.98 (app t, J=6 Hz, 2H), 4.50 (s, 2H), 5.20 (d, J=10 Hz, 1H), 5.22 (d, J=17.3 Hz, 1H), 5.35 (s, 1H), 5.80-5.90 (ddd, J=6, 10, 17 Hz, 1H), 6.19 (bs, 1H); $^{13}C$ NMR (75 MHz, $CDCl_3$) δ 14.0, 22.6, 25.3, 26.5, 29.2, 29.4, 29.5, 31.8, 39.1, 41.6, 59.3, 70.3, 103.4, 117.2, 133.2, 165.3, 183.9, 192.8. Analysis. Calculated. for $C_{18}H_{29}NO_3S$: C, 63.7; H, 8.61; Found: C, 63.4; H, 8.67.

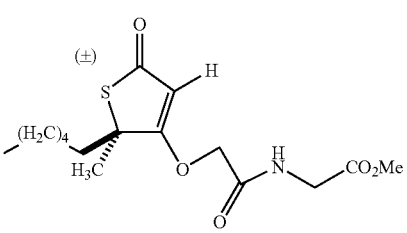

57

General Procedure J. (±)-(5-methyl-5-hexyl-2-oxo-thiophen-4-yloxy)-alkynyl-methyl glycinate (57). To a solution of 54 (42.4 mg, 0.15 mmol) in $CH_3CN$ (0.86 mL) was added tris(2-oxo-3-oxazolinyl)phosphine oxide[3] (91 mg, 0.20 mmol), methylglycinate hydrochloride (19.7 mg, 0.16 mmol) and $NEt_3$ (43 μL, 0.31 mmol) and the solution was allowed to stir at room temperature for 20 minutes. The mixture was poured into a solution of $NH_4Cl_{(sat)}$/1 N HCl (10 mL) and extracted with $Et_2O$ (3×10 mL). The combined organics were dried ($MgSO_4$), filtered, evaporated and chromatographed (40-50% EtOAc/Hexanes) to give pure 57 (43 mg, 80%). $^1H$ NMR (300 MHz, $CDCl_3$) δ 0.85 (t, J=6.8 Hz, 3H), 1.23-1.26 (m, 7H), 1.49-1.55 (m, 1H), 1.65 (s, 3H), 1.84-1.90 (m, 2H), 3.79 (s, 3H), 4.11 (d, J=5 Hz, 1H), 4.12 (d, J=5 Hz, 1H), 4.47 (s, 2H), 5.36 (s, 1H), 6.76 (bs, 1H).

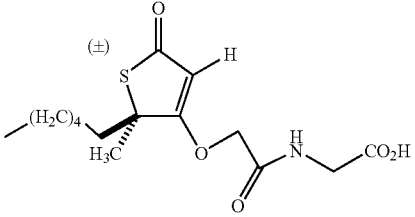

58

(±)-(5-methyl-5-hexyl-2-oxo-thiophen-4-yloxy)-alkynyl glycinate (58). To 57 (22 mg, 0.06 mmol) dissolved in THF/$H_2O$ (0.5 mL, 3:1), cooled to 0° C. was added LiOH (3 mg, 0.07 mmol) and this solution was allowed to stir for 45 minutes. Then the mixture was poured into a solution of HCl (10 mL, 1 N) and extracted with $Et_2O$ (3×10 mL). The combined organics were dried ($MgSO_4$), filtered and evaporated to give crude 58. Flash chromatography (50% EtOAc/2% $CH_3CO_2H$/Hexanes) gave pure 58 (19 mg, 86%). $^1H$ NMR (300 MHz, $CDCl_3$) δ 0.85 (t, J=6.7 Hz, 3H), 1.25 (s, 7H), 1.48-1.52 (m, 2H), 1.68 (s, 3H), 2.08-2.10 (m, 2H), 4.05 (s, 2H), 4.56 (s, 2H), 5.41 (s, 1H).

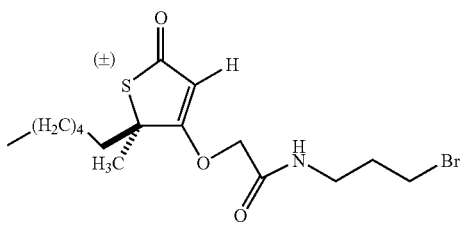

(±) N-(4-Bromobutyl)-(5methyl-5-hexyl-2-oxo-thiophen-4-yloxy)-acetamide (59). To 54 (61 mg, 0.22 mmol) and 1-aminopropanol hydrobromide (50 mg, 0.23 mmol) following general procedure J gave 59 (65 mg, 74%) after flash chromatography (50% EtOAc/Hexanes). $^1$H NMR (300 MHz, CDCl$_3$) δ 0.86 (t, J=6.9 Hz, 3H), 1.12-1.15 (m, 1H), 1.23-1.28 (s, 6H), 1.46-1.53 (m, 1H), 1.69 (s, 3H), 1.82-1.88 (m, 2H), 2.14 (quint. J=6 Hz, 2H), 3.42 (m, 2H), 3.54 (q, J=6.3 Hz, 2H), 4.43 (s, 2H), 5.35 (s, 1H) 6.45 (bs, 1H).

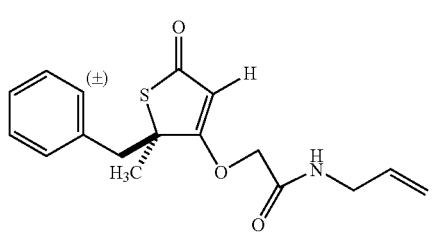

(±) N-allyl-(5-phenyl-5-methyl-2-oxo-thiophen-4-yloxy)-acetamide (60). To 55 (72 mg, 0.26 mmol) and allyl amine (21 µL, 0.28 mmol) following general procedure J gave 60 (39 mg, 47%) after flash chromatography (gradient 10-50% EtOAc/Hexanes). $^1$H NMR (300 MHz, CDCl$_3$) δ 1.73 (s, 3H), 3.17 (s, 2H), 3.93 (m, 2H), 4.41 (s, 2E), 5.22 (m, 2H), 5.24 (s, 1H), 5.80 (m, 1H), 5.83 (s, 1H), 7.24 (m, 5H) $^{13}$C NMR (75 MHz, CDCl$_3$) δ 26.0, 41.6, 45.4, 59.7, 70.3, 103.9, 117.1, 127.5, 128.3, 130.2, 133.3, 135.6, 165.3, 183.4, 192.0.

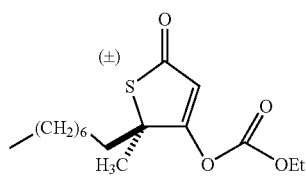

General Procedure K. (±)-4-Carbonic acid ethyl ester-5-methyl-5-octyl-5H-thiophen-2-one (61). To a solution of 32 (95 mg, 0.39 mmol) in THF (1.8 mL) cooled to −78° C. was added LiHMDS (0.58 mL, 0.58 mmol, 1 M in THF) and the solution was allowed to stir for 30 minutes at −78° C. Ethyl chloroformate (60 µL, 0.62 mmol) was then added and the mixture was transferred to an ice bath and then allowed to slowly warm to room temperature. After 1 hour at room temperature the mixture was poured into a solution of HCl (1 N)/NH$_4$Cl$_{(sat)}$ (10 mL) and extracted with Et$_2$O (3×10 mL). The combined organics were dried (MgSO$_4$), filtered, evaporated and chromatographed (20% EtOAc/Hexanes) to give pure 61 (111 mg, 91%). $^1$H NMR (300 MHz, CDCl$_3$) δ 0.85 (t, J=6.9 Hz, 3H), 1.12-1.17 (m, 11H), 1.38 (t, J=7 Hz, 3H), 1.42-1.50 (m, 1H), 1.67 (s, 3H), 1.82 (d, J=9 Hz, 1H), 1.85 (d, J=9 Hz, 1H), 4.33 (q, J=7 Hz, 2H), 6.38 (s, 1H); $^{13}$C NMR (75 MHz, CDCl$_3$) δ 14.0, 14.0, 22.6, 25.2, 25.8, 29.1, 29.2, 20.4, 31.8, 38.4, 60.1, 66.0, 112.8, 150.2, 175.6, 193.9. IR (NaCl) 2928, 1782, 1690, 1625 cm$^{-1}$. Analysis Calculated for C$_{16}$H$_{26}$O$_4$S: C, 61.1; H, 8.33; Found: C, 61.5; H, 8.32.

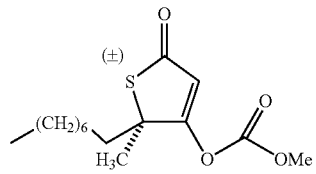

(±)-4-Carbonic acid methyl ester-5-methyl-5-octyl-5H-thiophen-2-one (62). From 32 (73 mg, 0.30 mmol) and methyl chloroformate (37 µL, 0.48 mmol) following general procedure K was obtained 62 (63 mg, 70%) after flash chromatography (20% EtOAc/Hexanes). $^1$H NMR (300 MHz, CDCl$_3$) δ 0.85 (t, J=7 Hz, 3H), 1.15-1.21 (m, 1H), 1.22 (s, 10H), 1.41-1.51 (m, 1H), 1.66 (s, 3H), 1.81 (d, J=9 Hz, 1H), 1.83 (d, J=9 Hz, 1H), 3.92 (s, 3H), 6.39 (s, 1H); $^{13}$C NMR (75 MHz, CDCl$_3$) δ 14.1, 22.6, 25.2, 25.9, 29.2, 29.3, 29.4, 31.8, 38.4, 56.2, 60.2, 112.9, 150.9, 175.5, 194.1. IR (NaCl) 3382, 1626, 1560, 1542 cm$^{-1}$. Analysis Calculated for C$_{15}$H$_{24}$O$_4$S: C, 59.9; H, 8.05; Found: C, 60.3; H, 8.10.

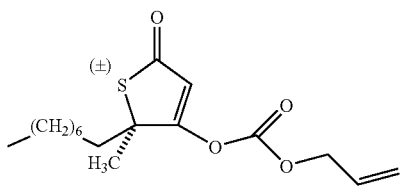

(±)-4-Carbonic acid allyl ester-5-methyl-5-octyl-5H-thiophen-2-one (63). From 32 (51.5 mg, 0.21 mmol) and allyl chloroformate (33 µL, 0.32 mmol) following general procedure K was obtained 63 (46.3 mg, 67%) after flash chromatography (15% EtOAc/Hexanes). $^1$H NMR (300 MHz, CDCl$_3$) δ 0.85 (t, J=7, 3H), 1.16-1.23 (bs, 10H), 1.41-1.51 (m, 2H), 1.67 (s, 3H), 1.81-1.87 (m, 2H), 4.74 (app dt, J=6, 1.3 Hz, 2H), 5.37 (app dq, J=10.3, 1.02 Hz, 1H), 5.44 (app dq, J=15.9, 1.02 Hz, 1H), 5.90-6.0 (m, 1H), 6.39 (s, 1H); $^{13}$C NMR (75 MHz, CDCl$_3$) 14.0, 22.6, 25.2, 25.8, 29.1, 29.2, 29.4, 31.8, 38.4, 60.1, 70.2, 112.9, 120.6, 130.23, 150.0, 175.5, 193.7. IR (NaCl) 2927, 1782, 1691, 1606 cm$^{-1}$. Analysis Calculated for C$_{17}$H$_{26}$O$_4$S: C, 62.5; H, 8.03; Found: C, 62.6; H, 8.07.

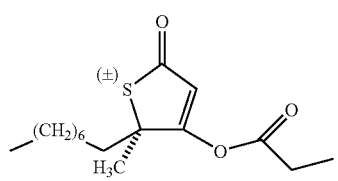

(±)-4-Propionyl-5-methyl-5-octyl-5H-thiophen-2-one (64). From 32 (40 mg, 0.17 mmol) and propionyl chloride (20

μL, 0.22 mmol) following general procedure K was obtained 64 (23.1 mg, 47%) after flash chromatography (15% EtOAc/Hexanes). $^1$H NMR (300 MHz, CDCl$_3$) δ 0.85 (t, J=7 Hz, 3H), 1.12-1.25 (m, 13H), 1.42-1.49 (m, 2H), 1.64 (s, 3H), 1.78-1.84 (m, 2H), 2.57 (q, J=7.5 Hz, 2H), 6.39 (s, 1H); $^{13}$C NMR (75 MHz, CDCl$_3$) δ 8.71, 14.0, 22.6, 25.1, 25.9, 27.9, 29.1, 29.3, 29.5, 31.8, 38.6, 60.4, 113.8, 169.1, 177.0, 179.9. IR (NaCl) 2928, 1787, 1688 cm$^{-1}$; Analysis Calculated for C$_{16}$H$_{26}$O$_3$S: C, 64.4; H, 8.78; Found: C, 64.3; H, 8.89.

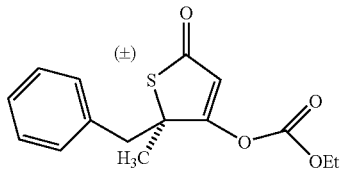

65

(4)-4-carbonic acid ethyl-ester-5-phenyl-5-methyl-5H-thiophen-2-one (65). From 22 (50 mg, 0.23 mmol) and ethyl chloroformate (35 μL, 0.36 mmol) following general procedure K was obtained 65 (67 mg, 88%). $^1$H NMR (300 MHz, CDCl$_3$) δ 1.31 (t, J=7 Hz, 3H), 1.69 (s, 3H), 3.15 (s, 2H), 4.36 (q, J=7 Hz, 2H), 6.33 (s, 1H), 7.18-7.27 (m, 5H); $^{13}$C NMR (75 MHz, CDCl$_3$) δ 14.1, 25.3, 44.6, 60.6, 66.2, 113.2, 127.4, 128.2, 130.3, 135.4, 150.1, 175.1, 193.3.

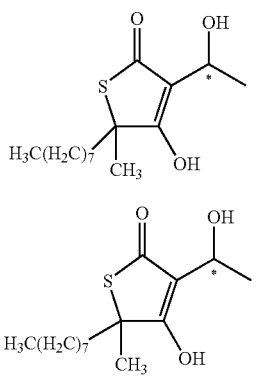

66

67

(±)-4-Hydroxy-3-(1-hydroxyethyl)-5-methyl-5-octyl-5H-thiophen-2-one. (66, 67). To 32 (247 mg, 1.02 mmol) dissolved in hexanes was added triethylamine (0.23 mL, 1.68 mmol) and trimethylsilylchloride (0.21 mL, 1.64 mmol) and the solution was allowed to stir at room temperature for 4 h. The mixture was filtered over celite and evaporated to provide 5-methyl-5-octyl-4-trimethylsilanyloxy-5-H-thiopen-2-one. To a solution of TiCl$_4$ (0.7 mL, 0.7 mmol) in CH$_2$Cl$_2$ (1.95 mL) at -78° C. was added acetaldehyde (54 μL, 0.97 mmol) and this solution was allowed to stir for 5 min at -78° C. Then, 5-methyl-5-octyl-4-trimethylsilanyloxy-5-H-thiopen-2-one dissolved in CH$_2$Cl$_2$ (0.4 mL) was cannulated into TiCl$_4$/acetaldehyde solution giving a bright orange color. This mixture was allowed to warm and stir for 20 min at 0° C. The mixture was poured into NH$_4$Cl$_{(sat)}$ (15 mL) and extracted with CH$_2$Cl$_2$ (3×15 mL). The organics were combined, dried (MgSO$_4$), filtered and evaporated. Flash chromatography (10% EtOAc/Hexanes) provided pure 66 (34 mg) and 67 (24 mg) (50%). (66) $^1$H NMR (300 MHz, CDCl$_3$) δ 0.86 (t, J=6.9 Hz, 3H), 1.05-1.08 (m, 1H), 1.24 (bs, 11H), 1.49 (d, J 6.5 Hz, 3H, rotamer) 1.55 (d, J=5.2 Hz, 3H, rotamer), 1.62 (s, 3H), 1.78-1.82 (m, 2H), 4.68 (q, J=6.5 Hz, 1H, rotamer), 5.04 (q, J=5.2 Hz, 1H, rotamer). HRMS (ES) m/z calculated for C$_{16}$H$_{28}$O$_3$SNa$^+$ (M+CH$_2$+Na$^+$) 323.1660 obsd. 323.1660.

(67) $^1$H NMR (300 MHz, CDCl$_3$) δ 0.85 (t, J=6.9 Hz, 3H), 1.24 (bs, 12H), 1.47 (d, J=6.6 Hz, 3H, rotamer), 1.54 (d, J=5.4 Hz, 3H, rotamer), 1.59 (s, 3. H), 1.76-1.82 (m, 2H), 4.65 (q, J=6.3 Hz, 1H), 5.06 (q, J=5.4 Hz, 1H). HRMS (ES) m/z calculated for C$_{16}$H$_{28}$O$_3$SNa$^+$ M+CH$_2$+Na$^+$) 323.1660 obsd. 323.1660.

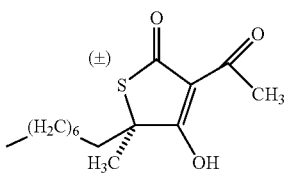

68

General Procedure L. 3-Alkynyl-4-hydroxy-5-methyl-5-octyl-5H-thiophen-2-one. (68). To 32 (94 mg, 0.38 mmol) in CH$_2$Cl$_2$ (1.9 mL) at 0° C. was added NEt$_3$ (58 μL, 0.42 mmol), dimethylaminopyridine (DMAP) (19 mg, 0.15 mmol) and acetic anhydride (43 μL, 0.47 mmol). The solution stirred at 0° C. for 15 min then was allowed to warm and stir at room temperature for 2-14 h or until TLC indicated completion of the reaction. The mixture was poured into NH$_4$Cl(sat)/HCl (1 N) (3:1, 8 mL) and extracted with CH$_2$Cl$_2$ (3×10 mL). The organics were combined, dried (MgSO$_4$), filtered and evaporated to giver crude 68. Flash chromatography 30% EtOAc/2°% AcOH/Hex (rf=0.44) gave pure 68 (83 mg, 78%). $^1$H NMR (300 MHz, CDCl$_3$) δ 0.84 (m, 3H), 1.22 (bs, 10H), 1.48 (m, 2H), 1.65 (s, 3H), 1.77-1.92 (m, 2H), 2.55 (s, 3H). $^{13}$C NMR (75 MHz, CDCl$_3$) δ 13.9, 22.6, 23.8, 25.1, 26.3, 29.1, 29.2, 29.5, 31.7, 39.4, 59.7, 109.7, 190.5, 195.5, 204.9. HRMS (EI) m/z calculated for C$_{15}$H$_{24}$O$_3$S$^+$ (M$^+$) 284.1441 obsd. 284.1414.

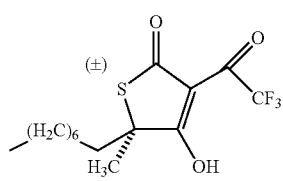

69

4-Hydroxy-5-methyl-5-octyl-3-(2,2,2-trifluoro-alkynyl)-5H-thiophen-2-one. (69). To 32 (90 mg, 0.37 mmol), trifluoroacetic anhydride (114 μL, 0.81 mmol), dimethylaminopyridine (DMAP) (18 mg, 0.15 mmol) and NEt$_3$ (108 μL, 0.77 mmol) following General Procedure L was obtained 69 (107 mg, 86%) after flash chromatography (40% Hex/10% THF/2% AcOH/EtOAc). 1H NMR (300 MHz, MeOD) d 0.85 (t, J=6.9 Hz, 3H), 1.09 (m, 1H), 1.21 (bs, 1H), 1.38 (s, 3H), 1.51-1.60 (m, 1H), 1.65-1.71 (m, 1H). HRMS (EI) m/z calculated for C$_{15}$H$_{21}$F$_3$O$_3$S$^+$ (M$^+$) 338.1158 obsd. 338.1171.

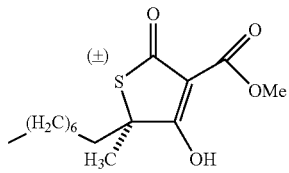

4-Hydroxy-5-methyl-5-octyl-2-oxo-2,5-dihydro-thiophene-3-carboxylic acid methyl ester (70). To 32 (91 mg, 0.37 mmol), methyl chloroformate (63 μL, 0.81 mmol), dimethylaminopyridine (DMAP) (23 mg, 0.18 mmol) and NEt₃ (108 μL, 0.77 mmol) following General Procedure L was obtained 70 (66 mg, 59%, 79% based on recovered starting material) after flash chromatography (30% EtOAc/2% AcOH/Hexanes-10% THF/2% AcOH/EtOAc). $^1$H NMR (300 MHz, MeOD) δ 0.86 (t, J=6.9 Hz, 3H), 1.20 (bs, 12H), 1.35 (s, 3H), 1.55 (m, 1H), 1.71-1.75 (m, 1H), 3.59 (s, 3H); $^{13}$C NMR (75 MHz, MeOD) δ 13.3, 21.8, 24.4, 27.0, 28.5, 28.6, 29.0, 30.2, 31.0, 50.4, 58.3, 124.6, 168.1, 187.7, 196.7. HRMS (EI) m/z calculated for $C_{15}H_{24}O_4S+$) 300.1389 obsd. 300.1375.

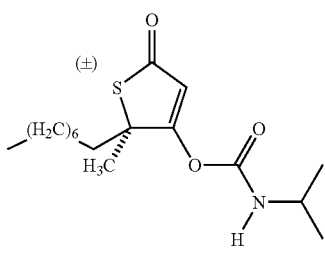

Isopropyl-carbamic acid 2-methyl-2-octyl-5-oxo-2,5-dihydro-thiophen-3-yl ester (71). To 32 (46 mg, 0.19 mmol) dissolved in hexanes was added triethylamine (43 μL, 0.31 mmol) and trimethylsilylchloride (36 μL, 0.29 mmol) and the solution was allowed to stir at room temperature for 4 h. The mixture was filtered over celite and evaporated to provide 5-methyl-5-octyl-4-trimethylsilanyloxy-5-H-thiopen-2-one which was redissolved in CH₂Cl₂ (0.4 mL). To this mixture was added isopropyl isocyanate (19.2 mL, 0.19 mmol) and the solution was allowed to stir at room temperature for 2 hours. NH4Cl(sat) (5 mL) was added and the mixture was extracted with CH₂Cl₂ (3×10 mL). The organics were combined, dried (MgSO₄), filtered and evaporated to give crude 71. Flash chromatography (20% EtOAc/2% AcOH/Hexanes) gave pure 71 (35 mg, 60%). $^1$H NMR (300 MHz, CDCl₃) δ 0.85 (t, J=7.0 Hz, 3H), 1.14-1.24 (m, 17H), 1.45 (m, 1H), 1.63 (s, 3H), 1.76-1.79 (m, 2H), 3.81-3.88 (m, 1H), 5.16 (d, J=7 Hz, 1H), 6.33 (s, 1H). $^{13}$C NMR (75 MHz, CDCl₃) δ 13.9, 20.4, 22.5, 22.8, 25.1, 25.9, 29.1, 29.3, 29.5, 31.8, 38.7, 44.0, 60.2, 111.6, 149.7, 176.2, 194.5.

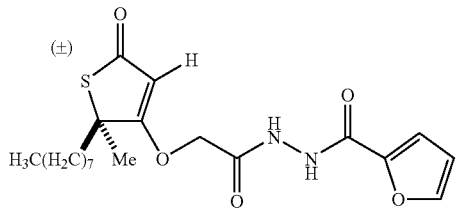

General Procedure M. (±)-(5-Methyl-5-octyl-2-oxo-thiophen-4-yloxy)-acetic-acid-N'-(2-furoic)-hydrazide (72). To a cooled solution (0° C.) of 53 (100 mg, 0.33 mmol) in CH₂Cl₂ (1.61 mL) was added 1-[3-(dimethylamino)propyl]-3-ethylcarbodiimide hydrochloride EDC) (128 mg, 0.43 mmol), DMAP (6.0 mg, 0.05 mmol), and 2-furoic hydrazide (54 mg, 0.43 mmol). This mixture stirred at 0° C. for 30 minutes, then was allowed to warm to room temperature and stir for 12 h. The solution was poured into NH₄Cl (10 ml, sat) and extracted with CH₂Cl₂ (3×10 ml). The combined organics were dried (Na₂SO₄), filtered and evaporated to give crude 72. Flash chromatography (10% EtOAc/Hex) gave pure 72 (91 mg, 68%). $^1$H NMR (400 MHz, CDCl₃) δ 0.84 (t, J=6.6 Hz, 3H), 1.21 (m, 11H), 1.43-1.47 (m, 1H), 1.66 (s, 3H), 1.81-1.86 (m, 2H), 4.64 (s, 2H), 5.42 (s, 1H), 6.47 (dd, J=1.6, 3.6 Hz, 1H), 7.16 (d, J=4 Hz, 1H), 7.45 (m, 1H), 9.32 (d, J=4 Hz, 1H), 9.44 (d, J=4 Hz, 1H); $^{13}$C NMR (100 MHz, CDCl₃) δ 14.0, 22.6, 25.3, 26.0, 29.2, 29.3, 29.5, 31.7, 38.8, 59.7, 69.1, 103.0, 112.3, 116.5, 145.1, 145.4, 156.4, 164.2, 184.8, 193.9.

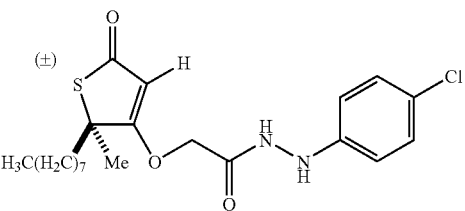

(±)-(5-Methyl-5-octyl-2 oxo-thiophen-4-yloxy)-acetic-acid-N'-acetylhydrazide (73). To 53 (100 mg, 0.33 mmol) and acetic hydrazide (26.8 mg, 0.36 mmol) following General Procedure M was obtained 73 (70.4 mg, 60%) after flash chromatography (2% AcOH/EtOAc). $^1$H NMR (400 MHz, CDCl₃) δ 0.85 (t, J=7.2 Hz, 3H), 1.23 (m, 11H), 1.48-1.52 (m, 1H), 1.67 (s, 3H), 1.84-1.86 (m, 2H), 2.07 (s, 3H), 4.64 (s, 2H), 5.42 (s, 1H). $^{13}$C NMR (100 MHz, CDCl₃) δ 14.1, 20.6, 22.6, 25.2, 26.0, 29.2, 29.3, 29.5, 31.8, 38.8, 59.8, 68.9, 102.9, 163.1, 168.1, 184.9, 194.2.

(±)-(5-Methyl-5-octyl-2-oxo-thiophen-4-yloxy)-acetic-acid-N'-(4-chloro-phenyl)-hydrazide (74) To 53 (100 mg, 0.33 mmol) and 4-chlorophenylhydrazine hydrochloride (76.8 mg, 0.43 mmol) following General Procedure M was obtained 74 (74 mg, 53%) after flash chromatography (50% EtOAc/Hex). $^1$H NMR (300 MHz, CDCl$_3$) δ 0.86 (t, J=6 Hz, 3H), 1.24 (m, 11H), 1.46-1.54 (m, 1H), 1.71 (s, 3H), 1.82-1.90 (m, 2H), 4.57 (s, 2H), 5.39 (s, 1H), 6.75 (d, J=8.8 Hz, 2H), 7.18 (d, J=8.8 Hz, 2H), 7.38 (s, 1H), 8.09 (s, 1H); $^{13}$C NMR (100 MHz, CDCl$_3$) δ 14.1, 22.6, 25.3, 26.1, 29.2, 29.3, 29.5, 31.8, 38.8, 59.7, 69.7, 103.2, 114.7, 126.4, 145.8, 129.2, 165.9, 184.3, 193.5. IR (NaCl) 2957, 1695, 1658, 1609 cm$^{-1}$.

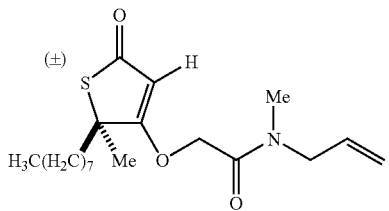

75

(±)—N-Allyl-N-methyl-(5-Methyl-5-octyl-2-oxo-thiophen-4-yloxy)-acetamide (75). To 53 (83 mg, 0.28 mmol) and N-methyl,N-allyalmine (29 µL, 0.30 mmol) following General Procedure M was obtained 75 (51 mg, 52%) after flash chromatography (40% EtOAc/Hex). $^1$H NMR (300 MHz, CDCl$_3$) δ 0.83 (t, J=6.9 Hz, 3H), 1.22 (m, 11H), 1.43-1.47 (m, 1H), 1.67 (s, 3H), 1.82-1.86 (m, 2H), rotamer 1: 2.91 (s, 3H), rotamer 2: 2.95 (s, 3H), rotamer 1: 3.84 (d, J=4.8 Hz, 2H), rotamer 2: 3.98 (d, J=6 Hz, 2H), rotamer 1: 4.62 (s, 2H), rotamer 2: 4.65 (s, 2H), 5.12-5.28 (m, 2H), rotamer 1: 5.18 (s, 1H), rotamer 2: 5.25 (s, 1H), 5.65-5.81 (m, 1H); $^{13}$C NMR (100 MHz, CDCl$_3$) δ 14.0, 22.5, 25.1, 26.2, 29.1, 29.3, 29.4, 31.7, 33.4 (rotamer 2: 33.9), 38.8, 50.2 (rotamer 2: 51.0), 59.7, 69.0 (rotamer 2: 69.3), 102.3, 117.4 (rotamer 2: 118.2), 131.6 (rotamer 2: 131.8), 164.5 (rotamer 2: 164.9), 185.5 (rotamer 2: 185.6), 193.4.

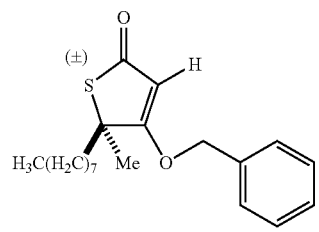

76

(±)-4-Benzyloxy-3,5-dimethyl-5-octyl-5-H-thiophen-2-one (76). To 32 (50 mg, 0.21 mmol) and benzyl bromide (37 mL, 0.31 mmol) following General Procedure H, was obtained 76 (49 mg, 75%) after flash chromatography (15% EtOAc/Hex). $^1$H NMR (300 MHz, CDCl$_3$) δ 0.86 (t, J=6.9 Hz, 3H), 1.24 (m, 11H), 1.41-1.48 (m, 1H), 1.66 (s, 3H), 1.79-1.86 (m, 2H), 4.98 (s, 2 H), 5.39 (s, 1H), 7.31-7.42 (m, 5H); $^{13}$C NMR (100 MHz, CDCl$_3$) δ 14.1, 22.6, 25.0, 26.4, 29.1, 29.3, 29.4, 31.8, 38.8, 59.7, 74.0, 102.2, 127.6, 128.8, 128.8, 134.3, 185.8, 194.1. IR (NaCl) 2928, 1681, 1610 cm$_{-1}$.

REFERENCES

1. Strijtveen, B.; Kellogg, R. M. *Tetrahedron*. 1987, 43, 5039-5054.
2. Sasaki, H.; Oishi, H.; Hayashi, T.; Matsuura, I.; Ando K.; Sawada, M. *J. Antibiotics* 1982,
3. Kunieda, T.; Nagamatsu, T.; Higuchi, T.; Hirobe, M. *Tetrahedron Lett.* 1988, 29, 2203-2206.

Biological and Biochemical Methods

Purification of FAS from ZR-75-1 Human Breast Cancer Cells.

Human FAS was purified from cultured ZR-75-1 human breast cancer cells obtained from the American Type Culture Collection. The procedure, adapted from Linn et al., 1981, and Kuhajda et al., 1994, utilizes hypotonic lysis, successive polyethyleneglycol (PEG) precipitations, and anion exchange chromatography. ZR-75-1 cells are cultured at 37° C. with 5% CO$_2$ in RPMI culture medium with 10% fetal bovine serum, penicillin and streptomycin.

Ten T150 flasks of confluent cells are lysed with 1.5 ml lysis buffer (20 mM Tris-HCl, pH 7.5, 1 mM EDTA, 0.1 mM phenylmethanesulfonyl fluoride (PMSF), 0.1% Igepal CA-630) and dounce homogenized on ice for 20 strokes. The lysate is centrifuged in JA-20 rotor (Beckman) at 20,000 rpm for 30 minutes at 4° C. and the supernatant is brought to 42 ml with lysis buffer. A solution of 50% PEG 8000 in lysis buffer is added slowly to the supernatant to a final concentration of 7.5%. After rocking for 60 minutes at 4° C., the solution is centrifuged in JA-20 rotor (Beckman) at 15,000 rpm for 30 minutes at 4° C. Solid PEG 8000 is then added to the supernatant to a final concentration of 15%. After the rocking and centrifugation is repeated as above, the pellet is resuspended overnight at 4° C. in 10 ml of Buffer A (20 mM K$_2$HPO$_4$, pH 7.4). After 0.45 µM filtration, the protein solution is applied to a Mono Q 5/5 anion exchange column (Pharmacia). The column is washed for 15 minutes with buffer A at 1 ml/minute, and bound material is eluted with a linear 60-ml gradient over 60 minutes to 1 M KCl. FAS (MW~270 kD) typically elutes at 0.25 M KCl in three 0.5 ml fractions identified using 4-15% SDS-PAGE with Coomassie G250 stain (Bio-Rad). FAS protein concentration is determined using the Coomassie Plus Protein Assay Reagent (Pierce) according to manufacturer's specifications using BSA as a standard. This procedure results in substantially pure preparations of FAS (>95%) as judged by Coomassie-stained gels.

Measurement of FAS Enzymatic Activity and Determination of the IC$_{50}$ of the Compounds FAS activity is measured by monitoring the malonyl-CoA dependent oxidation of NADPH spectrophotometrically at OD$_{340}$ in 96-well plates (Dils et al and Arslanian et al, 1975). Each well contains 2 µg purified FAS, 100 mM K$_2$HPO$_4$, pH 6.5, 1 mM dithiothreitol (Sigma), and 187.5 µM β-NADPH (Sigma). Stock solutions of inhibitors are prepared in DMSO at 2, 1, and 0.5 mg/ml resulting in final concentrations of 20, 10, and 5 µg/ml when 1 µl of stock is added per well. For each experiment, cerulenin (Sigma) is run as a positive control along with DMSO controls, inhibitors, and blanks (no FAS enzyme) all in duplicate.

The assay is performed on a Molecular Devices Spectra-Max Plus Spectrophotometer. The plate containing FAS, buffers, inhibitors, and controls are placed in the spectrophotometer heated to 37° C. Using the kinetic protocol, the wells are blanked on duplicate wells containing 100 μl of 100 mM $K_2HPO_4$, pH 6.5 and the plate is read at $OD_{340}$ at 10 sec intervals for 5 minutes to measure any malonyl-CoA independent oxidation of NADPH. The plate is removed from the spectrophotometer and malonyl-CoA (67.4 μM, final concentration per well) and alkynyl-CoA (61.8 μM, final concentration per well) are added to each well except to the blanks. The plate is read again as above with the kinetic protocol to measure the malonyl-CoA dependent NADPH oxidation. The difference between the $\Delta$ $OD_{340}$ for the malonyl-CoA dependent and non-malonyl-CoA dependent NADPH oxidation is the specific FAS activity. Because of the purity of the FAS preparation, non-malonyl-CoA dependent NADPH oxidation is negligible.

The $IC_{50}$ for the compounds against FAS is determined by plotting the $\Delta$ $OD_{340}$ for each inhibitor concentration tested, performing linear regression and computing the best-fit line, $r^2$ values, and 95% confidence intervals. The concentration of compound yielding 50% inhibition of FAS is the $IC_{50}$. Graphs of $\Delta$ $OD_{340}$ versus time are plotted by the SOFTmax PRO software (Molecular Devices) for each compound concentration. Computation of linear regression, best-fit line, $r^2$, and 95% confidence intervals are calculated using Prism Version 3.0 (Graph Pad Software).

Crystal Violet Cell Growth Assay

The crystal violet assay measure cell growth but not cytotoxicity. This assay employs crystal violet staining of fixed cells in 96-well plates with subsequent solubilization and measurement of $OD_{490}$ on a spectrophotometer. The $OD_{490}$ corresponds to cell growth per unit time measured. Cells are treated with the compounds of interest or vehicle controls and $IC_{50}$ for each compound is computed.

To measure the cytotoxicity of specific compounds against cancer cells, $5 \times 10^4$ MCF-7 human breast cancer cells, obtained from the American Type Culture Collection are plated per well in 24 well plates in DMEM medium with 10% fetal bovine serum, penicillin, and streptomycin. Following overnight culture at 37° C. and 5% $CO_2$, the compounds to be tested, dissolved in DMSO, are added to the wells in 1 μl volume at the following concentrations: 50, 40, 30, 20, and 10 μg/ml in triplicate. Additional concentrations are tested if required. 1 μl of DMSO is added to triplicate wells are the vehicle control. C75 is run at 10, and 5 μg/ml in triplicate as positive controls.

After 72 hours of incubation, cells are stained with 0.5 ml of Crystal Violet stain (0.5% in 25% methanol) in each well. After 10 minutes, wells are rinsed, air dried, and then solubilized with 0.5 ml 10% sodium dodecylsulfate with shaking for 2 hours. Following transfer of 100 μL from each well to a 96-well plate, plates are read at $OD_{490}$ on a Molecular Devices SpectraMax Plus Spectrophotometer Average $OD_{490}$ values are computed using SOFTmax Pro Software (Molecular Devices) and $IC_{50}$ values are determined by linear regression analysis using Prism version 3.02 (Graph Pad Software, San Diego).

XTT Cytotoxicity Assay

The XTT assay is a non-radioactive alternative for the [$^{51}$Cr] release cytotoxicity assay. XTT is a tetrazolium salt that is reduced to a formazan dye only by metabolically active, viable cells. The reduction of XTT is measured spectrophotometrically as $OD_{490}$-$OD_{650}$.

To measure the cytotoxicity of specific compounds against cancer cells, $9 \times 10^3$ MCF-7 human breast cancer cells, obtained from the American Type Culture Collection are plated per well in 96 well plates in DMEM medium with 10% fetal bovine serum, insulin, penicillin, and streptomycin. Following overnight culture at 37° C. and 5% $CO_2$, the compounds to be tested, dissolved in DMSO, are added to the wells in 1 μl volume at the following concentrations: 80, 40, 20, 10, 5, 2.5, 1.25, and 0.625 μg/ml in triplicate. Additional concentrations are tested if required. 1 μl of DMSO is added to triplicate wells are the vehicle control. C75 is run at 40, 20, 10, 15, 12.5, 10, and 5 μg/ml in triplicate as positive controls. After 72 hours of incubation, cells are incubated for 4 hours with the XTT reagent as per manufacturer's instructions (Cell Proliferation Kit II (XTT) Roche). Plates are read at $OD_{490}$ and $OD_{650}$ on a Molecular Devices SpectraMax Plus Spectrophotometer. Three wells containing the XTT reagent without cells serve as the plate blank. XTT data are reported as $OD_{490}$-$OD_{650}$-Averages and standard error of the mean are computed using SOFTmax Pro software (Molecular Dynamics).

The $IC_{50}$ for the compounds is defined as the concentration of drug leading to a 50% reduction in $OD_{490}$-$OD_{650}$ compared to controls. The $OD_{490}$-$OD_{650}$ are computed by the SOFTmax PRO software (Molecular Devices) for each compound concentration. $IC_{50}$ is calculated by linear regression, plotting the FAS activity as percent of control versus drug concentrations. Linear regression, best-fit line, $r^2$, and 95% confidence intervals are determined using Prism Version 3.0 (Graph Pad Software).

Measurement of [$^{14}$C]acetate Incorporation into Total Lipids and Determination of $IC_{50}$ of Compounds This assay measures the incorporation of [$^{14}$C]acetate into total lipids and is a measure of fatty acid synthesis pathway activity in vitro. It is utilized to measure inhibition of fatty acid synthesis in vitro.

MCF-7 human breast cancer cells cultured as above, are plated at $5 \times 10^4$ cells per well in 24-well plates. Following overnight incubation, the compounds to be tested, solubilized in DMSO, are added at 5, 10, and 20 μg/ml in triplicate, with lower concentrations tested if necessary. DMSO is added to triplicate wells for a vehicle control. C75 is run at 5 and 10 μg/ml in triplicate as positive controls. After 4 hours of incubation, 0.25 μCi of [$^{14}$C]acetate (10 μl volume) is added to each well.

After 2 hours of additional incubation, medium is aspirated from the wells and 800 μl of chloroform:methanol (2:1) and 700 μl of 4 mM $MgCl_2$ is added to each well. Contents of each well are transferred to 1.5 Eppendorf tubes, and spun at full-speed for 2 minutes in a high-speed Eppendorf Microcentrifuge 5415D. After removal of the aqueous (upper) layer, an additional 700 μl of chloroform:methanol (2:1) and 500 μl of 4 mM $MgCl_2$ are added to each tube and then centrifuged for 1 minutes as above. The aqueous layer is removed with a Pasteur pipette and discarded. An additional 400 μl of chloroform:methanol (2:1) and 200 μl of 4 mM $MgCl_2$ are added to each tube, then centrifuged and aqueous layer is discarded.

The lower (organic) phase is transferred into a scintillation vial and dried at 40° C. under $N_2$ gas. Once dried, 3 ml of scintillant (APB #NBC5104) is added and vials are counted for $^{14}C$. The Beckman Scintillation counter calculates the average cpm values for triplicates.

The $IC_{50}$ for the compounds is defined as the concentration of drug leading to a 50% reduction in $[^{14}C]$acetate incorporation into lipids compared to controls. This is determined by plotting the average cpm for each inhibitor concentration tested, performing linear regression and computing the best-fit line, $r^2$ values, and 95% confidence intervals. The average cpm values are computed by the Beckman scintillation counter (Model LS6500) for each compound concentration. Computation of linear regression, best-fit line, $r^2$, and 95% confidence intervals are calculated using Prism Version 3.0 (Graph Pad Software).

Carnitine Palmitoyltransferase-1 (CPT-1) Assay

CPT-1 catalyzes the ATP dependent transfer of long-chain fatty acids from acyl-CoA to acyl-carnitine that is inhibited by malonyl-CoA. As CPT-1 requires the mitochondrial membrane for activity, enzyme activity is measured in permeabilized cells or mitochondria. This assay uses permeabilized cells to measure the transfer of [methyl-$^{14}C$]L-carnitine to the organically soluble acyl-carnitine derivative.

MCF-7 cells are plated in DMEM with 10% fetal bovine serum at $10^6$ cells in 24-well plates in triplicate for controls, drugs, and malonyl-CoA. Two hours before commencing the assay, drugs are added at the indicated concentrations made from stock solutions at 10 mg/ml in DMSO, vehicle controls consist of DMSO without drug. Since malonyl-CoA cannot enter intact cells, it is only added in the assay buffer to cells that have not been preincubated with drugs. Following overnight incubation at 37° C., the medium is removed and replaced with 700 µl of assay buffer consisting of: 50 mM imidazole, 70 mM KCl, 80 mM sucrose, 1 mM EGTA, 2 mM $MgCl_2$, 1 mM DTT, 1 mM KCN, 1 mM ATP, 0.1% fatty acid free bovine serum albumin, 70 µM palmitoyl-CoA, 0.25 µCi [methyl-$^{14}C$]L-carnitine, 40 µg digitonin with drug, DMSO vehicle control, or 20 µM malonyl-CoA. The concentrations of drugs and DMSO in the assay buffer is the same as used in the 2 hr preincubation. After incubation for 6 minutes at 37° C., the reaction is stopped by the addition of 500 µl of ice-cold 4 M perchloric acid. Cells are then harvested and centrifuged at 13,000×g for 5 minutes. The pellet is washed with 500 µl ice cold 2 mM perchloric acid and centrifuged again. The resulting pellet is resuspended in 800 µl $dH_2O$ and extracted with 150 µl of butanol. The butanol phase is counted by liquid scintillation and represents the acylcarnitine derivative.

Weight Loss Screen for Novel FAS Inhibitors

Balb/C mice (Jackson Labs) are utilized for the initial weight loss screening. Animals are housed in temperature and 12 hour day/night cycle rooms and fed mouse chow and water ad lib. Three mice are utilized for each compound tested with vehicle controls in triplicate per experiment. For the experiments, mice are housed separately for each compound tested three mice to a cage. Compounds are diluted in DMSO at 10 mg/ml and mice are injected intraperitoneally with 60 mg/kg in approximately 100 µl of DMSO or with vehicle alone. Mice are observed and weighed daily; average weights and standard errors are computed with Excel (Microsoft). The experiment continues until treated animals reach their pretreatment weights.

Figure 10:
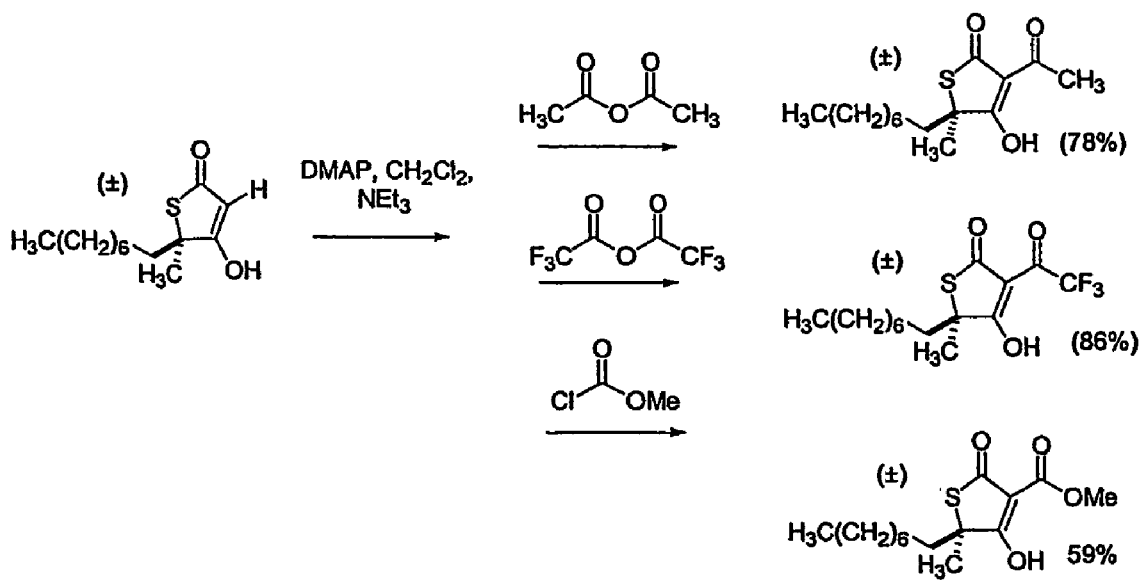
FIG. 10 shows a synthetic scheme to make certain compounds according to the invention.

Select compounds are tested in animals housed in metabolic cages. Dosing of animals are identical to the screening experiments with three animals to a single metabolic cage. Animal weights, water and food consumption, and urine and feces production are measured daily. The results for the testing of Compounds 21 and 44 are shown in FIG. 10.

Antimicrobial Properties

A broth microdilution assay is used to assess the antimicrobial activity of the compounds. Compounds are tested at twofold serial dilutions, and the concentration that inhibits visible growth ($OD_{600}$ at 10% of control) is defined as the MIC. Microorganisms tested include *Staphylococcus aureus* (ATCC # 29213), *Enterococcus faecalis* (ATCC # 29212), *Pseudomonas aeruginosa* (ATCC # 27853), and *Escherichia coli* (ATCC # 25922). The assay is performed in two growth media, Mueller Hinton Broth and Trypticase Soy Broth.

A blood (Tsoy/5% sheep blood) agar plate is inoculated from frozen stocks maintained in T soy broth containing 10% glycerol and incubated overnight at 37° C. Colonies are suspended in sterile broth so that the turbidity matches the turbidity of a 0.5 McFarland standard. The inoculum is diluted 1:10 in sterile broth (Mueller Hinton or Trypticase soy) and 195 ul is dispensed per well of a 96-well plate. The compounds to be tested, dissolved in DMSO, are added to the wells in 5 ul volume at the following concentrations: 25, 12.5, 6.25, 3.125, 1.56 and 0.78 ug/ml in duplicate. Additional concentrations are tested if required. 5 ul of DMSO added to duplicate wells are the vehicle control. Serial dilutions of positive control compounds, vancomycin (*E. faecalis* and *S. aureus*) and tobramycin (*E. coli* and *P. aeruginosa*), are included in each run.

After 24 hours of incubation at 37° C., plates are read at $OD_{600}$ on a Molecular Devices SpectraMax Plus Spectrophotometer. Average $OD_{600}$ values are computed using SOFTmax Pro Software (Molecular Devices) and MIC values are determined by linear regression analysis using Prism version 3.02 (Graph Pad Software, San Diego). The MIC is defined as the concentration of compound required to produce an $OD_{600}$ reading equivalent to 10% of the vehicle control reading.

In Vivo Testing for Anti-Tumor Activity

Figure 5:
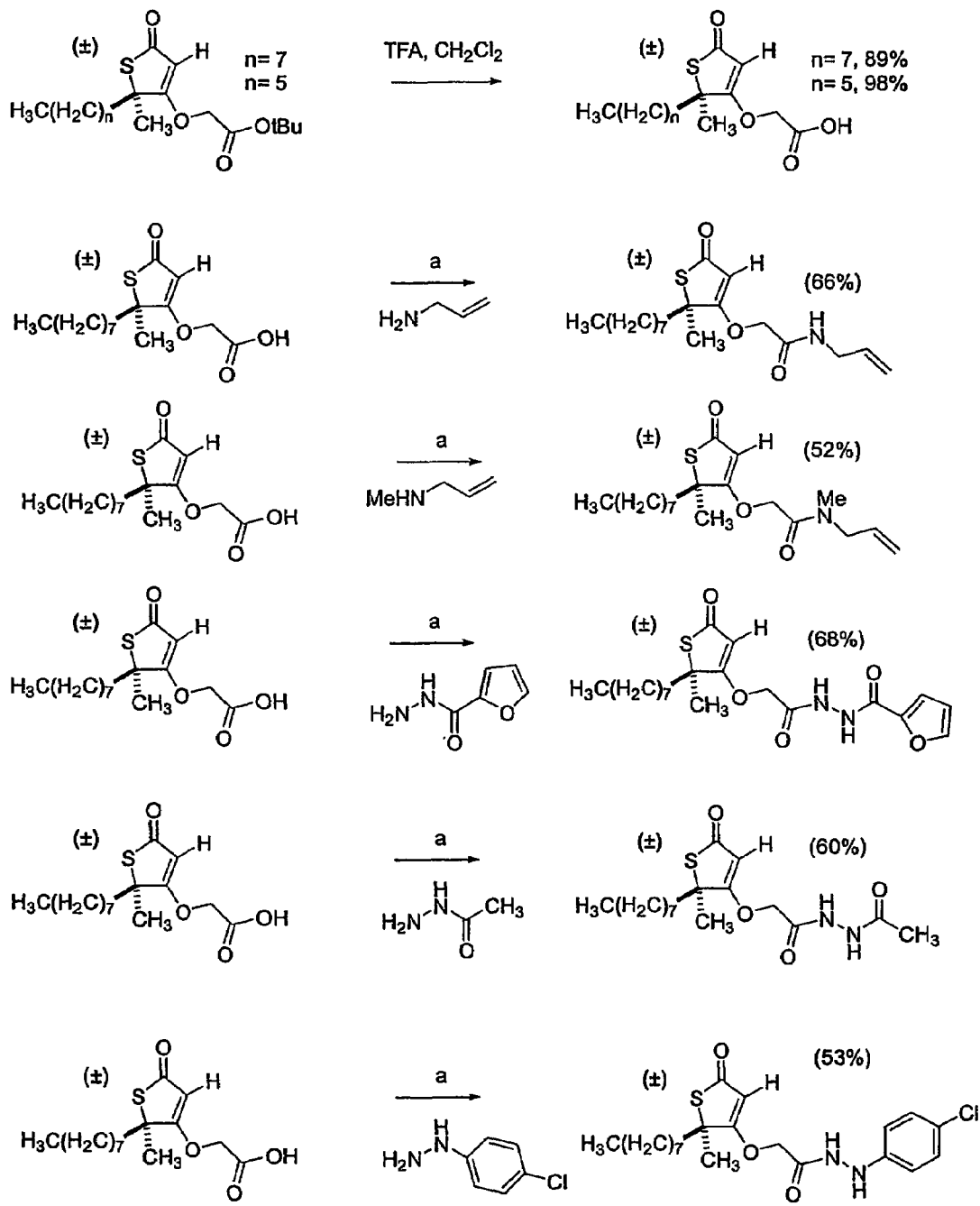
FIG. 5 shows a synthetic schemes to make certain compounds according to the invention.
Figure 6:
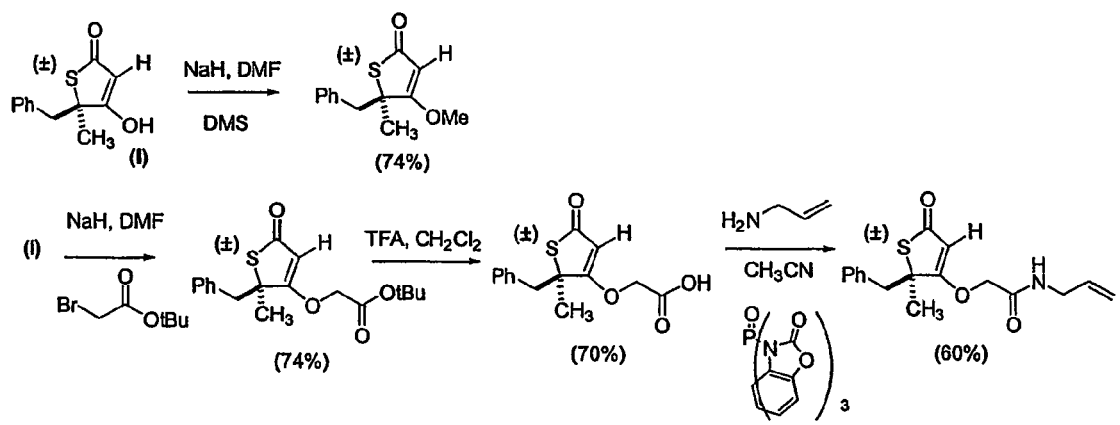
FIG. 6 shows a synthetic schemes to make certain compounds according to the invention.
Figure 7:
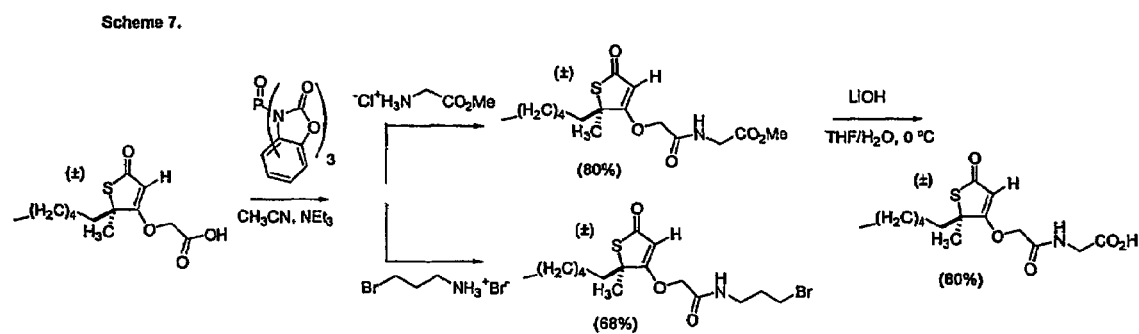
FIG. 7 shows a synthetic scheme to make a compound according to the invention.
Figure 8:
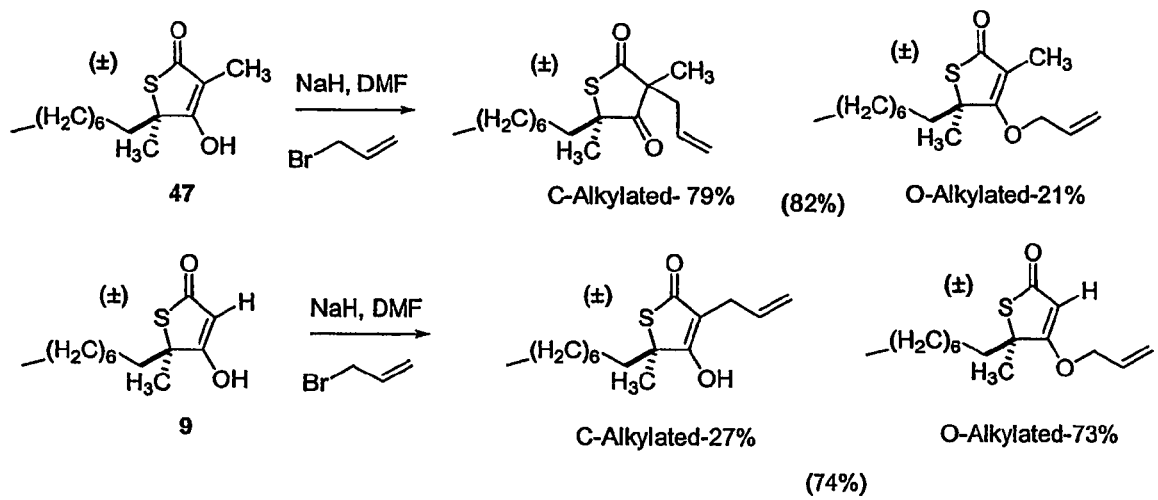
FIG. 8 shows a synthetic scheme to make certain compounds according to the invention.
Figure 9:
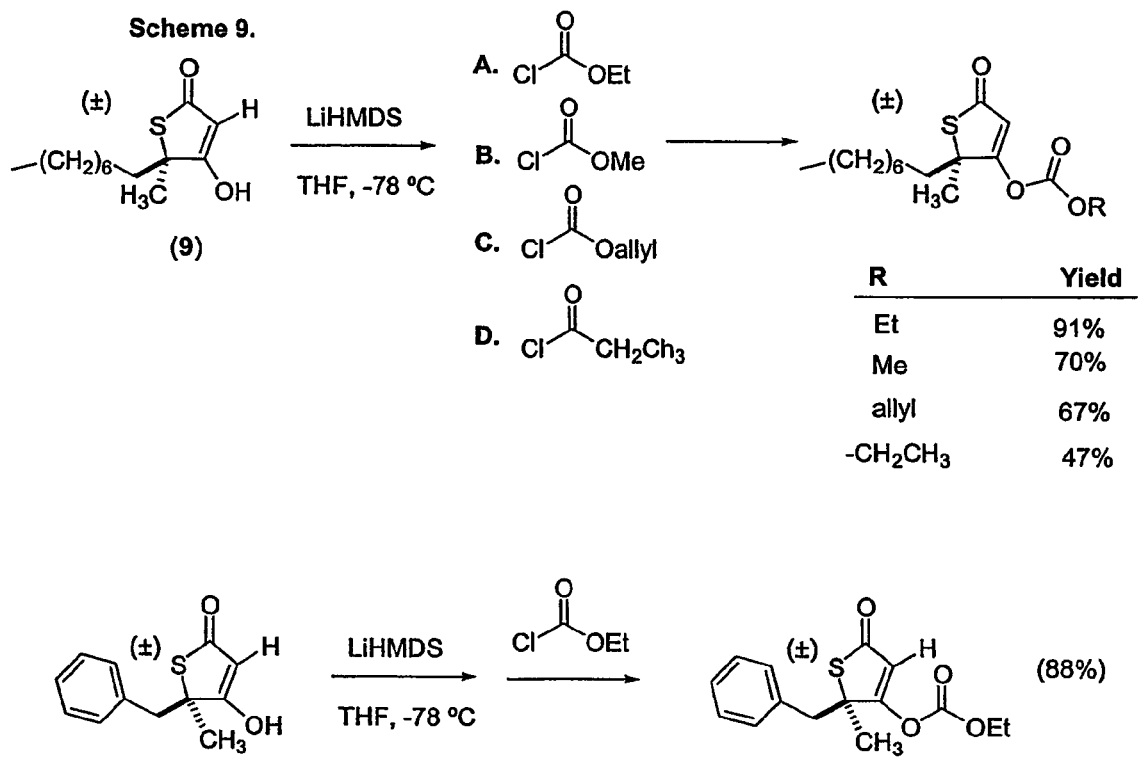
FIG. 9 shows two synthetic schemes to make certain compounds according to the invention.
Figure 11:
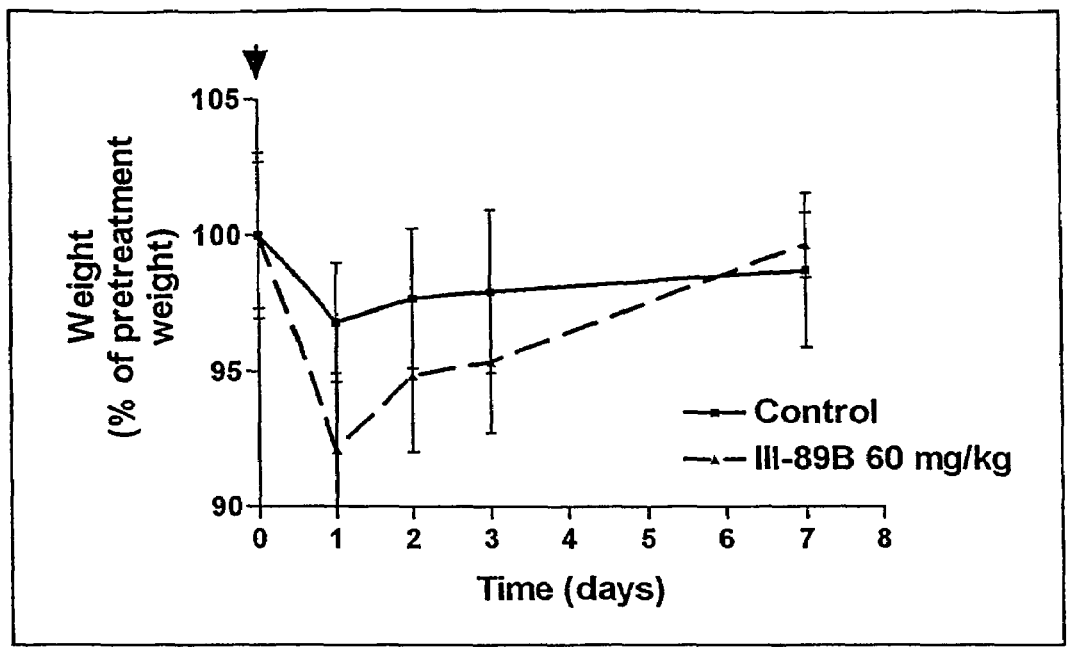
FIG. 11 shows the results of in vivo testing for weight loss of certain compounds according to the invention.
Figure 11:
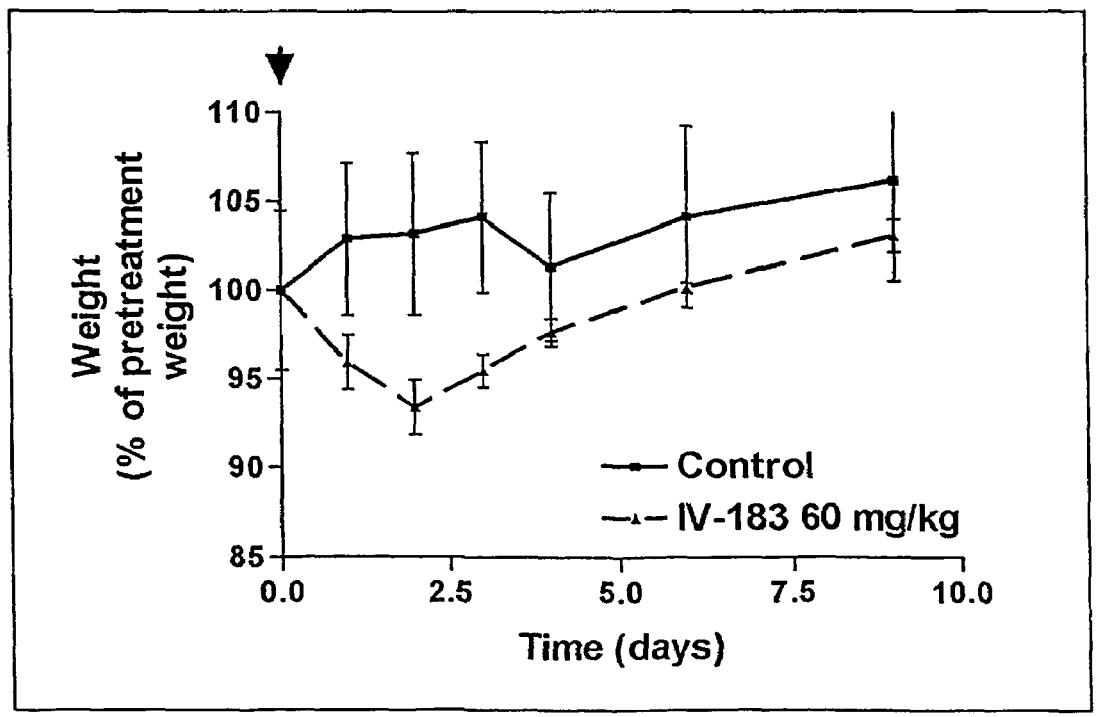
Figure 12:
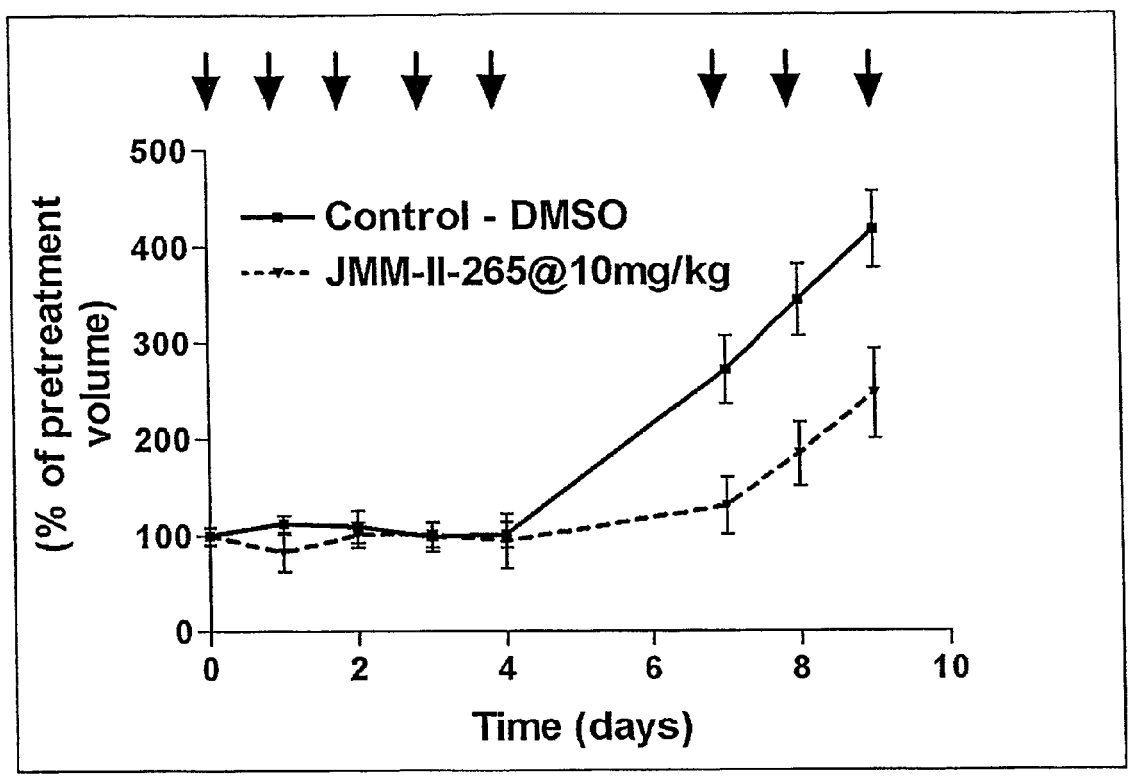
FIG. 12 shows the results of in vivo testing for anti-cancer activity of a compound according to the invention.

The results of this experiment are shown in FIG. 11. Subcutaneous flank xenografts of the human colon cancer cell line, HCT-116 in nu/nu female mice (Harlan) were used to study the anti-tumor effects of Compound 36 in vivo. All animal experiments complied with institutional animal care guidelines. $10^7$ HCT-116 cells (~0.1 ml packed cells) were xenografted from culture in DMEM supplemented with 10% FBS into 10 athymic mice. Treatment began when measurable tumors developed about 4 days after inoculation. Compound 36 (10 mg/kg) was diluted into 20 µl DMSO and treated intraperitoneally, i.p. Five animals received JMM-II-265 i.p. at days indicated by arrows in FIG. 11, and 5 received DMSO control. Tumors were measured on days indicated. Error bars represent standard error of the mean.

Results of the Biological Testing

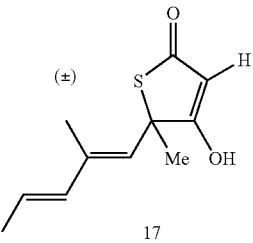

17

| FAS(IC$_{50}$) | $^{14}$C(IC$_{50}$) | XTT(IC$_{50}$) | Cr. Violet(IC$_{50}$) |
|---|---|---|---|
| 71.2 ug/ml | 17.3 ug/ml | >80 ug/ml | >50 ug/ml |
| CPT I Stim | | Weight Loss | |
| Not Tested | | 60 mg/kg: 4.1%(day1) | |
| SA/MH(MIC) | SA/Tsoy(MIC) | PSAE/MH(MIC) | PSAE/Tsoy(MIC) |
| 52 ug/ml | 87 ug/ml | Neg | Neg |
| EF/MH(MIC) | EF/Tsoy(MIC) | Ecoli/MH(MIC) | Ecoli/Tsoy(MIC) |
| Neg | Neg | Neg | Neg |
| FAS(IC$_{50}$) | $^{14}$C(IC$_{50}$) | XTT(IC$_{50}$) | Cr. Violet(IC$_{50}$) |
| 50.0 ug/ml | 16.9 ug/ml | >80 ug/ml | >50 ug/ml |

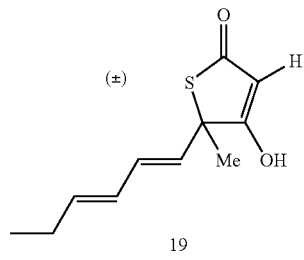

19

| FAS(IC$_{50}$) | $^{14}$C(IC$_{50}$) | XTT(IC$_{50}$) | Cr. Violet(IC$_{50}$) |
|---|---|---|---|
| 50.0 ug/ml | 16.9 ug/ml | >80 ug/ml | >50 ug/ml |
| CPT I Stim | | Weight Loss | |
| Not Tested | | 60 mg/kg: 3.2%(day5) | |
| SA/MH(MIC) | SA/Tsoy(MIC) | PSAE/MH(MIC) | PSAE/Tsoy(MIC) |
| 202 ug/ml | 85 ug/ml | Neg | Neg |
| EF/MH(MIC) | EF/Tsoy(MIC) | Ecoli/MH(MIC) | Ecoli/Tsoy(MIC) |
| 186 ug/ml | Neg | 225 ug/ml | Neg |

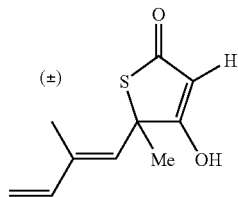

21

| FAS(IC$_{50}$) | $^{14}$C(IC$_{50}$) | XTT(IC$_{50}$) | Cr. Violet(IC$_{50}$) |
|---|---|---|---|
| 8.8 ± 0.02 ug/ml | 40.3 ± 11.5 ug/ml | >80 ug/ml | >50 ug/ml |
| CPT I Stim | | Weight Loss | |
| 95% of control | | 60 mg/kg: 7.8%(day3) | |
| at 20 ug/ml(MCF7) | | | |
| SA/MH(MIC) | SA/Tsoy(MIC) | PSAE/MH(MIC) | PSAE/Tsoy(MIC) |
| 235 ug/ml | 102 ug/ml | Neg | Neg |
| EF/MH(MIC) | EF/Tsoy(MIC) | Ecoli/MH(MIC) | Ecoli/Tsoy(MIC) |
| 220 ug/ml | Neg | 290 ug/ml | Neg |

-continued

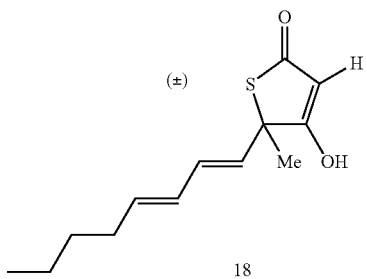

18

| FAS(IC$_{50}$) | $^{14}$C(IC$_{50}$) | XTT(IC$_{50}$) | Cr. Violet(IC$_{50}$) |
|---|---|---|---|
| 8.6 ± 1.7 ug/ml | 25.7 ug/ml | 59.4 ± 6.4 ug/ml | 43.9 ± 4.8 ug/ml |
| CPT I Stim | | Weight Loss | |
| 115% of control at 20 ug/ml(MCF7) | | 60 mg/kg: 11%(day6) | |
| SA/MH(MIC) | SA/Tsoy(MIC) | PSAE/MH(MIC) | PSAE/Tsoy(MIC) |
| Neg | 55 ug/ml | Neg | Neg |
| EF/MH(MIC) | EF/Tsoy(MIC) | Ecoli/MH(MIC) | Ecoli/Tsoy(MIC) |
| 78 ug/ml | 42 ug/ml | Neg | 263 ug/ml |

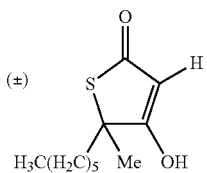

33

| FAS(IC$_{50}$) | $^{14}$C(IC$_{50}$) | XTT(IC$_{50}$) | Cr. Violet(IC$_{50}$) |
|---|---|---|---|
| Neg | 16.5 ± 3.8 ug/ml | >80 ug/ml | >50 ug/ml |
| CPT I Stim | | Weight Loss | |
| Not Tested | | 60 mg/kg: 3 of 3 dead(day4) | |
| SA/MH(MIC) | SA/Tsoy(MIC) | PSAE/MH(MIC) | PSAE/Tsoy(MIC) |
| 48 ug/ml | 31 ug/ml | Neg | Neg |
| EF/MH(MIC) | EF/Tsoy(MIC) | Ecoli/MH(MIC) | Ecoli/Tsoy(MIC) |
| 98 ug/ml | 43 ug/ml | Neg | Neg |

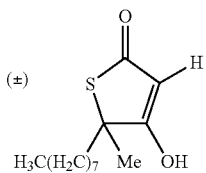

32

| FAS(IC$_{50}$) | $^{14}$C(IC$_{50}$) | XTT(IC$_{50}$) | Cr. Violet(IC$_{50}$) |
|---|---|---|---|
| 4.5 ug/ml | 12.6 ± 4.4 ug/ml | 17.6 ± 0.1 ug/ml | 28.7 ug/ml |
| CPT I Stim | | Weight Loss | |
| 115% of control | | 60 mg/kg: 2% and 0.3%(day1), 30 mg/kg: 4.8%(day3) | |
| SA/MH(MIC) | SA/Tsoy(MIC) | PSAE/MH(MIC) | PSAE/Tsoy(MIC) |
| Neg | 47 ug/ml | Neg | Neg |
| EF/MH(MIC) | EF/Tsoy(MIC) | Ecoli/MH(MIC) | Ecoli/Tsoy(MIC) |
| 16.9 ug/ml | 3.3 ug/ml | Neg | 278 ug/ml |

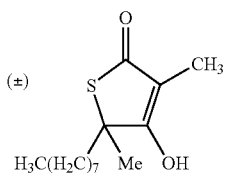

34

| FAS(IC$_{50}$) | $^{14}$C(IC$_{50}$) | XTT(IC$_{50}$) | Cr. Violet(IC$_{50}$) |
|---|---|---|---|
| 49.2 ± 1.9 ug/ml | 16.5 ± 5.7 ug/ml | 48.0 ± 1.4 ug/ml | 29.4 ± 4.3ug/ml |
| CPT I Stim | | Weight Loss | |

Not Tested       60 mg/kg: 0%(day1), 30 mg/kg: +1%(day1)
SA/MH(MIC)       SA/Tsoy(MIC)     PSAE/MH(MIC)     PSAE/Tsoy(MIC)
45 ± 2 ug/ml     23.5 ± 0.4 ug/ml  Neg              Neg
EF/MH(MIC)       EF/Tsoy(MIC)     Ecoli/MH(MIC)    Ecoli/Tsoy(MIC)
44 ug/ml         105 ug/ml        Neg              290 ug/ml

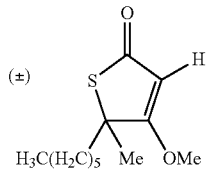

36

FAS($IC_{50}$)     $^{14}C(IC_{50})$    XTT($IC_{50}$)       Cr. Violet($IC_{50}$)
Neg              14.0 ± 2.8 ug/ml  9.4 ± 1.5 ug/ml  26.3 ± 4.3ug/ml
CPT I Stim                        Weight Loss
Not Tested       60 mg/kg: 3 of 3 dead(day1); 30mg/kg: 8.7%(day1)
                 10 mg/kg(multiple doses): 1% (day3)
SA/MH(MIC)       SA/Tsoy(MIC)     PSAE/MH(MIC)     PSAE/Tsoy(MIC)
45 ug/ml         48 ug/ml         Neg              Neg
EF/MH(MIC)       EF/Tsoy(MIC)     Ecoli/MH(MIC)    Ecoli/Tsoy(MIC)
43 ug/ml         126 ug/ml        Neg              264 ug/ml

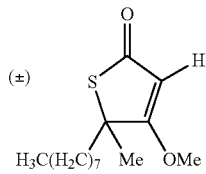

35

FAS($IC_{50}$)     $^{14}C(IC_{50})$    XTT($IC_{50}$)       Cr. Violet($IC_{50}$)
Neg              11.0 ug/ml       16.4 ± 2.3 ug/ml  21.4 ug/ml
CPT I Stim                        Weight Loss
Not Tested       60 mg/kg: 6.1%(day1), didn'tregain; 30 mg/kg: 0 and 5.7%(day4)
SA/MH(MIC)       SA/Tsoy(MIC)     PSAE/MH(MIC)     PSAE/Tsoy(MIC)
252 ug/ml        67 ug/ml         Neg              Neg
EF/MH(MIC)       EF/Tsoy(MIC)     Ecoli/MH(MIC)    Ecoli/Tsoy(MIC)
72 ug/ml         Neg              Neg              Neg

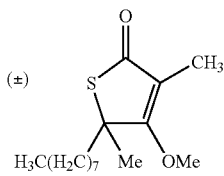

37

FAS($IC_{50}$)     $^{14}C(IC_{50})$    XTT($IC_{50}$)       Cr. Violet($IC_{50}$)
Neg              63.8 ug/ml       17.3 ± 5.9 ug/ml  15.9 ± 1.9ug/ml
CPT I Stim                        Weight Loss
Not Tested                        Not Tested
SA/MH(MIC)       SA/Tsoy(MIC)     PSAE/MH(MIC)     PSAE/Tsoy(MIC)
132 ug/ml        108 ug/ml        Neg              Neg
EF/MH(MIC)       EF/Tsoy(MIC)     Ecoli/MH(MIC)    Ecoli/Tsoy(MIC)
208 ug/ml        94 ug/ml         Neg              Neg -continued

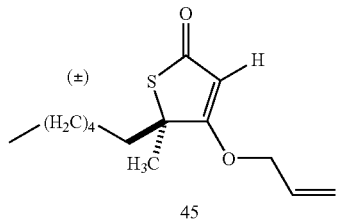

45

| FAS(IC$_{50}$) | $^{14}$C(IC$_{50}$) | XTT(IC$_{50}$) | Cr. Violet(IC$_{50}$) |
|---|---|---|---|
| Neg | Neg | 9.0 ± 1.1 ug/ml | 8.1 ug/ml |
| CPT I Stim | | Weight Loss | |
| Not Tested | 60 mg/kg: 2 of 3 dead(day2); 30 mg/kg: 8.8%(day2) | | |
| SA/MH(MIC) | SA/Tsoy(MIC) | PSAE/MH(MIC) | PSAE/Tsoy(MIC) |
| 73 ug/ml | 54 ug/ml | Neg | Neg |
| EF/MH(MIC) | EF/Tsoy(MIC) | Ecoli/MH(MIC) | Ecoli/Tsoy(MIC) |
| Neg | 158 ug/ml | Neg | Neg |

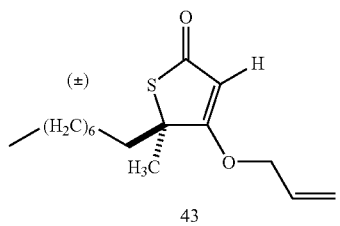

43

| FAS(IC$_{50}$) | $^{14}$C(IC$_{50}$) | XTT(IC$_{50}$) | Cr. Violet(IC$_{50}$) |
|---|---|---|---|
| Neg | Neg | 14.5 ± 1.5 ug/ml | 11.0 ug/ml |
| CPT I Stim | | Weight Loss | |
| Not Tested | 60 mg/kg: 3 of 3 dead(day3); 30 mg/kg: 4.7% and 3%(day2) | | |
| SA/MH(MIC) | SA/Tsoy(MIC) | PSAE/MH(MIC) | PSAE/Tsoy(MIC) |
| 127 ug/ml | 85 ug/ml | Neg | Neg |
| EF/MH(MIC) | EF/Tsoy(MIC) | Ecoli/MH(MIC) | Ecoli/Tsoy(MIC) |
| 238 ug/ml | 238 ug/ml | Neg | Neg |

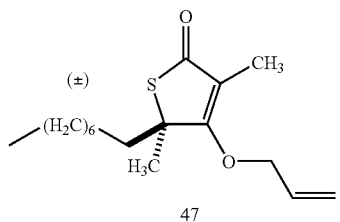

47

| FAS(IC$_{50}$) | $^{14}$C(IC$_{50}$) | XTT(IC$_{50}$) | Cr. Violet(IC$_{50}$) |
|---|---|---|---|
| Not Tested | Neg | Not Tested | 15.1 ug/ml |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| Not Tested | Not Tested | Not Tested | Not Tested |
| EF/MH(MIC) | EF/Tsoy(MIC) | Ecoli/MH(MIC) | Ecoli/Tsoy(MIC) |
| Not Tested | Not Tested | Not Tested | Not Tested |

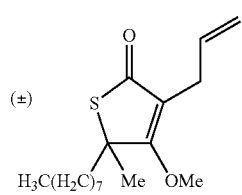

44

| FAS(IC$_{50}$) | $^{14}$C(IC$_{50}$) | XTT(IC$_{50}$) | Cr. Violet(IC$_{50}$) |
|---|---|---|---|
| Neg | 23.1 ± 17.4 ug/ml | 55.0 ± 2.0 ug/ml | 22.3 ug/ml |
| CPT I Stim | | Weight Loss | |
| 125% of control | 60 mg/kg: 7.9% and 8.0%(day1) | | |
| at 20 ug/ml(MCF7) | | | |

| | | | |
|---|---|---|---|
| SA/MH(MIC) | SA/Tsoy(MIC) | PSAE/MH(MIC) | PSAE/Tsoy(MIC) |
| Neg | 98 ug/ml | Neg | Neg |
| EF/MH(MIC) | EF/Tsoy(MIC) | Ecoli/MH(MIC) | Ecoli/Tsoy(MIC) |
| Neg | 169 ug/ml | Neg | Neg |

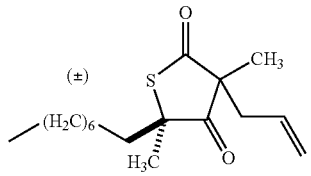

48

| | | | |
|---|---|---|---|
| FAS(IC$_{50}$) | $^{14}$C(IC$_{50}$) | XTT(IC$_{50}$) | Cr. Violet(IC$_{50}$) |
| Neg | 14.9 ug/ml | 50.4 ± 4.7 ug/ml | >50 ug/ml |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| Neg | 97 ug/ml | Neg | Neg |
| EF/MH(MIC) | EF/Tsoy(MIC) | Ecoli/MH(MIC) | Ecoli/Tsoy(MIC) |
| 133 ug/ml | 91 ug/ml | Neg | Neg |

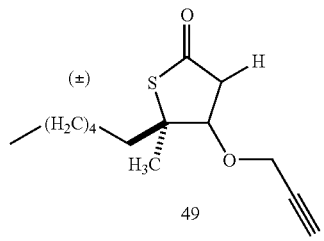

49

| | | | |
|---|---|---|---|
| FAS(IC$_{50}$) | $^{14}$C(IC$_{50}$) | XTT(IC$_{50}$) | Cr. Violet(IC$_{50}$) |
| Neg | 21.9 ± 1.5 ug/ml | 8.9 ± 2.3 ug/ml | 12.1 ± 1.5 ug/ml |
| CPT I Stim | | Weight Loss | |
| Not Tested | 60 mg/kg: 3 of 3 dead(day2); 30 mg/kg: 5.9% and 3%(day3) | | |
| SA/MH(MIC) | SA/Tsoy(MIC) | PSAE/MH(MIC) | PSAE/Tsoy(MIC) |
| 53 ug/ml | 80 ug/ml | Neg | Neg |
| EF/MH(MIC) | EF/Tsoy(MIC) | Ecoli/MH(MIC) | Ecoli/Tsoy(MIC) |
| Neg | 83 ug/ml | 203 ug/ml | Neg |

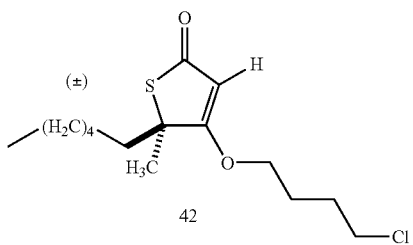

42

| | | | |
|---|---|---|---|
| FAS(IC$_{50}$) | $^{14}$C(IC$_{50}$) | XTT(IC$_{50}$) | Cr. Violet(IC$_{50}$) |
| Neg | 8.6 ug/ml | 20.8 ± 0.9 ug/ml | 16.3 ug/ml |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| 164 ug/ml | 50 ug/ml | Neg | Neg |
| EF/MH(MIC) | EF/Tsoy(MIC) | Ecoli/MH(MIC) | Ecoli/Tsoy(MIC) |
| 117 ug/ml | 165 ug/ml | Neg | Neg |

-continued

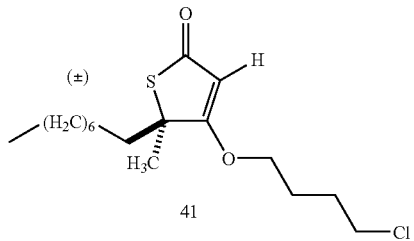

41

| FAS(IC$_{50}$) | $^{14}$C(IC$_{50}$) | XTT(IC$_{50}$) | Cr. Violet(IC$_{50}$) |
|---|---|---|---|
| Neg | 6.8 ug/ml | 35.3 ± 2.2 ug/ml | 10.3 ± 0.3ug/ml |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| 115 ug/ml | 134 ug/ml | Neg | Neg |
| EF/MH(MIC) | EF/Tsoy(MIC) | Ecoli/MH(MIC) | Ecoli/Tsoy(MIC) |
| 64 ug/ml | Neg | Neg | Neg |

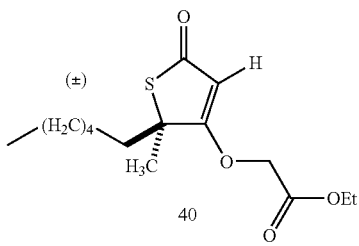

40

| FAS(IC$_{50}$) | $^{14}$C(IC$_{50}$) | XTT(IC$_{50}$) | Cr. Violet(IC$_{50}$) |
|---|---|---|---|
| Neg | 14.2 ± 0.2 ug/ml | 39.6 ± 2.2 ug/ml | 17.0 ug/ml |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| Neg | 129 ug/ml | Neg | Neg |
| EF/MH(MIC) | EF/Tsoy(MIC) | Ecoli/MH(MIC) | Ecoli/Tsoy(MIC) |
| 21.3 ug/ml | Neg | Neg | 281 ug/ml |

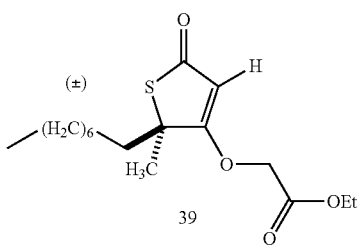

39

| FAS(IC$_{50}$) | $^{14}$C(IC$_{50}$) | XTT(IC$_{50}$) | Cr. Violet(IC$_{50}$) |
|---|---|---|---|
| Neg | 10.8 ± 5.8 ug/ml | 35.3 ± 10.4 ug/ml | 17.9 ± 5.1 ug/ml |
| CPT I Stim | | Weight Loss | |
| Not Tested | 60 mg/kg: 1.8% and 3.6%(day 1); 30 mg/kg: 4.5%(day1) | | |
| SA/MH(MIC) | SA/Tsoy(MIC) | PSAE/MH(MIC) | PSAE/Tsoy(MIC) |
| Neg | 83 ug/ml | Neg | Neg |
| EF/MH(MIC) | EF/Tsoy(MIC) | Ecoli/MH(MIC) | Ecoli/Tsoy(MIC) |
| 86 ug/ml | Neg | Neg | Neg |

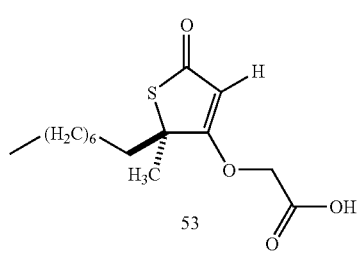

53

| FAS(IC$_{50}$) | $^{14}$C(IC$_{50}$) | XTT(IC$_{50}$) | Cr. Violet(IC$_{50}$) |
|---|---|---|---|
| Neg | 13.8 ± 1.1 ug/ml | 50.3 ± 2.8 ug/ml | 33.7 ug/ml |

| CPT I Stim | | Weight Loss | |
|---|---|---|---|
| Not Tested | | Not Tested | |
| SA/MH(MIC) | SA/Tsoy(MIC) | PSAE/MH(MIC) | PSAE/Tsoy(MIC) |
| 98 ug/ml | 60 ug/ml | Neg | Neg |
| EF/MH(MIC) | EF/Tsoy(MIC) | Ecoli/MH(MIC) | Ecoli/Tsoy(MIC) |
| 77 ug/ml | 164 ug/ml | Neg | Neg |

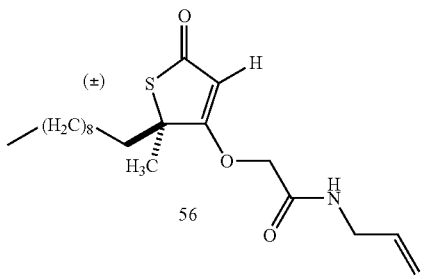

| FAS(IC$_{50}$) | $^{14}$C(IC$_{50}$) | XTT(IC$_{50}$) | Cr. Violet(IC$_{50}$) |
|---|---|---|---|
| Neg | Neg | 12.1 ± 0.6 ug/ml | 10.4 ug/ml |
| CPT I Stim | | Weight Loss | |
| Not Tested | | 30 mg/kg: 1.8%(day2), 15 mg/kg: 0%(day1) | |
| SA/MH(MIC) | SA/Tsoy(MIC) | PSAE/MH(MIC) | PSAE/Tsoy(MIC) |
| 28 ug/ml | 31 ug/ml | Neg | Neg |
| EF/MH(MIC) | EF/Tsoy(MIC) | Ecoli/MH(MIC) | Ecoli/Tsoy(MIC) |
| Not Tested | Not Tested | Not Tested | Not Tested |

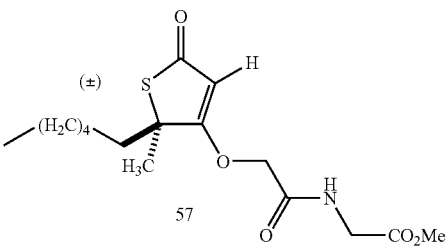

| FAS(IC$_{50}$) | $^{14}$C(IC$_{50}$) | XTT(IC$_{50}$) | Cr. Violet(IC$_{50}$) |
|---|---|---|---|
| Neg | 9.8 ug/ml | 40.5 ± 5.1 ug/ml | 32.5 ± 11.7 ug/ml |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| 69 ug/ml | 111 ug/ml | Neg | Neg |
| EF/MH(MIC) | EF/Tsoy(MIC) | Ecoli/MH(MIC) | Ecoli/Tsoy(MIC) |
| Neg | Neg | 156 ug/ml | Neg |

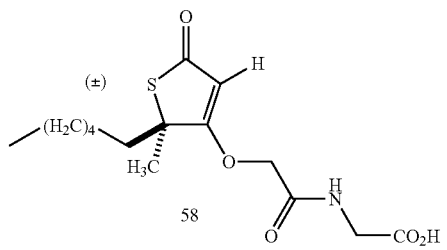

| FAS(IC$_{50}$) | $^{14}$C(IC$_{50}$) | XTT(IC$_{50}$) | Cr. Violet(IC$_{50}$) |
|---|---|---|---|
| Neg | 6.6 ug/ml | >80 ug/ml | >50 ug/ml |
| CPT I Stim | | Weight Loss | |
| Not Tested | | 60 mg/kg: 3.5%(day2), | |
| SA/MH(MIC) | SA/Tsoy(MIC) | PSAE/MH(MIC) | PSAE/Tsoy(MIC) |
| 78 ug/ml | 225 ug/ml | Neg | Neg |
| EF/MH(MIC) | EF/Tsoy(MIC) | Ecoli/MH(MIC) | Ecoli/Tsoy(MIC) |
| 121 ug/ml | 173 ug/ml | Neg | 235 ug/ml |

-continued

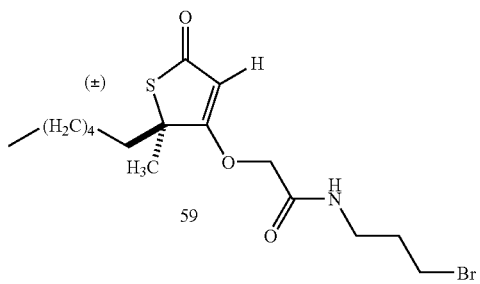
59

| FAS(IC$_{50}$) | $^{14}$C(IC$_{50}$) | XTT(IC$_{50}$) | Cr. Violet(IC$_{50}$) |
|---|---|---|---|
| Neg | 6.7 ug/ml | 21.2 ± 1.1 ug/ml | 12.6 ± 3.7 ug/ml |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| 147 ug/ml | 237 ug/ml | Neg | Neg |
| EF/MH(MIC) | EF/Tsoy(MIC) | Ecoli/MH(MIC) | Ecoli/Tsoy(MIC) |
| 99 ug/ml | 121 ug/ml | Neg | 293 ug/ml |

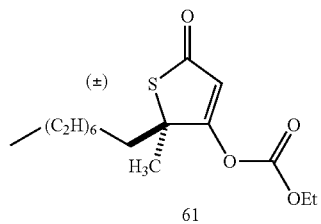
61

| FAS(IC$_{50}$) | $^{14}$C(IC$_{50}$) | XTT(IC$_{50}$) | Cr. Violet(IC$_{50}$) |
|---|---|---|---|
| 3.0 ± 0.8 | 14.5 ± 6.9 ug/ml | 15.1 ± 2.6 ug/ml | 31.4 ± 5.7 ug/ml |
| CPT I Stim | | Weight Loss | |
| 150% of control | 60 mg/kg: 6.9% and 5.7%(day 2); 30 mg/kg: 1.3%(day4) | | |
| at 20 ug/ml(MCF7) | | | |
| SA/MH(MIC) | SA/Tsoy(MIC) | PSAE/MH(MIC) | PSAE/Tsoy(MIC) |
| 45 ug/ml | 83 ug/ml | Neg | Neg |
| EF/MH(MIC) | EF/Tsoy(MIC) | Ecoli/MH(MIC) | Ecoli/Tsoy(MIC) |
| 86 ug/ml | 62 ug/ml | Neg | Neg |

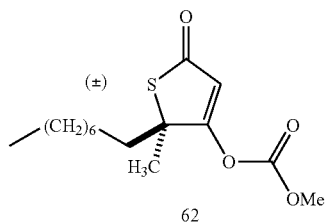
62

| FAS(IC$_{50}$) | $^{14}$C(IC$_{50}$) | XTT(IC$_{50}$) | Cr. Violet(IC$_{50}$) |
|---|---|---|---|
| 1.8 ug/ml | 10.7 ug/ml | 21.6 ± 0.2 ug/ml | 41.4 ± 14.1 ug/ml |
| CPT I Stim | | Weight Loss | |
| Not Tested | | 60 mg/kg: 7.65%(day 1); | |
| SA/MH(MIC) | SA/Tsoy(MIC) | PSAE/MH(MIC) | PSAE/Tsoy(MIC) |
| 64 ug/ml | 41 ug/ml | Neg | Neg |
| EF/MH(MIC) | EF/Tsoy(MIC) | Ecoli/MH(MIC) | Ecoli/Tsoy(MIC) |
| 73 ug/ml | 65 ug/ml | 296 ug/ml | Neg |

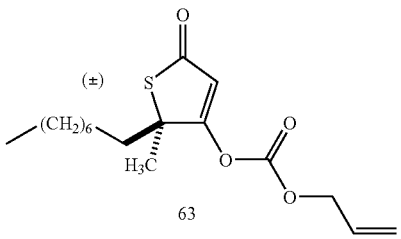

63

| FAS(IC$_{50}$) | $^{14}$C(IC$_{50}$) | XTT(IC$_{50}$) | Cr. Violet(IC$_{50}$) |
|---|---|---|---|
| 5.5 ug/ml | 14.2 ug/ml | 34.9 ± 10.0 ug/ml | 35.8 ug/ml |
| CPT I Stim | | Weight Loss | |
| Not Tested | | 60 mg/kg: 6.2%(day2); 30 mg/kg: 1%(day2) | |
| SA/MH(MIC) | SA/Tsoy(MIC) | PSAE/MH(MIC) | PSAE/Tsoy(MIC) |
| 57 ug/ml | 28 ug/ml | Neg | Neg |
| EF/MH(MIC) | EF/Tsoy(MIC) | Ecoli/MH(MIC) | Ecoli/Tsoy(MIC) |
| 79 ug/ml | 75 ug/ml | 82 ug/ml | 87 ug/ml |

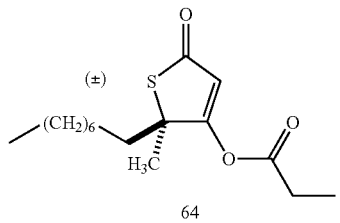

64

| FAS(IC$_{50}$) | $^{14}$C(IC$_{50}$) | XTT(IC$_{50}$) | Cr. Violet(IC$_{50}$) |
|---|---|---|---|
| Neg | 22.6 ug/ml | 26.8 ± 0.6 ug/ml | 38.6 ug/ml |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| 88 ug/ml | 62 ug/ml | Neg | Neg |
| EF/MH(MIC) | EF/Tsoy(MIC) | Ecoli/MH(MIC) | Ecoli/Tsoy(MIC) |
| 102 ug/ml | 147 ug/ml | Neg | Neg |

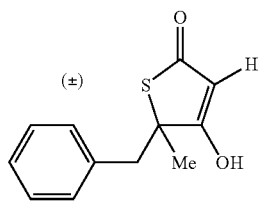

22

| FAS(IC$_{50}$) | $^{14}$C(IC$_{50}$) | XTT(IC$_{50}$) | Cr. Violet(IC$_{50}$) |
|---|---|---|---|
| Neg | Neg | >80 ug/ml | >50 ug/ml |
| CPT I Stim | | Weight Loss | |
| Not Tested | | 60 mg/kg: 1.6%(day2); | |
| SA/MH(MIC) | SA/Tsoy(MIC) | PSAE/MH(MIC) | PSAE/Tsoy(MIC) |
| 57 ug/ml | 67 ug/ml | Neg | Neg |
| EF/MH(MIC) | EF/Tsoy(MIC) | Ecoli/MH(MIC) | Ecoli/Tsoy(MIC) |
| 128 ug/ml | Neg | Neg | 299 ug/ml |

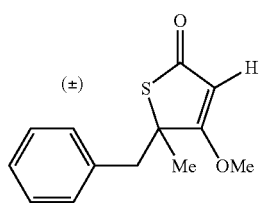

38

| FAS(IC$_{50}$) | $^{14}$C(IC$_{50}$) | XTT(IC$_{50}$) | Cr. Violet(IC$_{50}$) |
|---|---|---|---|
| Neg | Not Tested | 61.3 ± 3.9 ug/ml | 20.9 ug/ml |

-continued

| | | | |
|---|---|---|---|
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| 83 ug/ml | 129 ug/ml | Neg | Neg |
| EF/MH(MIC) | EF/Tsoy(MIC) | Ecoli/MH(MIC) | Ecoli/Tsoy(MIC) |
| 170 ug/ml | 189 ug/ml | Neg | Neg |

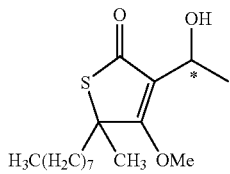

66

| | | | |
|---|---|---|---|
| FAS(IC$_{50}$) | $^{14}$C(IC$_{50}$) | XTT(IC$_{50}$) | Cr. Violet(IC$_{50}$) |
| 2.8 ug/ml | 21.7 ug/ml | 21.0 ± 2.9 ug/ml | 23.2 ug/ml |
| CPT I Stim | | Weight Loss | |
| Not Tested | | 30 mg/kg: 0.2%(day2); | |
| SA/MH(MIC) | SA/Tsoy(MIC) | PSAE/MH(MIC) | PSAE/Tsoy(MIC) |
| 53.3 ± 2.1 ug/ml | 16.2 ± 3.8 ug/ml | Neg | Neg |
| EF/MH(MIC) | EF/Tsoy(MIC) | Ecoli/MH(MIC) | Ecoli/Tsoy(MIC) |
| 77 ug/ml | 25 ug/ml | Neg | 249 ug/ml |

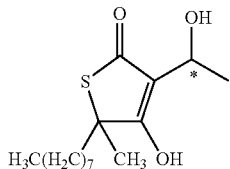

67

| | | | |
|---|---|---|---|
| FAS(IC$_{50}$) | $^{14}$C(IC$_{50}$) | XTT(IC$_{50}$) | Cr. Violet(IC$_{50}$) |
| 3.3 ug/ml | 17.6 ug/ml | 23.9 ± 2.9 ug/ml | 19.5 ug/ml |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| 53.1 ± 0.5 ug/ml | 12.0 ± 0.5 ug/ml | Neg | Neg |
| EF/MH(MIC) | EF/Tsoy(MIC) | Ecoli/MH(MIC) | Ecoli/Tsoy(MIC) |
| 66 ug/ml | 21 ug/ml | Neg | Neg |

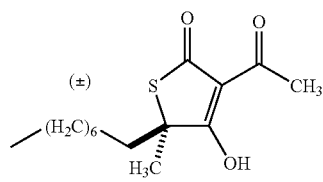

68

| | | | |
|---|---|---|---|
| FAS(IC$_{50}$) | $^{14}$C(IC$_{50}$) | XTT(IC$_{50}$) | Cr. Violet(IC$_{50}$) |
| Neg | 12.1 ± 0.1 ug/ml | 125 ± 0.7 ug/ml | 8.4 ug/ml |
| CPT I Stim | | Weight Loss | |
| Not Tested | | 60 mg/kg: 8.2%(day2); | |
| SA/MH(MIC) | SA/Tsoy(MIC) | PSAE/MH(MIC) | PSAE/Tsoy(MIC) |
| 3.4 ug/ml | 1.4 ug/ml | Neg | Neg |
| EF/MH(MIC) | EF/Tsoy(MIC) | Ecoli/MH(MIC) | Ecoli/Tsoy(MIC) |
| 2.5 ug/ml | 2.0 ug/ml | Neg | 177 ug/ml |

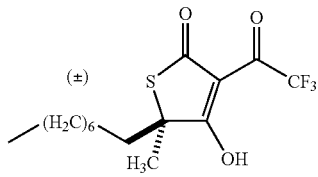

69

| FAS(IC$_{50}$) | $^{14}$C(IC$_{50}$) | XTT(IC$_{50}$) | Cr. Violet(IC$_{50}$) |
|---|---|---|---|
| 41.0 | 14.7 ug/ml | 18.4 ± 2.7 ug/ml | 45.3 ug/ml |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| 54 ug/ml | 65 ug/ml | Neg | Neg |
| EF/MH(MIC) | EF/Tsoy(MIC) | Ecoli/MH(MIC) | Ecoli/Tsoy(MIC) |
| Not Tested | Not Tested | Not Tested | Not Tested |

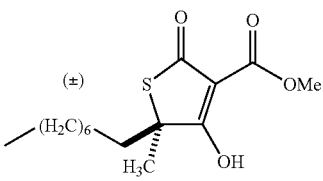

70

| FAS(IC$_{50}$) | $^{14}$C(IC$_{50}$) | XTT(IC$_{50}$) | Cr. Violet(IC$_{50}$) |
|---|---|---|---|
| Not Tested | Not Tested | Not Tested | Not Tested |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| Not Tested | 23 ug/ml | Neg | Neg |
| EF/MH(MIC) | EF/Tsoy(MIC) | Ecoli/MH(MIC) | Ecoli/Tsoy(MIC) |
| Not Tested | Not Tested | Not Tested | Not Tested |

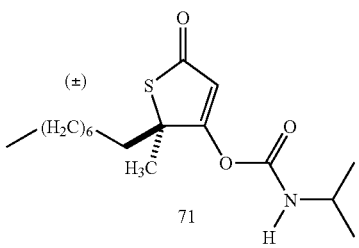

71

| FAS(IC$_{50}$) | $^{14}$C(IC$_{50}$) | XTT(IC$_{50}$) | Cr. Violet(IC$_{50}$) |
|---|---|---|---|
| 80.6 ug/ml | 23.1 ± 13.2 ug/ml | 45.7 ± 25.9 ug/ml | 22.5 ug/ml |
| CPT I Stim | | Weight Loss | |
| Not Tested | | Not Tested | |
| SA/MH(MIC) | SA/Tsoy(MIC) | PSAE/MH(MIC) | PSAE/Tsoy(MIC) |
| 32 ug/ml | 39 ug/ml | Neg | Neg |
| EF/MH(MIC) | EF/Tsoy(MIC) | Ecoli/MH(MIC) | Ecoli/Tsoy(MIC) |
| 60 ug/ml | 64 ug/ml | Neg | Neg |

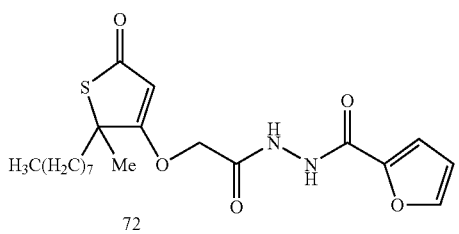

72

| FAS(IC$_{50}$) | $^{14}$C(IC$_{50}$) | XTT(IC$_{50}$) | Cr. Violet(IC$_{50}$) |
|---|---|---|---|
| Neg | 16.4 ug/ml | 26.4 ±ug/ml(M) | 26.3 ug/ml |
| | | 21.3 ug/ml(OV) | |
| CPT I Stim | | Weight Loss | |

-continued

| | | | |
|---|---|---|---|
| Not Tested | | 60 mg/kg: 6.3%(day4); | |
| SA/MH(MIC) | SA/Tsoy(MIC) | PSAE/MH(MIC) | PSAE/Tsoy(MIC) |
| Not Tested | Not Tested | Not Tested | Not Tested |
| EF/MH(MIC) | EF/Tsoy(MIC) | Ecoli/MH(MIC) | Ecoli/Tsoy(MIC) |
| Not Tested | Not Tested | Not Tested | Not Tested |

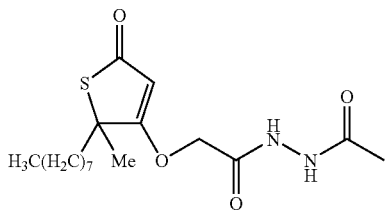

73

| | | | |
|---|---|---|---|
| FAS(IC$_{50}$) | $^{14}$C(IC$_{50}$) | XTT(IC$_{50}$) | Cr. Violet(IC$_{50}$) |
| Neg | 11.5 ug/ml | 25.3 ±ug/ml(M) | 28.7 ug/ml |
| | | 16.0 ug/ml(OV) | |
| CPT I Stim | | Weight Loss | |
| Not Tested | | 60 mg/kg: 5.9%(day4) | |
| SA/MH(MIC) | SA/Tsoy(MIC) | PSAE/MH(MIC) | PSAE/Tsoy(MIC) |
| Not Tested | Not Tested | Not Tested | Not Tested |
| EF/MH(MIC) | EF/Tsoy(MIC) | Ecoli/MH(MIC) | Ecoli/Tsoy(MIC) |
| Not Tested | Not Tested | Not Tested | Not Tested |

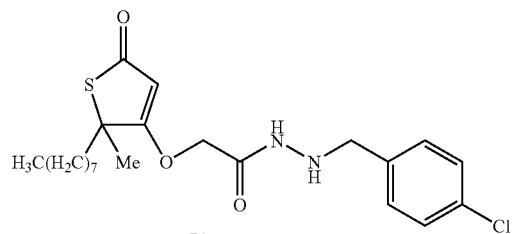

74

| | | | |
|---|---|---|---|
| FAS(IC$_{50}$) | $^{14}$C(IC$_{50}$) | XTT(IC$_{50}$) | Cr. Violet(IC$_{50}$) |
| Neg | 10.5 ± 2.6 ug/ml | 6.7 ±ug/ml(M) | <5 ug/ml |
| | | 16.0 ug/ml(OV) | |
| CPT I Stim | | Weight Loss | |
| Not Tested | | 60 mg/kg: 1.4%(day2) | |
| SA/MH(MIC) | SA/Tsoy(MIC) | PSAE/MH(MIC) | PSAE/Tsoy(MIC) |
| Not Tested | Not Tested | Not Tested | Not Tested |
| EF/MH(MIC) | EF/Tsoy(MIC) | Ecoli/MH(MIC) | Ecoli/Tsoy(MIC) |
| Not Tested | Not Tested | Not Tested | Not Tested |

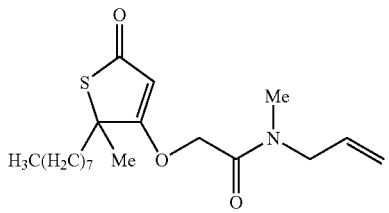

75

| | | | |
|---|---|---|---|
| FAS(IC$_{50}$) | $^{14}$C(IC$_{50}$) | XTT(IC$_{50}$) | Cr. Violet(IC$_{50}$) |
| Neg | 25.7 ug/ml | 9.2 ± 2.2 ug/ml(M) | 9.0 ug/ml |
| CPT I Stim | | Weight Loss | |
| Not Tested | | 60 mg/kg: 1.5%(day3) | |
| SA/MH(MIC) | SA/Tsoy(MIC) | PSAE/MH(MIC) | PSAE/Tsoy(MIC) |
| Not Tested | Not Tested | Not Tested | Not Tested |
| EF/MH(MIC) | EF/Tsoy(MIC) | Ecoli/MH(MIC) | Ecoli/Tsoy(MIC) |
| Not Tested | Not Tested | Not Tested | Not Tested |

-continued

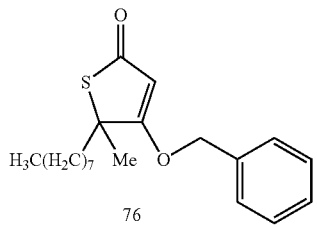

76

| FAS(IC$_{50}$) | $^{14}$C(IC$_{50}$) | XTT(IC$_{50}$) | Cr. Violet(IC$_{50}$) |
|---|---|---|---|
| Neg | Neg(stim) | 29.2 ±ug/ml(M) | 9.5 ug/ml |
|  |  | 27.8 ug/ml(OV) |  |
| CPT I Stim |  | Weight Loss |  |
| Not Tested |  | 60 mg/kg: 5.2%(day3) |  |
| SA/MH(MIC) | SA/Tsoy(MIC) | PSAE/MH(MIC) | PSAE/Tsoy(MIC) |
| Not Tested | Not Tested | Not Tested | Not Tested |
| EF/MH(MIC) | EF/Tsoy(MIC) | Ecoli/MH(MIC) | Ecoli/Tsoy(MIC) |
| Not Tested | Not Tested | Not Tested | Not Tested |

We claim:

1. A compound of formula I:

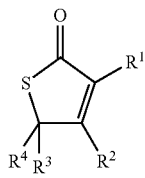

I wherein:
$R^1$=H
$R^2$=—OH, —OR$^5$, —OCH$_2$C(O)R$^5$, —OCH$_2$C(O)NHR$^5$, —OC(O)R$^5$, —OC(O)OR$^5$, —OC(O)NHNH—R$^5$, or —OC(O)NR$^5$R$^6$, where R$^5$ and R$^6$ are each independently H, C$_1$-C$_{20}$ alkyl, cycloalkyl, alkenyl, alkynyl, aryl, arylalkyl, or alkylaryl, and where R$^5$ and R$^6$ can each optionally contain halogen atoms;
$R^3$=H, C$_1$-C$_{20}$ alkyl, cycloalkyl, alkenyl, aryl, arylalkyl, or alkylaryl;
$R^4$=C$_1$-C$_{20}$ alkyl, cycloalkyl, alkenyl, aryl, arylalkyl, or alkylaryl;
with the proviso that when R$^2$ is —OH, —OCH$_3$, or —OC(O)CF$_3$ and R$^3$ is —CH$_3$, then R$^4$ is not —CH$_2$(C$_6$H$_5$), or —CH=CH—CH$_3$, and
the further proviso that when R$^3$ is —CH$_2$—(C$_6$H$_5$), then R$^4$ is not —CH$_3$ or —CH$_2$CH$_3$.

2. A compound according to claim 1, wherein R$^5$ is H, C$_1$-C$_{10}$ alkyl, cycloalkyl, alkenyl, alkynyl, aryl, arylalkyl or alkylaryl.

3. A compound according to claim 2, wherein R$^5$ is H, or C$_1$-C$_{10}$ alkyl.

4. A compound according to claim 1, wherein R$^3$ is H, C$_1$-C$_{10}$ alkyl, cycloalkyl, alkenyl, aryl, arylalkyl, or alkylaryl, and R$^4$ is C$_1$-C$_{10}$ alkyl, cycloalkyl, alkenyl, aryl, arylalkyl.

5. A compound according to claim 4, wherein R$^3$ is H, or C$_1$-C$_{10}$ alkyl, and R$^4$ is C$_1$-C$_{10}$ alkyl.

6. A compound according to claim 1, wherein, R$^3$ is —H or —CH$_3$.

7. A compound according to claim 1, wherein R$^4$ is -nC$_6$-C$_8$ alkyl.

8. A compound according to claim 1, wherein the compound is selected from the group consisting of:

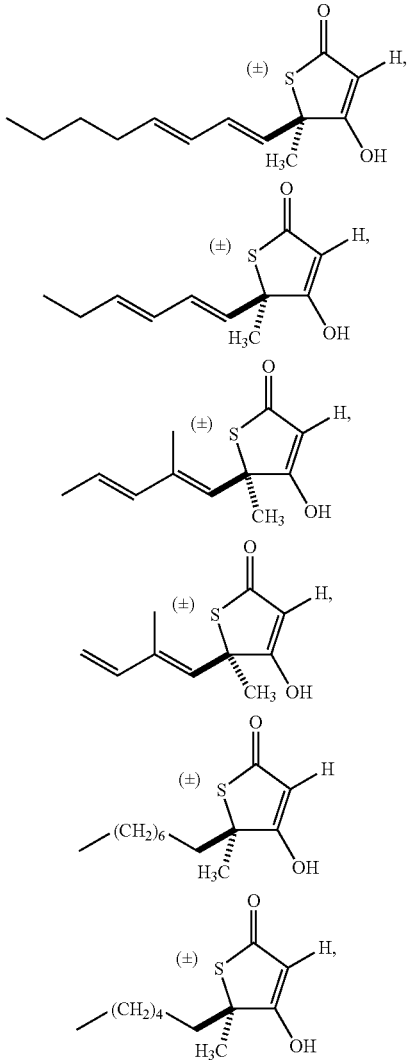

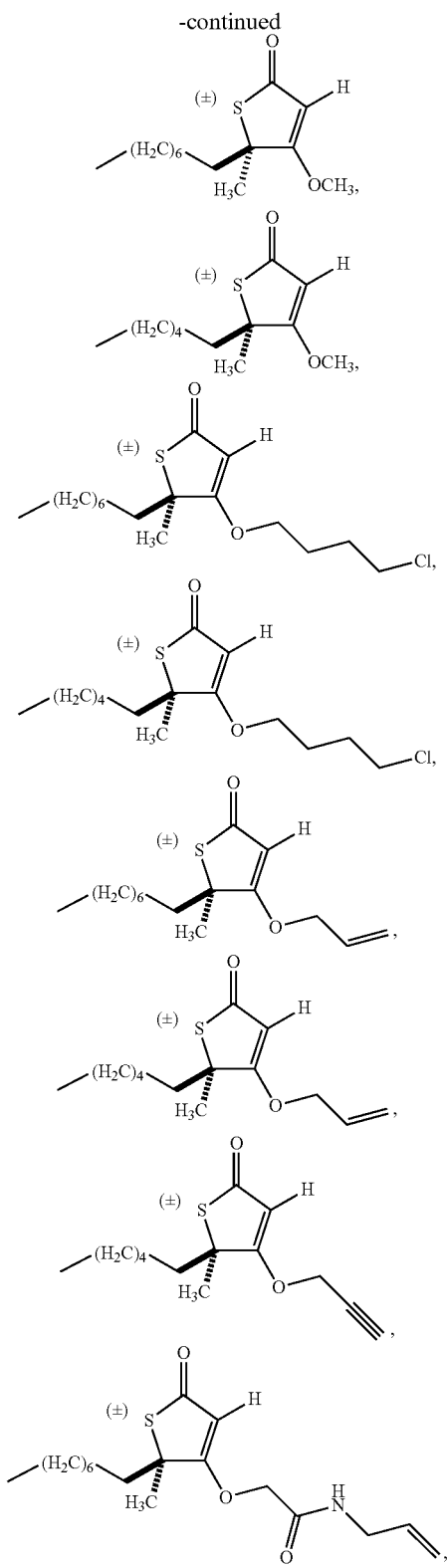
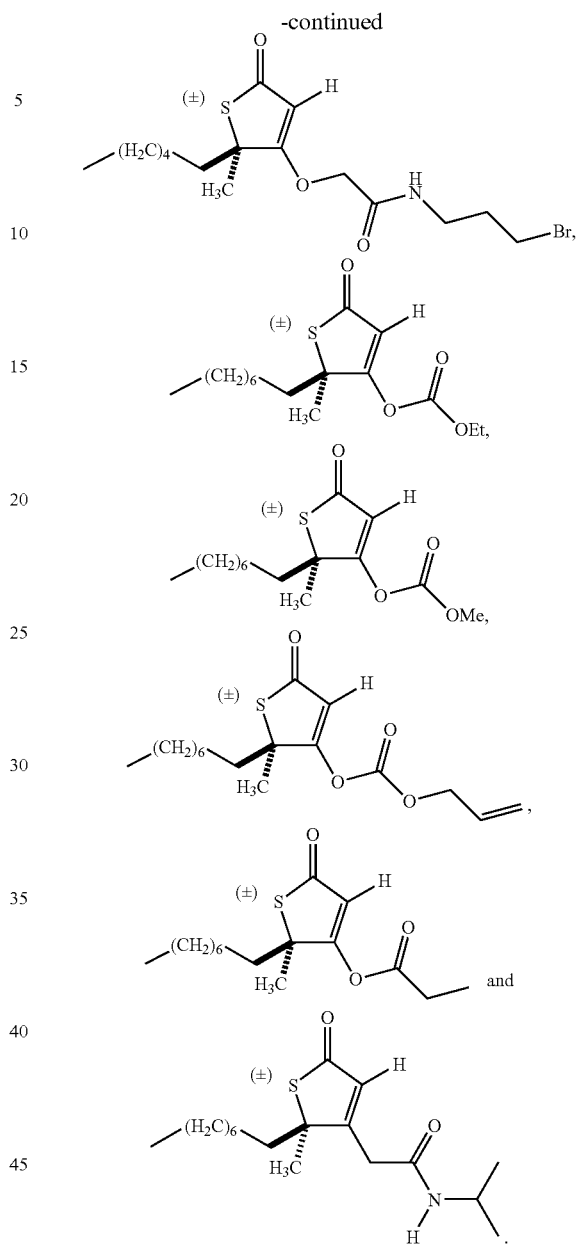
9. A pharmaceutical composition comprising a pharmaceutical diluent and a compound according to claim 1.
10. A compound according to claim 1, where:
$R^1$ is H;
$R^2$ is —$OCH_2C(O)NHR^5$, where $R^5$ is $C_1$-$C_{10}$ aryl containing a halogen atom;
$R^3$ is $CH_3$; and
$R^4$ is -n-$C_6$-$C_8$ alkyl.
11. A pharmaceutical composition comprising a pharmaceutical diluent and the compound of claim 10.
* * * * *

UNITED STATES PATENT AND TRADEMARK OFFICE
CERTIFICATE OF CORRECTION

PATENT NO. : 7,649,012 B2
APPLICATION NO. : 10/520505
DATED : January 19, 2010
INVENTOR(S) : Francis P. Kuhajda et al.

It is certified that error appears in the above-identified patent and that said Letters Patent is hereby corrected as shown below:

Title Page Under Item (75) Inventors:

add "Craig A. Townsend, Baltimore, MD (US)"

Signed and Sealed this
Twenty-eighth Day of December, 2010

David J. Kappos
*Director of the United States Patent and Trademark Office*